(12) United States Patent
Chen et al.

(10) Patent No.: US 11,873,294 B2
(45) Date of Patent: Jan. 16, 2024

(54) COMPOUND CONTAINING ANTHRONE AND NITROGEN-CONTAINING HETEROCYCLE AND APPLICATION IN OLED DEVICES

(71) Applicant: JIANGSU SUNERA TECHNOLOGY CO., LTD., Wuxi (CN)

(72) Inventors: Haifeng Chen, Wuxi (CN); Chong Li, Wuxi (CN); Zhaochao Zhang, Wuxi (CN); Xiaoqing Zhang, Wuxi (CN); Dandan Tang, Wuxi (CN)

(73) Assignee: JIANGSU SUNERA TECHNOLOGY CO., LTD., Wuxi (CN)

( * ) Notice: Subject to any disclaimer, the term of this patent is extended or adjusted under 35 U.S.C. 154(b) by 927 days.

(21) Appl. No.: 16/759,358

(22) PCT Filed: Sep. 25, 2018

(86) PCT No.: PCT/CN2018/107221
§ 371 (c)(1),
(2) Date: Jul. 17, 2020

(87) PCT Pub. No.: WO2019/085683
PCT Pub. Date: May 9, 2019

(65) Prior Publication Data
US 2020/0354347 A1 Nov. 12, 2020

(30) Foreign Application Priority Data
Nov. 2, 2017 (CN) .......................... 201711081106.9

(51) Int. Cl.
*H01L 51/50* (2006.01)
*C07D 405/10* (2006.01)
(Continued)

(52) U.S. Cl.
CPC ......... *C07D 405/10* (2013.01); *C07D 213/50* (2013.01); *C07D 239/26* (2013.01);
(Continued)

(58) Field of Classification Search
None
See application file for complete search history.

(56) References Cited

U.S. PATENT DOCUMENTS

2016/0248023 A1* 8/2016 Parham ............... C07F 15/0086

FOREIGN PATENT DOCUMENTS

| CN | 106467497 A | 3/2017 |
|---|---|---|
| CN | 106467516 A | 3/2017 |

(Continued)

*Primary Examiner* — Gregory D Clark
(74) *Attorney, Agent, or Firm* — Bayramoglu Law Offices LLC

(57) ABSTRACT

Disclosed are a compound with anthrone and N-containing heterocycle and an application thereof in an OLED. The compound contains anthrone and N-containing heterocycle structure which are both strong electron-withdrawing groups. The compound has a deep HOMO energy level and high electron mobility and is suitable for use as hole blocking materials or electron transport materials; the compound can also be used as a host material for electron-type light-emitting layers; in addition, the compound of the present invention has strong group rigidity, not easily causes crystallization and aggregation between molecules, and has good film-forming property. After the compound of the present invention is applied to an OLED device as an organic electroluminescent functional layer material, the current efficiency, power efficiency and external quantum efficiency of the device are greatly improved; moreover, the compound can improve the service life of the device.

6 Claims, 1 Drawing Sheet

(51) Int. Cl.
  *C07D 213/50* (2006.01)
  *C07D 239/26* (2006.01)
  *C07D 251/24* (2006.01)
  *C07D 401/04* (2006.01)
  *C07D 401/14* (2006.01)
  *C07D 405/14* (2006.01)
  *H10K 30/30* (2023.01)
  *H10K 50/16* (2023.01)

(52) U.S. Cl.
  CPC ......... *C07D 251/24* (2013.01); *C07D 401/04* (2013.01); *C07D 401/14* (2013.01); *C07D 405/14* (2013.01); *H10K 30/353* (2023.02); *H10K 50/16* (2023.02)

(56) References Cited

FOREIGN PATENT DOCUMENTS

| | | | | |
|---|---|---|---|---|
| CN | 106467542 A | | 3/2017 | |
| CN | 107056748 A | * | 8/2017 | ............. H01L 51/54 |
| CN | 107057681 A | | 8/2017 | |
| CN | 107068910 A | | 8/2017 | |

* cited by examiner

COMPOUND CONTAINING ANTHRONE AND NITROGEN-CONTAINING HETEROCYCLE AND APPLICATION IN OLED DEVICES

CROSS REFERENCE TO THE RELATED APPLICATIONS

This application is the national phase entry of International Application No. PCT/CN2018/107221, filed on Sep. 25, 2018, which is based upon and claims priority to Chinese Patent Application No. 201711081106.9, filed on Nov. 2, 2017, the entire contents of which are incorporated herein by reference.

TECHNICAL FIELD

The present invention relates to the field of semiconductor technology, and in particular, to a compound with anthrone and N-containing heterocycle and an application thereof in OLED.

BACKGROUND

Organic electroluminescent (OLED, Organic Light Emission Diodes) device technology can be used to fabricate not only a novel display product but also a novel lighting product. It is expected to replace the existing liquid crystal display and fluorescent lamp lighting, and has a promising application prospect. The OLED light-emitting device is of a sandwich structure, and includes an electrode material film layer and organic functional materials sandwiched between different electrode film layers, and various functional materials are overlapped with one another according to purposes so as to together form an OLED light-emitting device. Positive and negative charges in the organic functional material film layer are acted by the electric field and then combined in the light-emitting layer when the OLED light-emitting device serves as a current device and a voltage is applied to electrodes at two ends of the OLED light-emitting device, that is, the OLED electroluminescence is generated.

Currently, the OLED display technology has been applied in the fields of smart phones, tablet computers and the like, and will be further applied in the fields of large size devices such as TVs. However, compared with the actual product application requirements, the performances of OLED devices in luminous efficiency, service life, etc. still needs further improvement. Researches on improving the performance of the OLED light-emitting device include: reducing the driving voltage of the device, improving the light-emitting efficiency of the device, prolonging service life of the device, etc. In order to continuously improve the performance of the OLED device, not only the innovation from the structure and manufacturing process of OLED devices, but also the continuous research and innovation of OLED optoelectronic functional materials are needed to create OLED functional materials with higher performances. The OLED photoelectric functional materials used in OLED devices can be divided into two categories by their uses, namely charge injection transport materials and luminescent materials. Furthermore, charge injection transport materials can be divided into electron injection transport materials, electron blocking materials, hole injection transport materials and hole blocking materials, and the luminescent materials can also be divided into host luminescent materials and doping materials. In order to produce high-performance OLED light-emitting devices, various organic functional materials are required to have good photoelectric characteristics. For example, as a charge transport material, the material is required to have good carrier mobility, high glass transition temperature, etc.; as a host material of a light-emitting layer, the material needs to have good bipolarity, appropriate HOMO/LUMO energy level, etc.

The OLED photoelectric functional material film layer constituting the OLED device at least includes two or more layers, and the industrially applied OLED device structure includes various film layers such as a hole injection layer, a hole transport layer, an electron block layer, a light-emitting layer, a hole block layer, an electron transport layer, and an electron injection layer, that is to say, the photoelectric functional materials used in OLED devices at least include hole injection materials, hole transport materials, luminescent materials, electron transport materials, etc. Material types and matching forms are characterized by richness and diversity. In addition, for the matching of OLED devices with different structures, the optoelectronic functional materials used have strong selectivity, and the performance of the same materials in devices with different structures may also be completely different. Therefore, in view of the current industrial application requirements of OLED devices, as well as the different functional film layers of OLED devices and the photoelectric characteristic requirements of the device, a more suitable and high-performance OLED functional material or material combination must be chose in order to achieve the device's comprehensive characteristics of high efficiency, long service life and low voltage. As far as the actual demand of the current OLED display lighting industry is concerned, the current development of OLED materials is far from enough, lagging behind the requirements of panel manufacturing companies. For a material company, it is particularly important to develop higher-performance organic functional materials.

SUMMARY

In view of the problems existing in the prior art, the applicant provides a compound with anthrone and N-containing heterocycle and an application thereof in an organic electroluminescent device. With an anthrone structure, the compound of the present invention has a high glass transition temperature and molecular thermal stability, suitable HOMO and LUMO energy levels, and high electron mobility. After being applied to the fabrication of OLED devices, the compound can effectively improve the luminous efficiency and service life of the OLED devices.

The technical solutions of the present invention are as follows:

A compound with anthrone and N-containing heterocycle, wherein the structure of the compound is represented by formula (1):

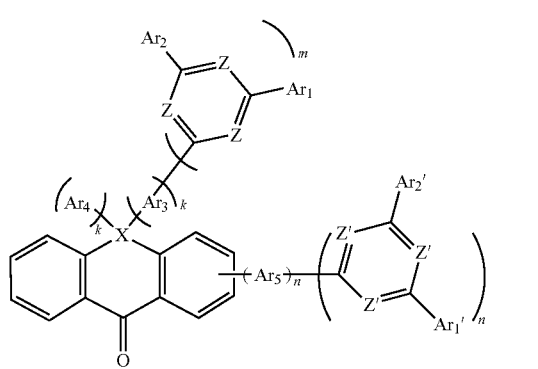

formula (1)

in formula (1), every time occurring, Z and Z' identically or differently represent CH, N or C—CN, wherein at least one Z group represents N or at least one Z' group represents N;

In formula (1), $Ar_1$, $Ar_2$, $Ar_2'$, and $Ar_4$ each independently represent hydrogen atom, substituted or unsubstituted aryl with 6 to 30 carbon atoms, or substituted or unsubstituted heteroaryl with 5 to 30 carbon atoms; $Ar_4$ further represents linear or branched alkyl with 1 to 10 carbon atoms;

in formula (1), $Ar_3$ and $Ar_5$ each independently represent single-bond, substituted or unsubstituted arylene with 6 to 30 carbon atoms, or substituted or unsubstituted heteroarylene with 5 to 30 carbon atoms; $Ar_3$ further represents linear or branched alkyl with 1 to 10 carbon atoms, substituted or unsubstituted aryl with 6 to 30 carbon atoms, or substituted or unsubstituted heteroaryl with 5 to 30 carbon atoms;

in formula (1), X represents carbon atom, oxygen atom or sulfur atom;

when X represents carbon atom, k=1, m and n each independently represent 0 or 1, and m and n are different;

when X represents oxygen atom or sulfur atom, k=0, m=0, n=1.

The structure of the compound may also be represented by formula (2), formula (3), formula (4), formula (5), formula (6), formula (7) or formula (8):

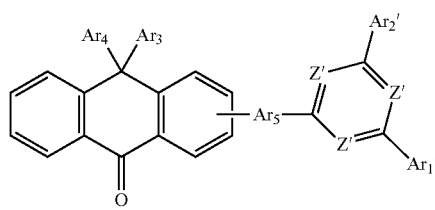

formula (2)

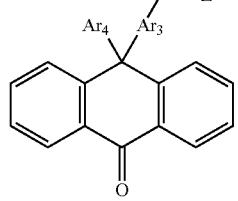

formula (3)

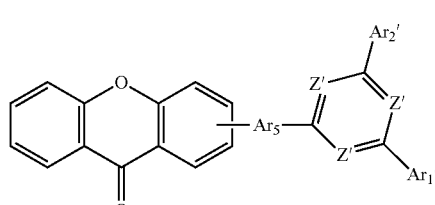

formula (4)

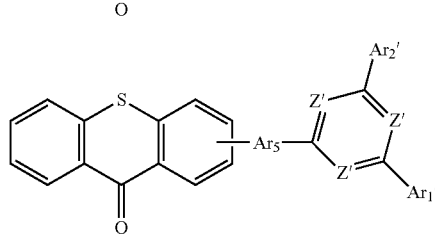

formula (5)

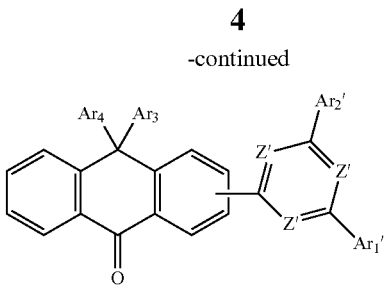

formula (6)

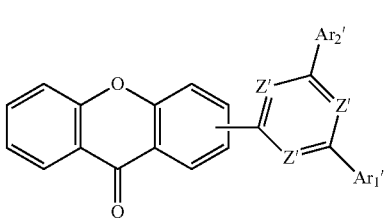

formula (7)

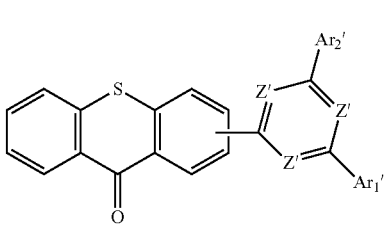

formula (8)

In the structure of formula (1), it is preferred that: $Ar_3$ and $Ar_5$ each independently represent phenylene, biphenylene or naphthylene; $Ar_3$ also represents methyl, phenyl, biphenyl or naphthyl; $Ar_4$ represents methyl, phenyl, biphenyl or naphthyl.

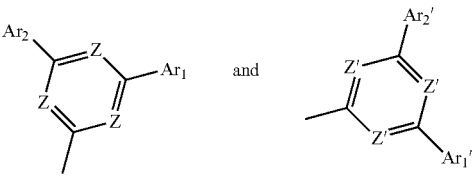

in formula (1) each independently represent:

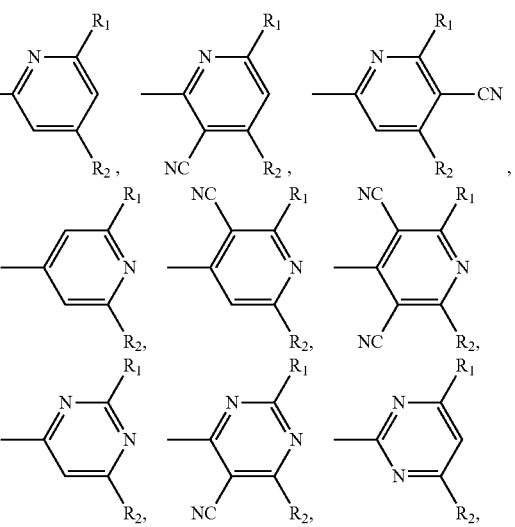

-continued
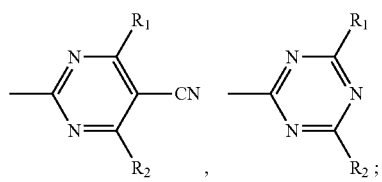
wherein $R_1$ and $R_2$ each independently represent substituted or unsubstituted aryl with 6 to 30 carbon atoms or substituted or unsubstituted heteroaryl with 5 to 30 carbon atoms; $R_1$ and $R_2$ are identical or different.
$R_1$ and $R_2$ each independently represent any one of:
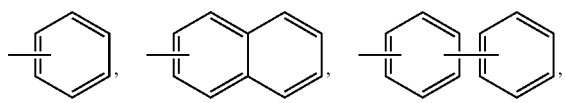
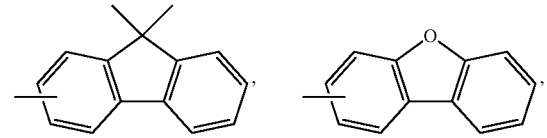
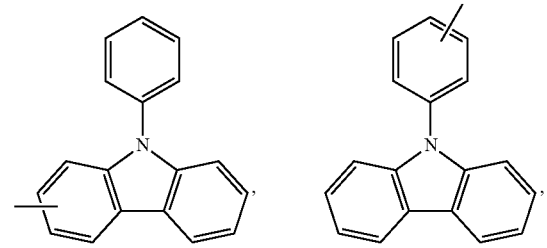
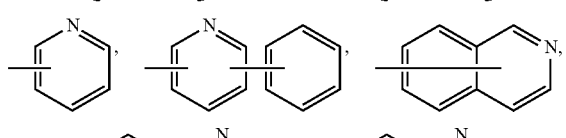
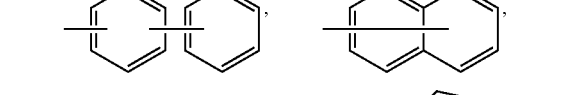
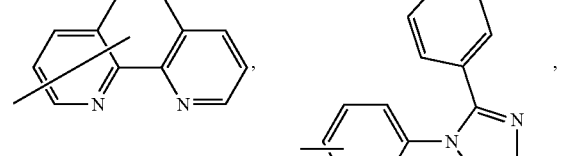
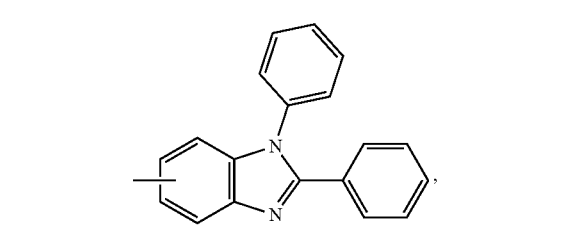
-continued
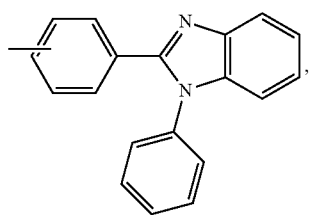
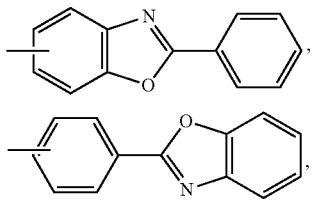
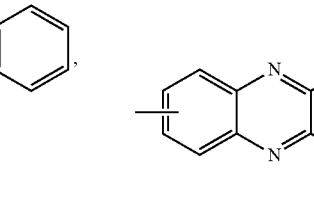
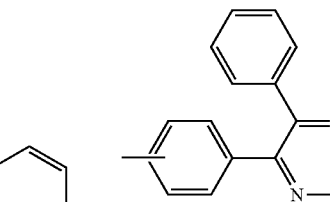
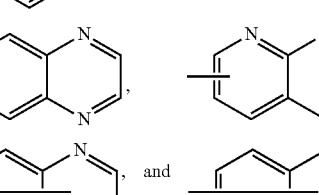
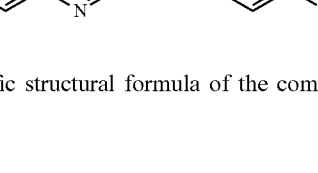
The specific structural formula of the compound is any one of:
(1)
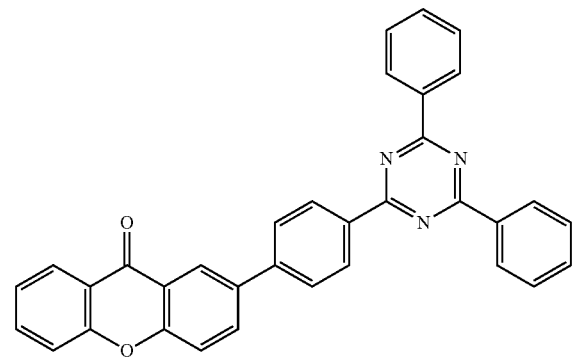

(2)
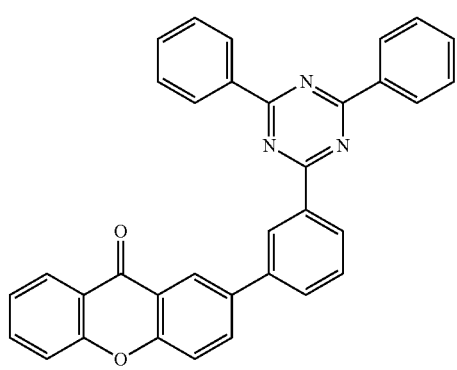
(3)
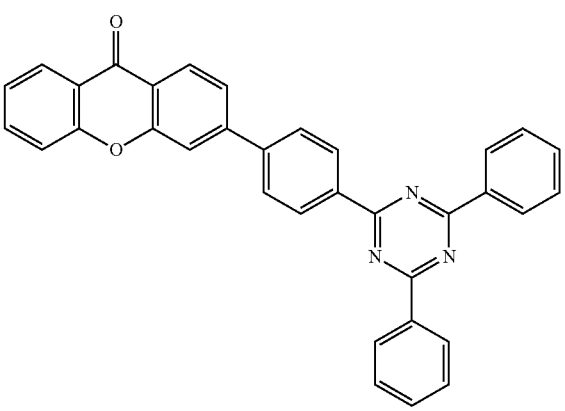
(4)
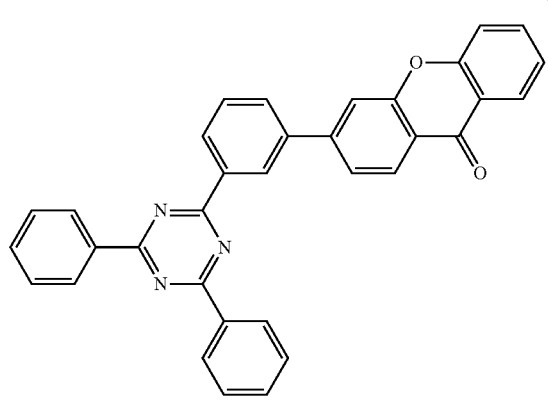
(5)
(6)
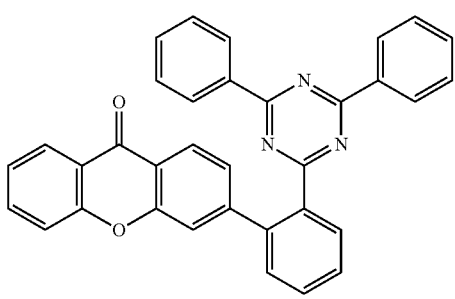
(7)
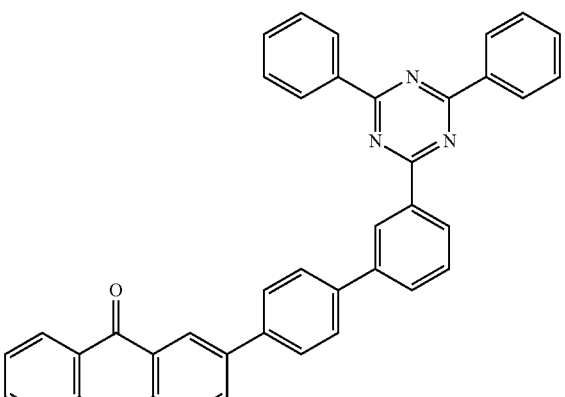
(8)
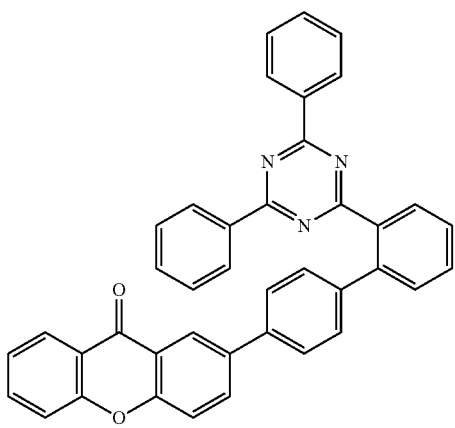
(9)

(10)
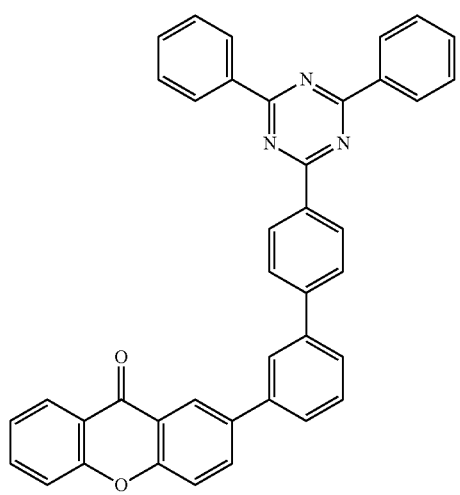
(11)
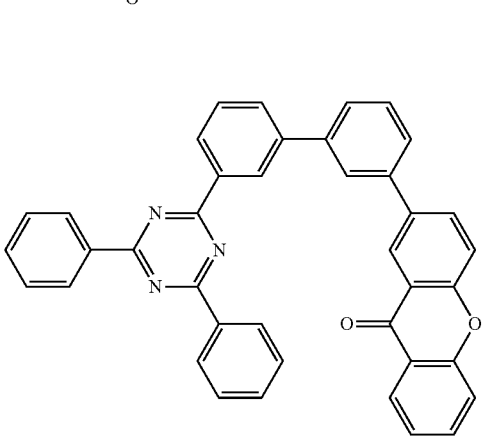
(12)
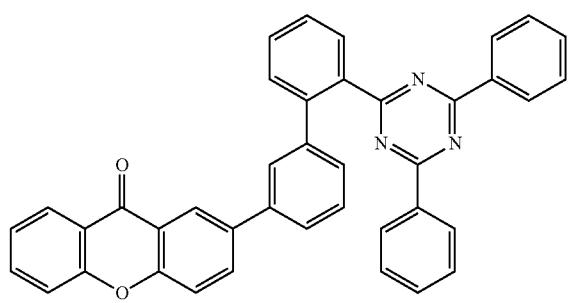
(13)
(14)
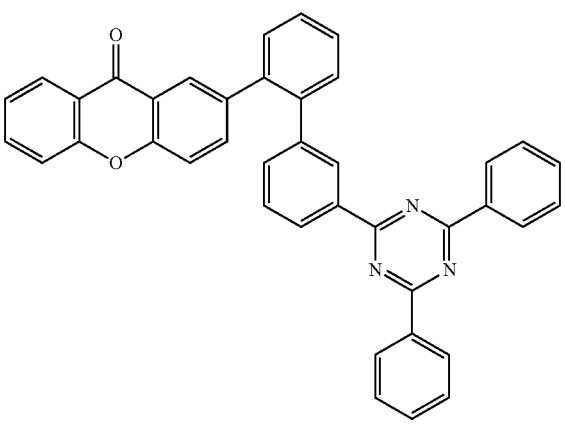
(15)
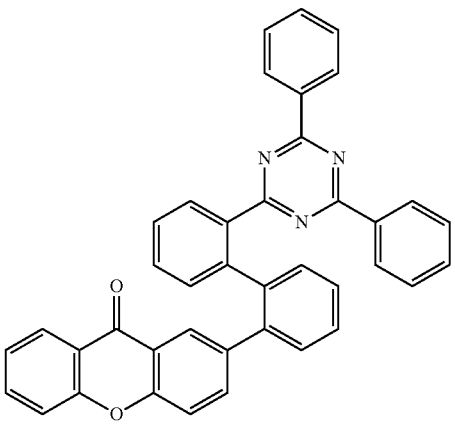
(16)
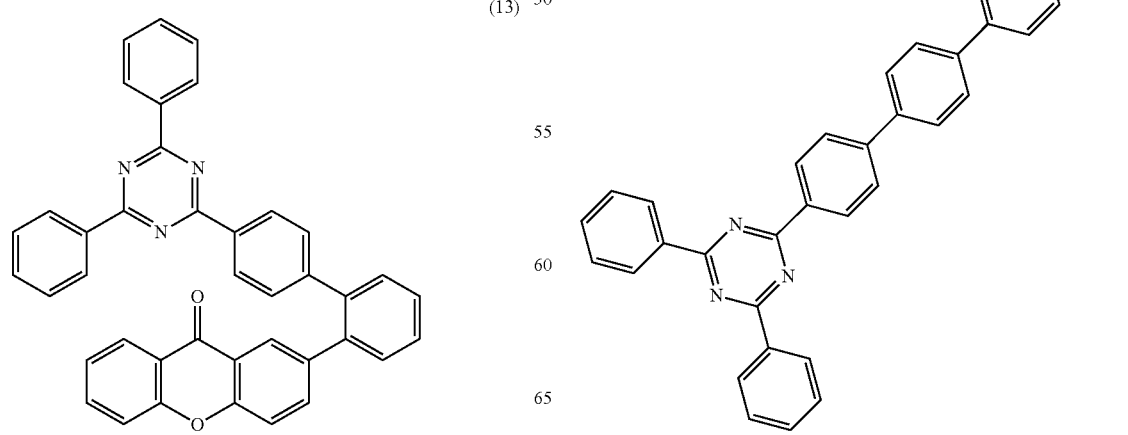

-continued
(17)
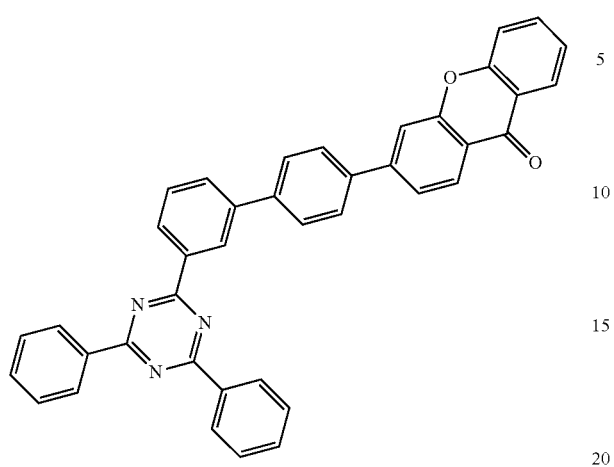
(18)
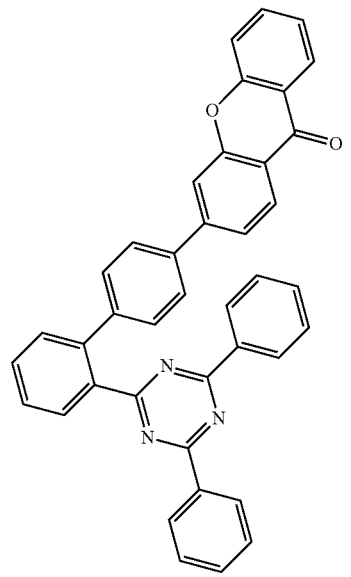
(19)
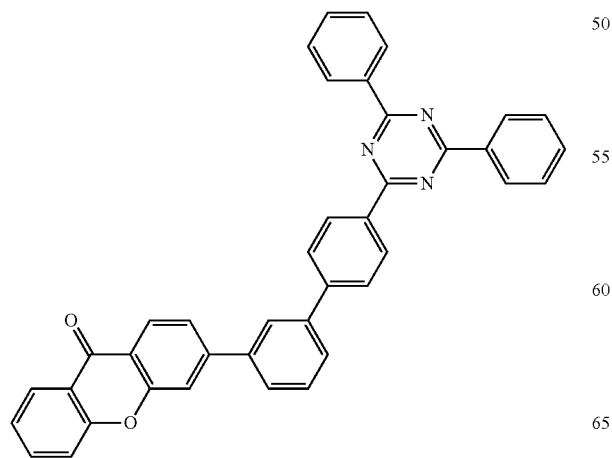
-continued
(20)
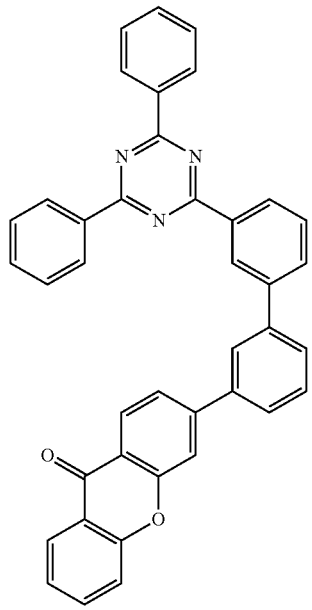
(21)
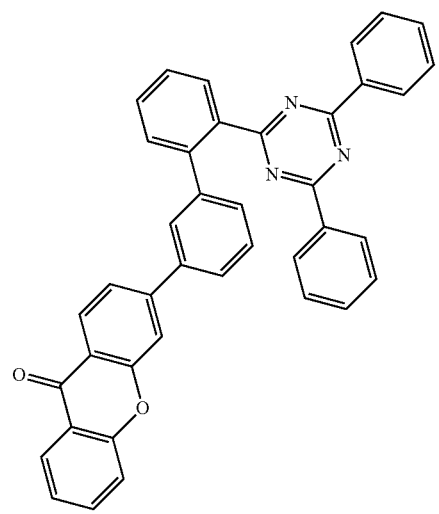
(22)
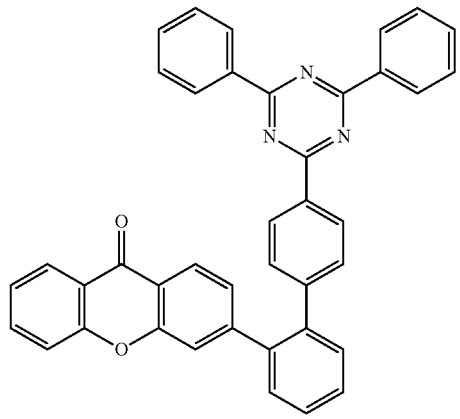

(23) 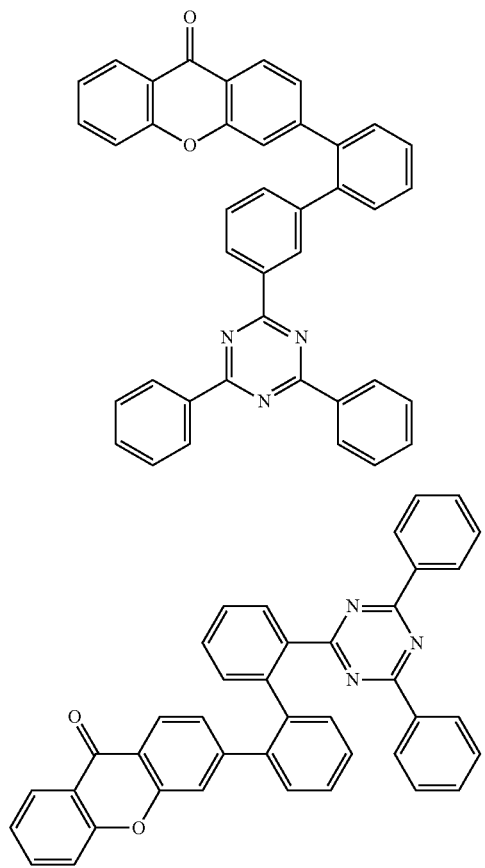
(24) 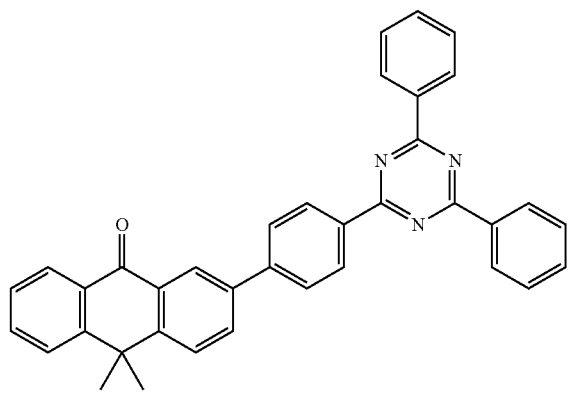
(25) 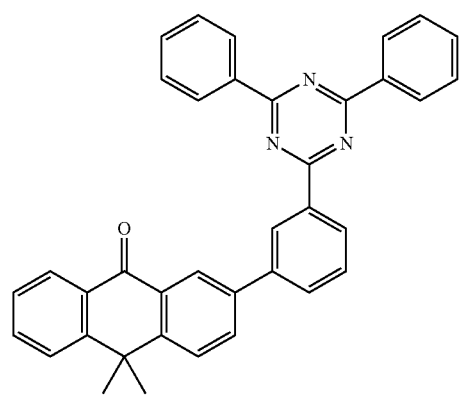
(26) 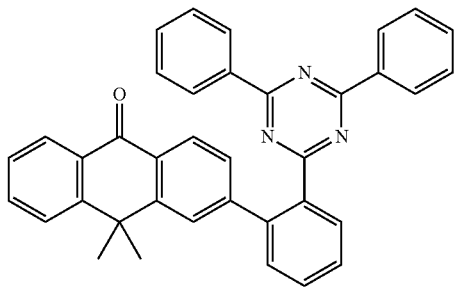
(27) 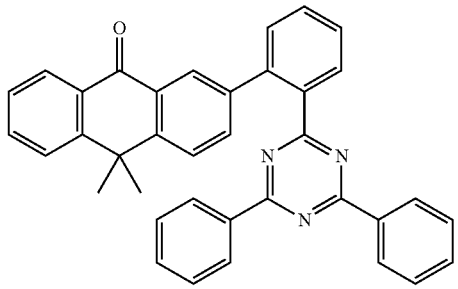
(28) 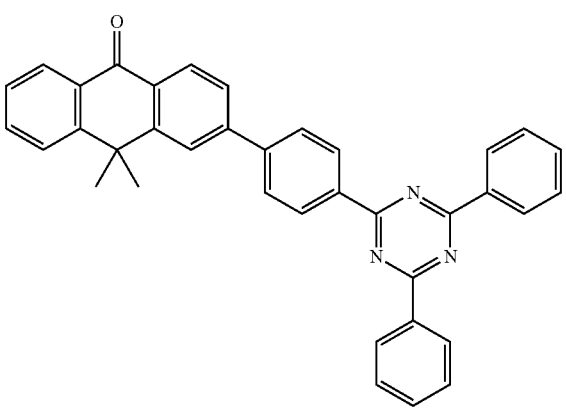
(29) 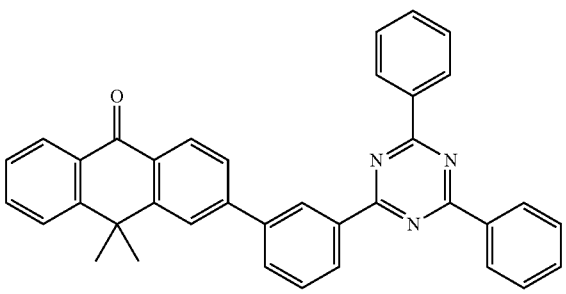
(30) 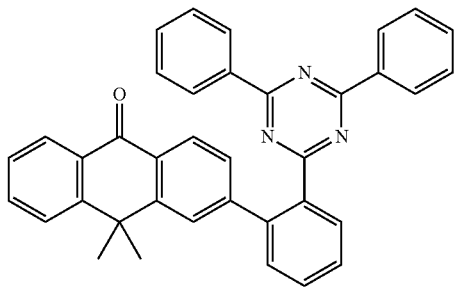

(31)
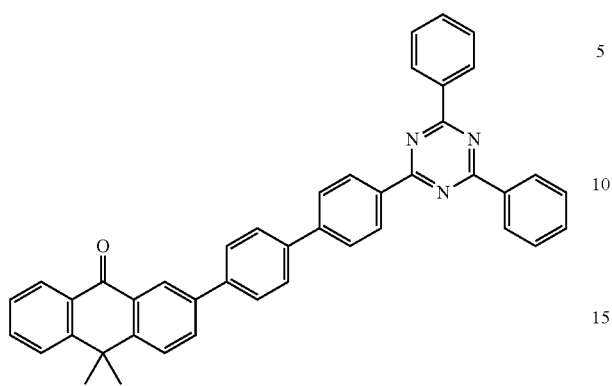
(32)
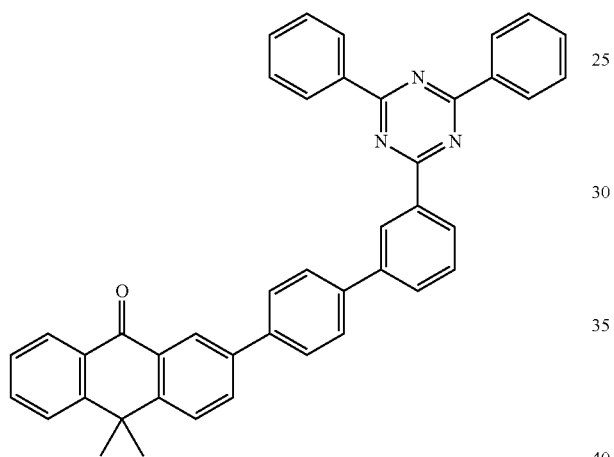
(33)
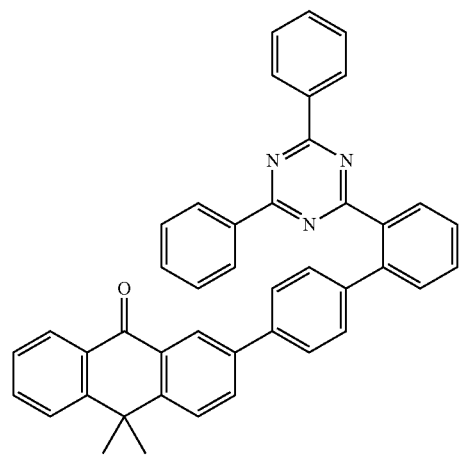
(34)
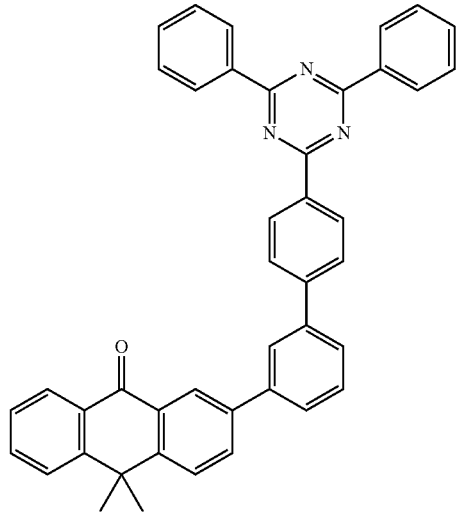
(35)
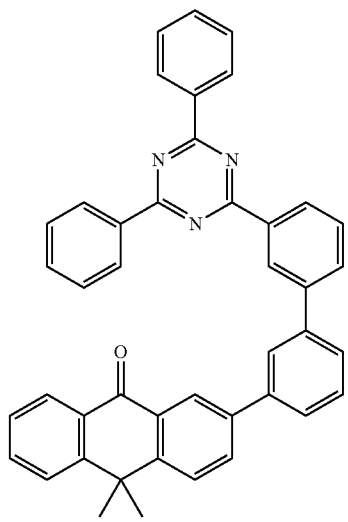
(36)
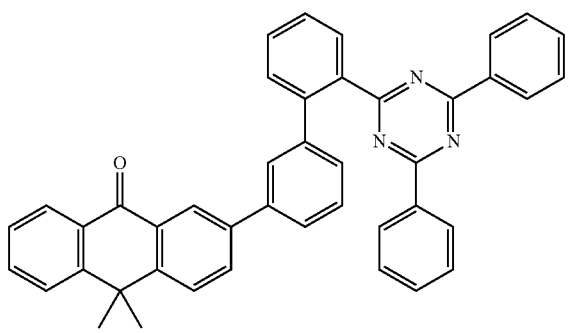

(37)
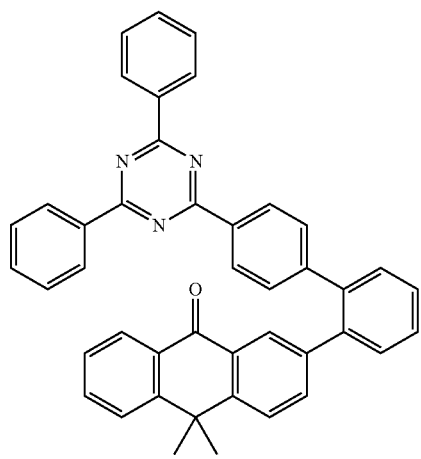
(40)
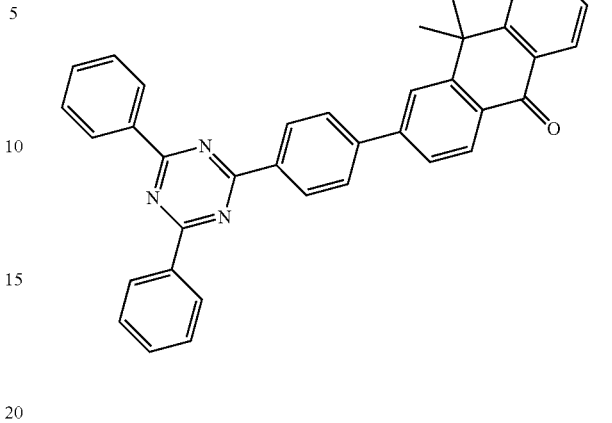
(38)
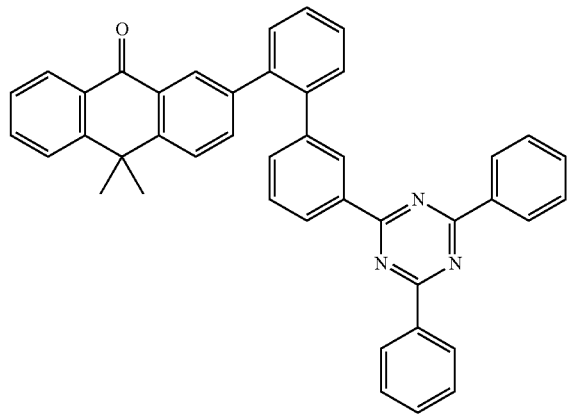
(41)
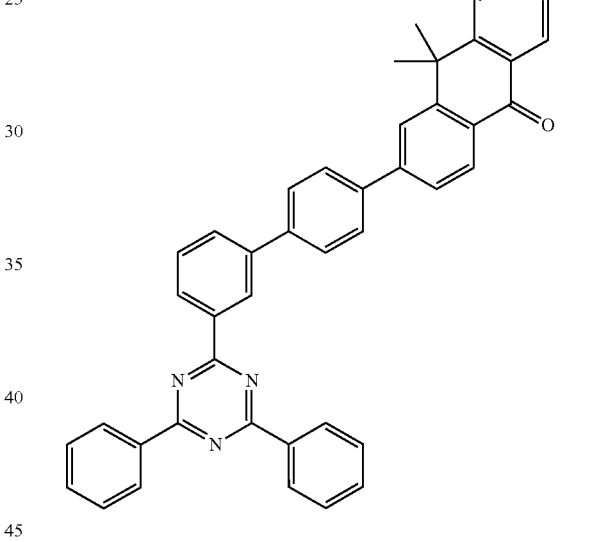
(39)
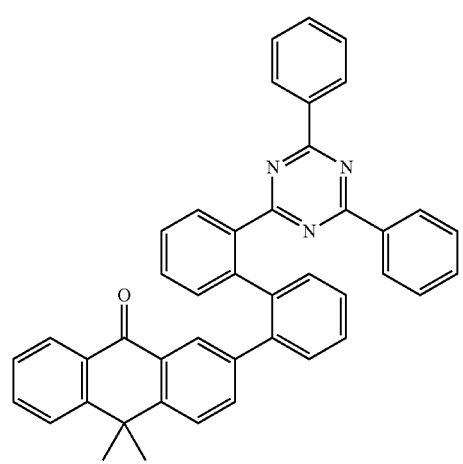
(42)
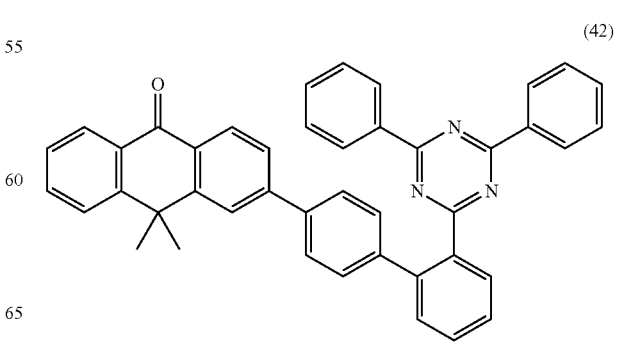

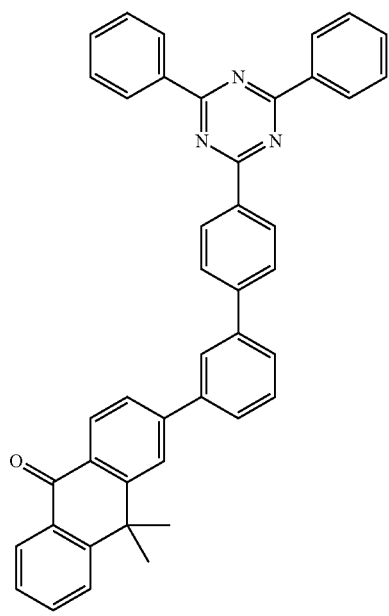
(43)
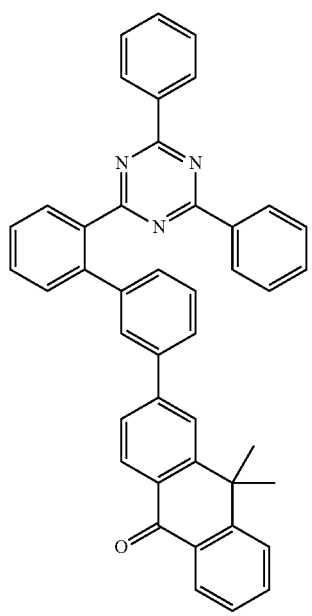
(45)
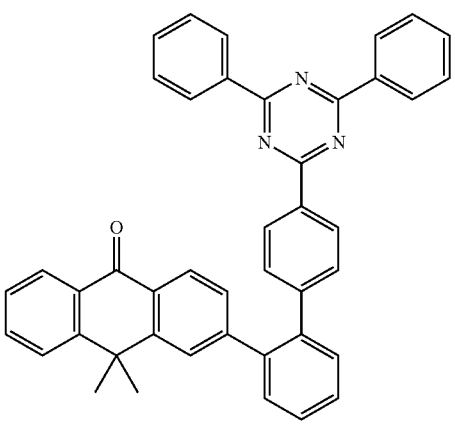
(46)
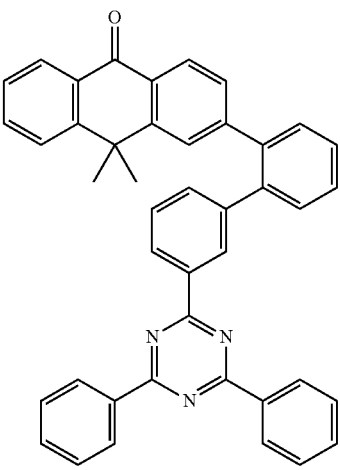
(44)
(47)

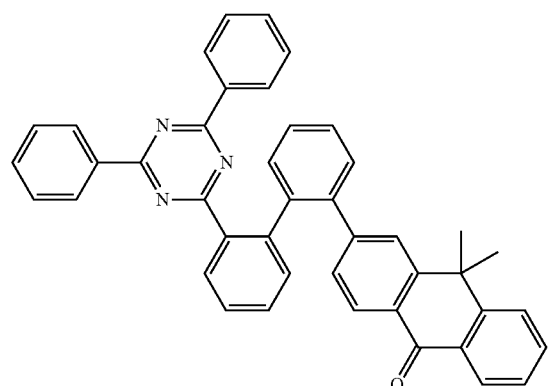
(48)
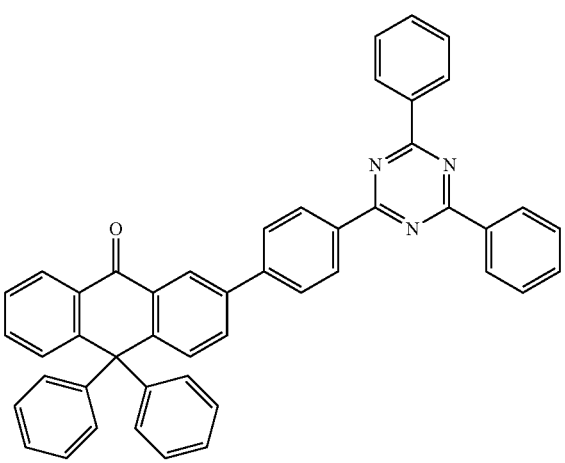
(52)
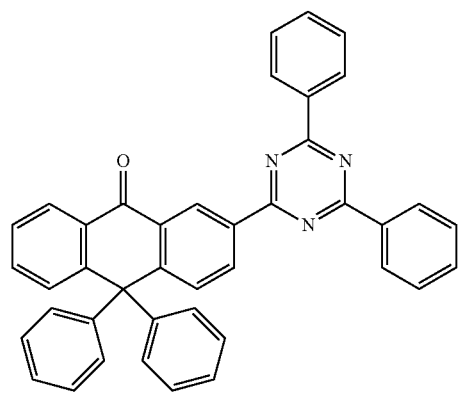
(49)
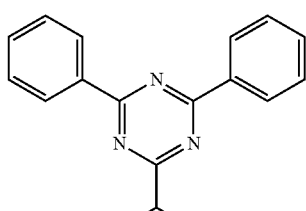
(53)
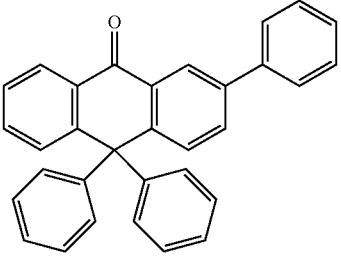
(50)
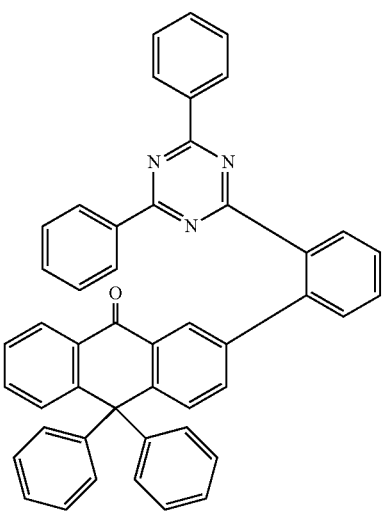
(54)
(51)

(55)
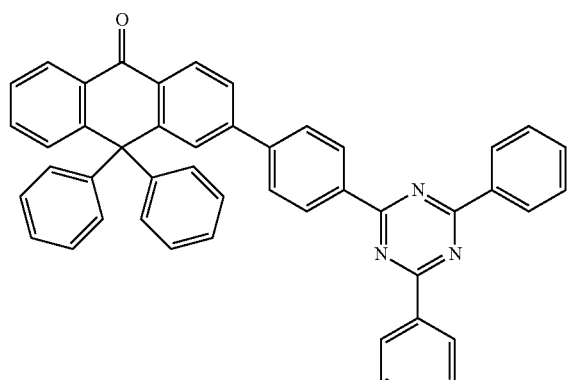
(56)
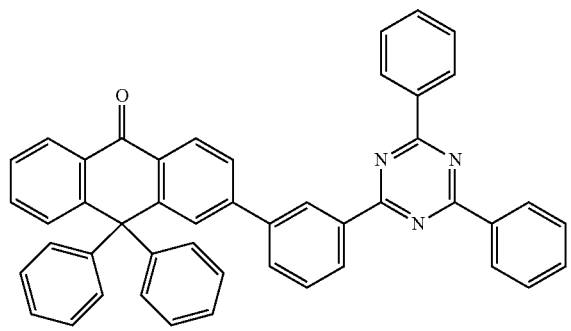
(57)
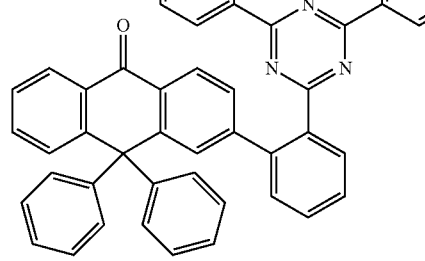
(58)
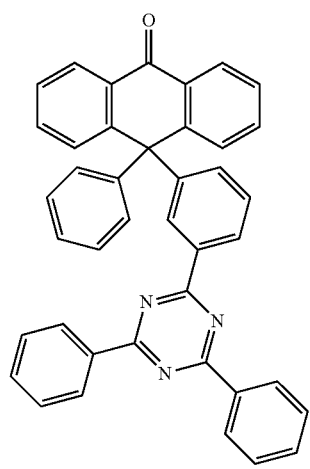
(59)
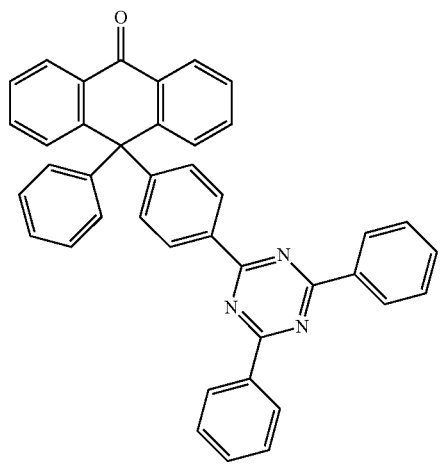
(60)
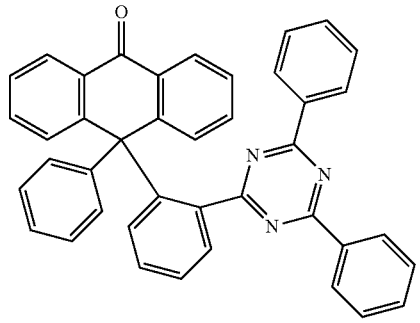
(61)
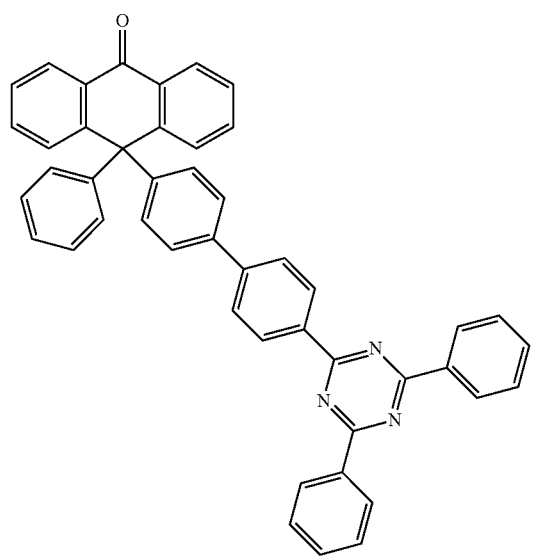

-continued
(62)
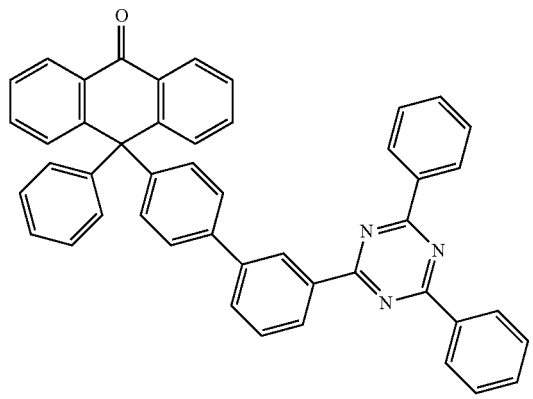
(63)
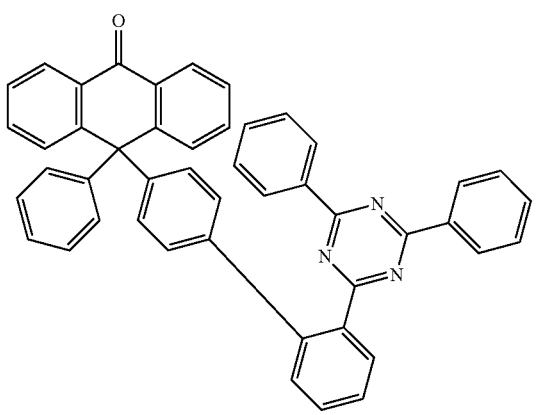
(64)
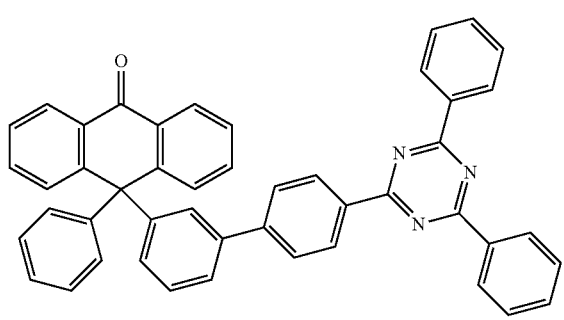
(65)
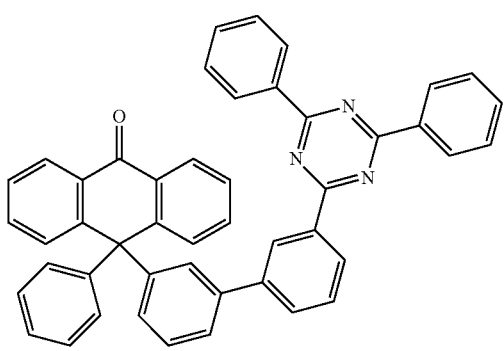
-continued
(66)
(67)
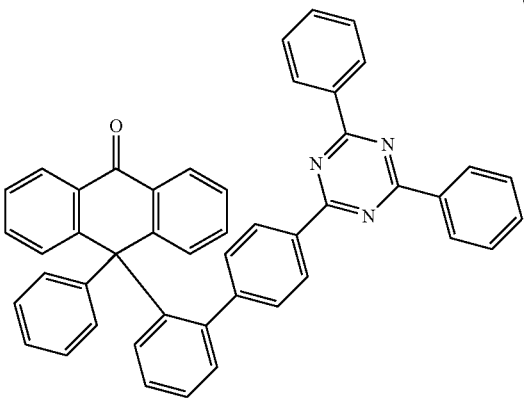
(68)
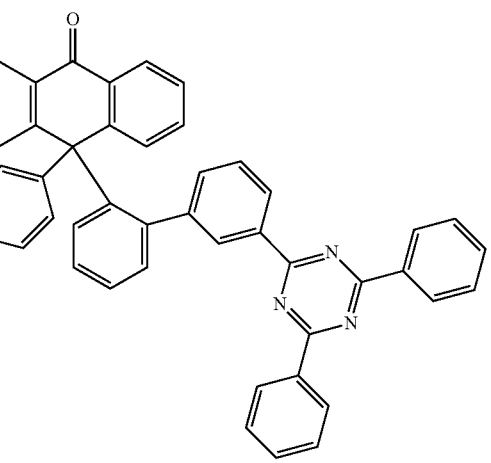

(69)
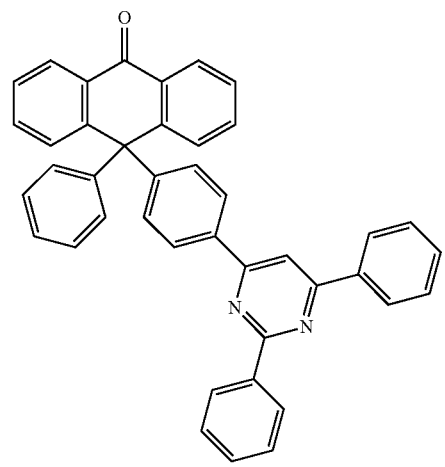
(70)
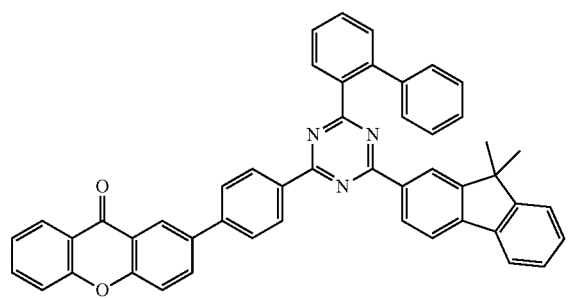
(71)
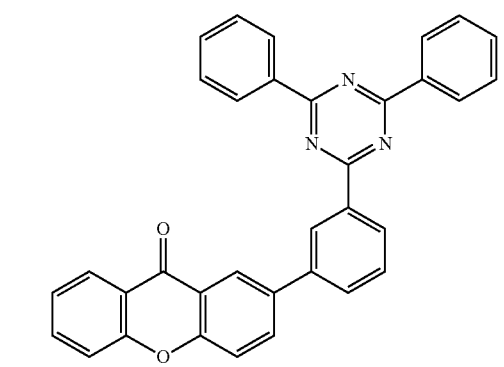
(72)
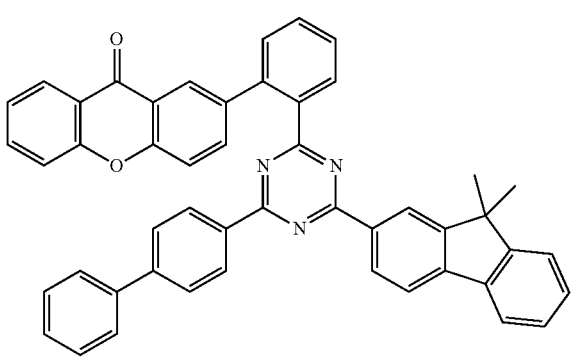
(73)
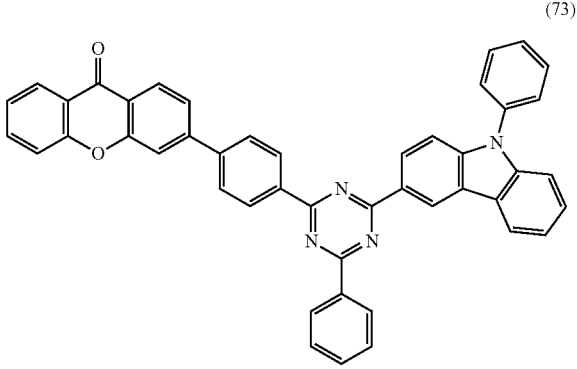
(74)
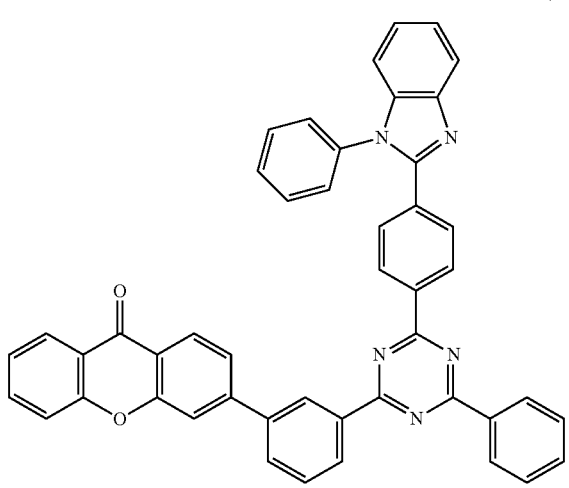
(75)
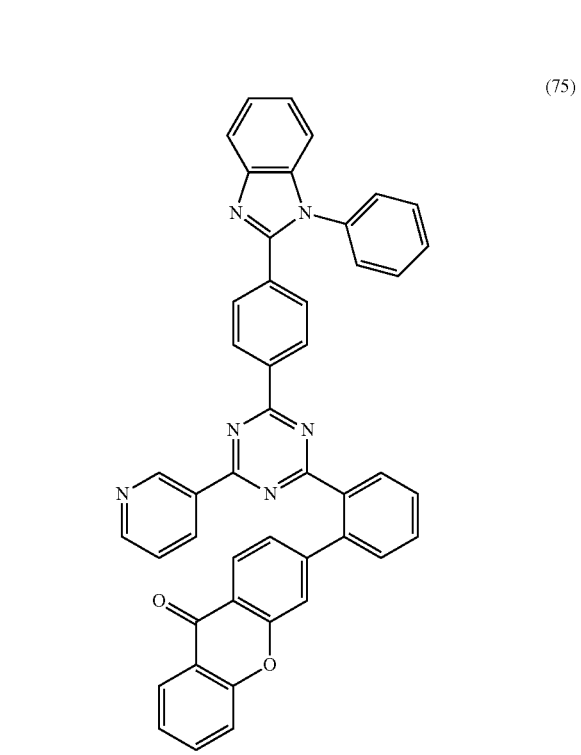

-continued
(76)
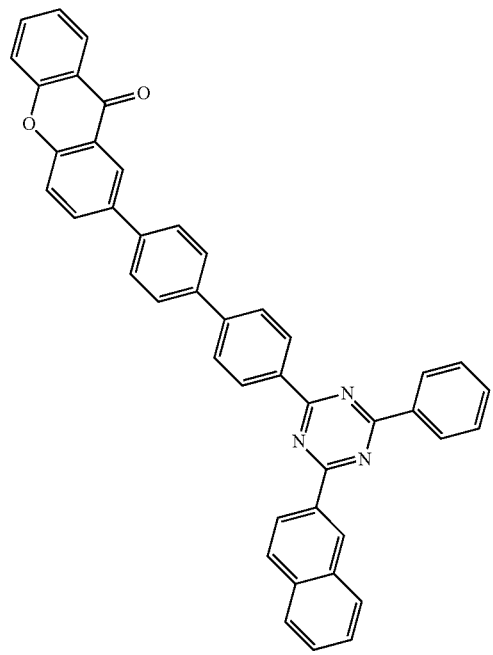
(79)
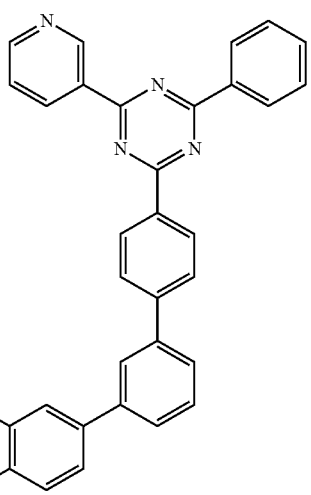
(77)
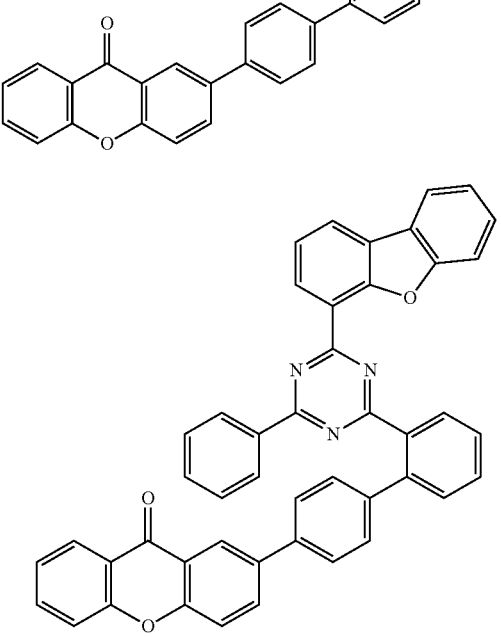
(80)
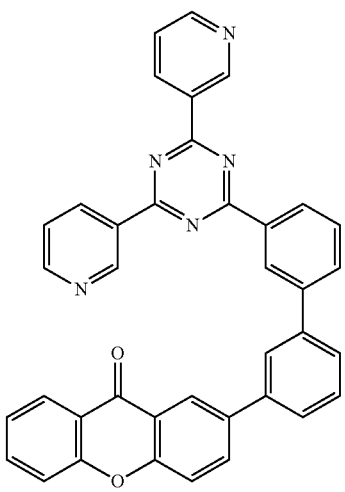
(78)
(81)
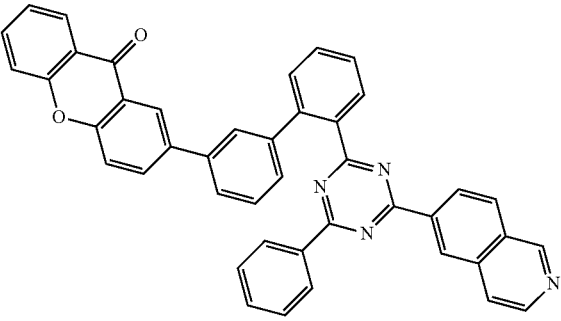

-continued
(82)
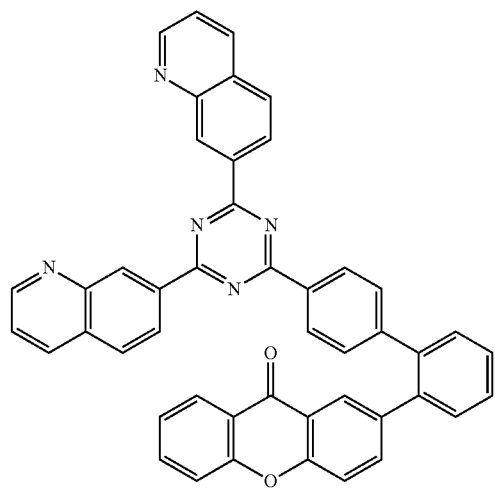
(83)
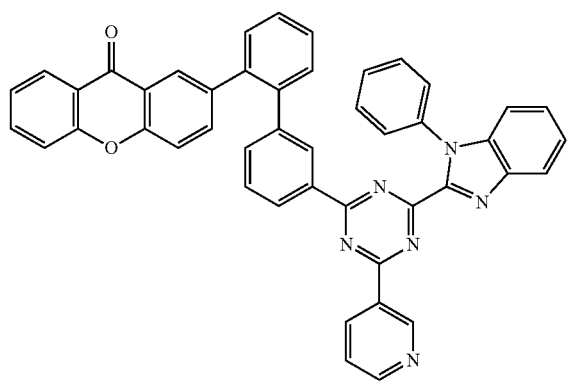
(84)
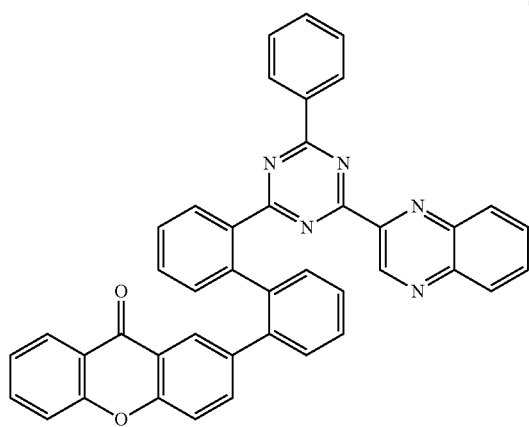
-continued
(85)
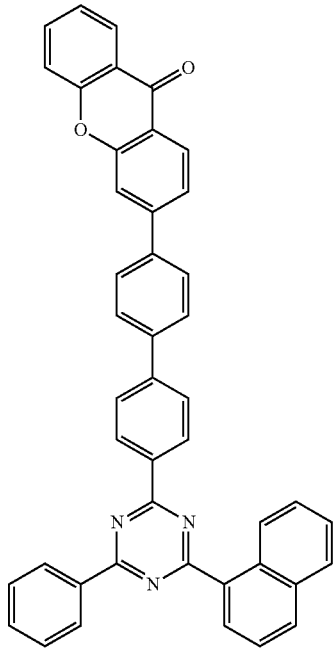
(86)
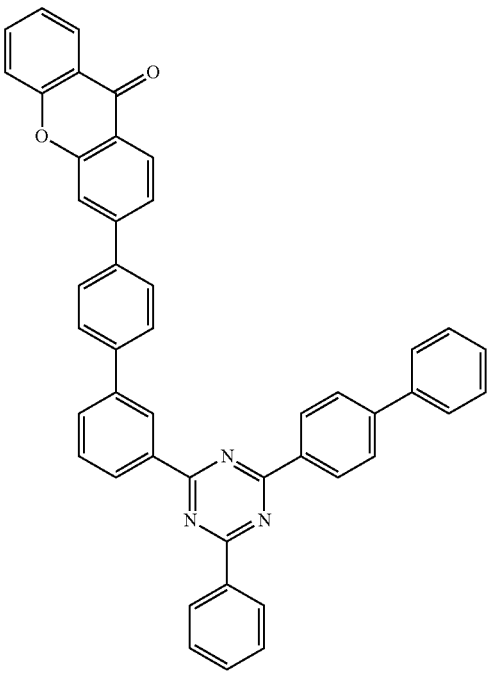

(87)
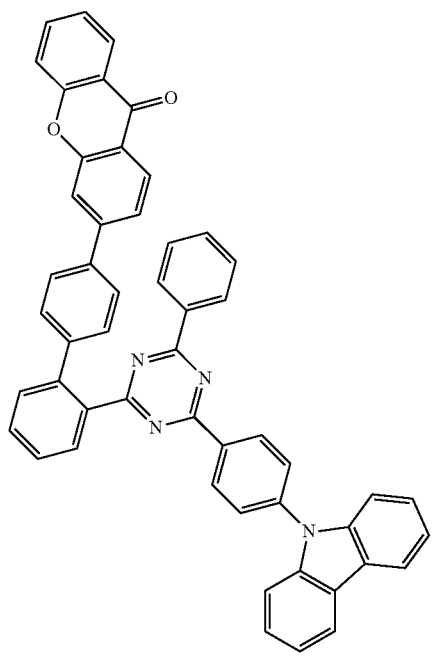
(88)
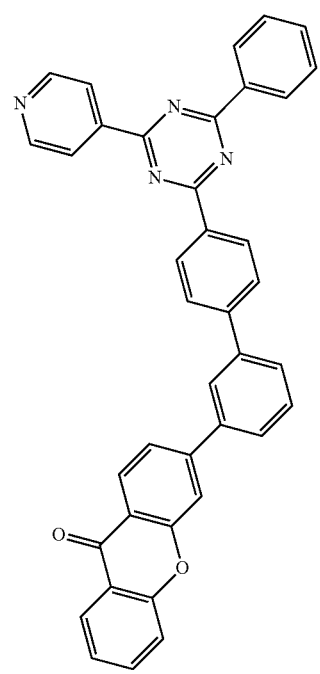
(89)
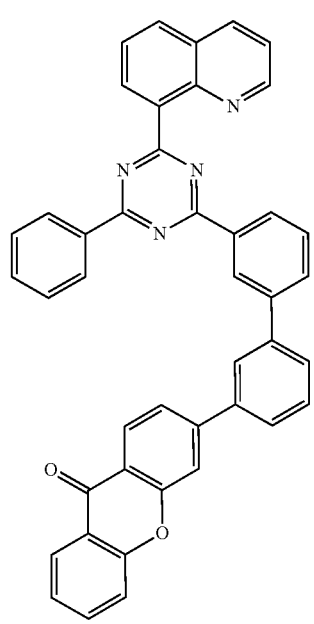
(90)
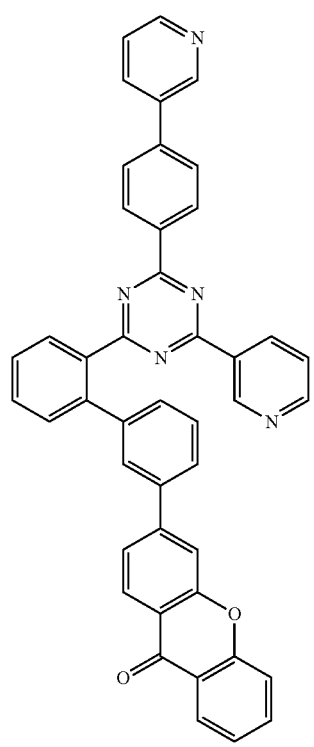

-continued
(91)
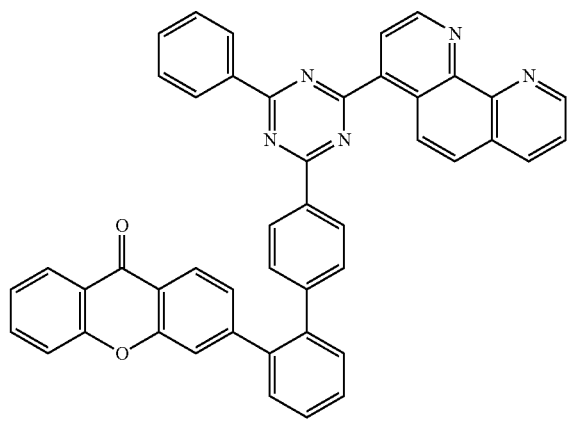
(92)
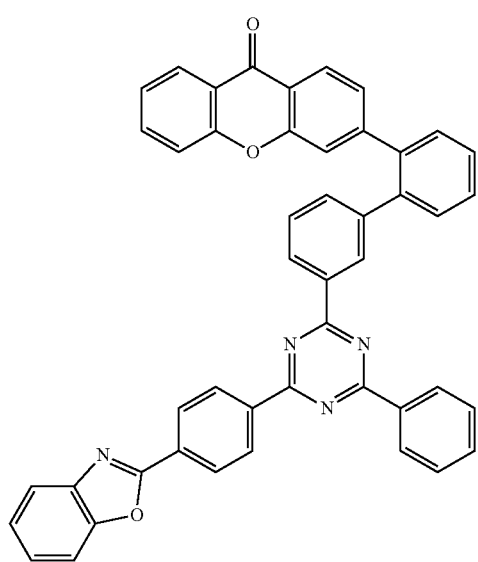
(93)
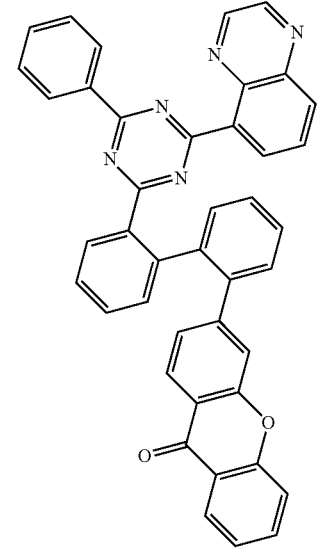
-continued
(94)
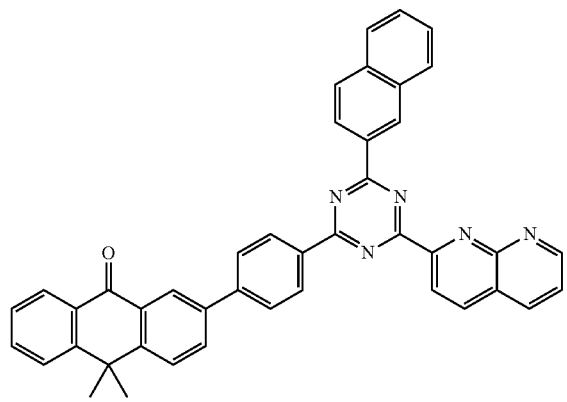
(95)
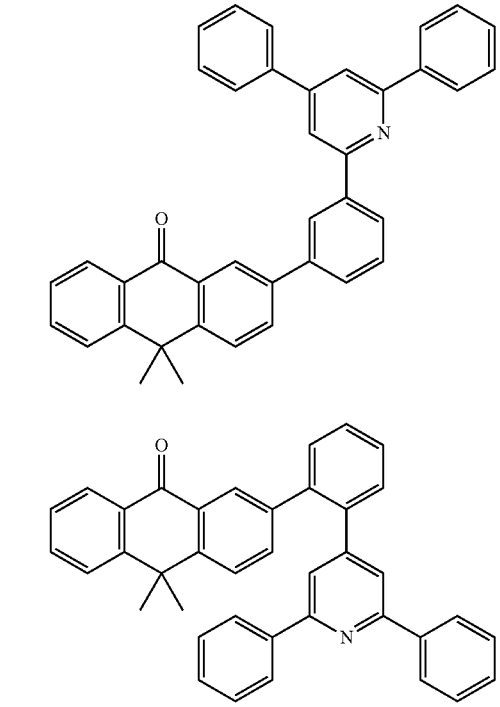
(96)
(97)
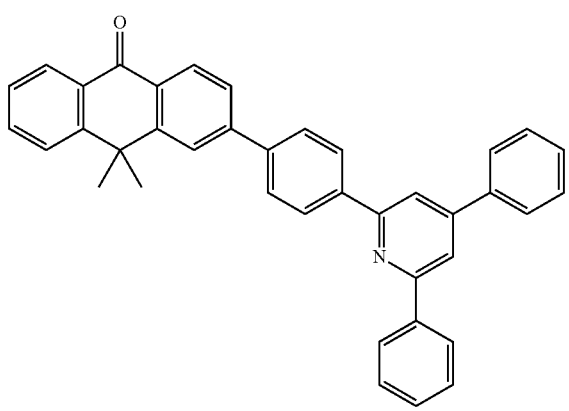

(98)
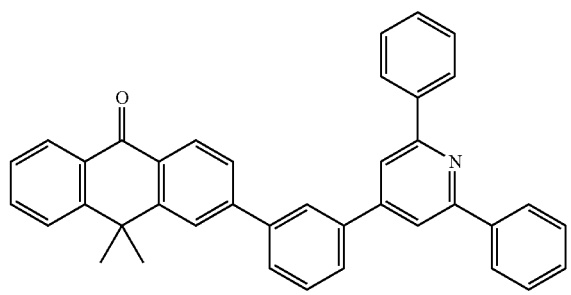
(99)
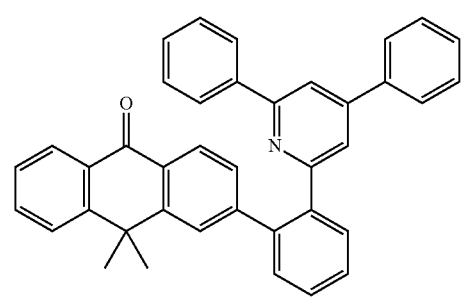
(100)
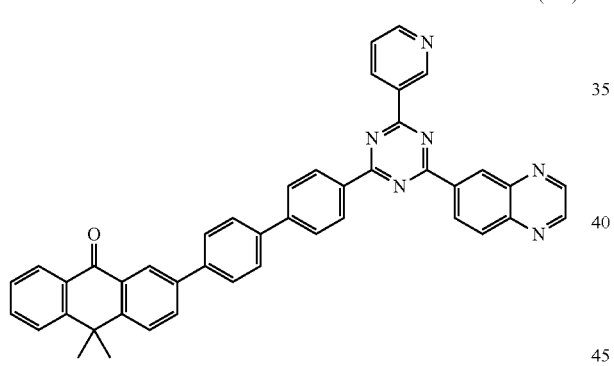
(101)
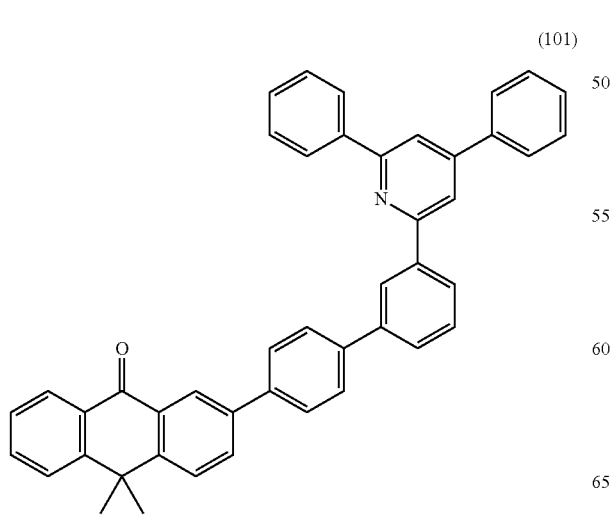
(102)
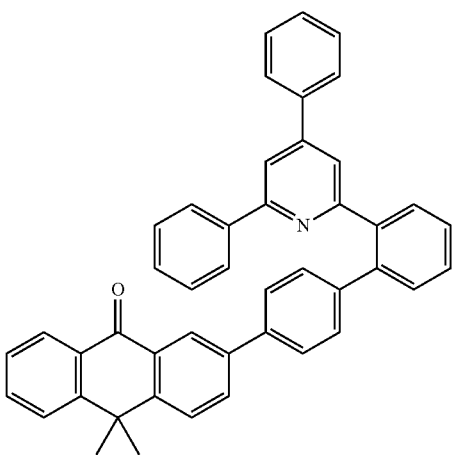
(103)
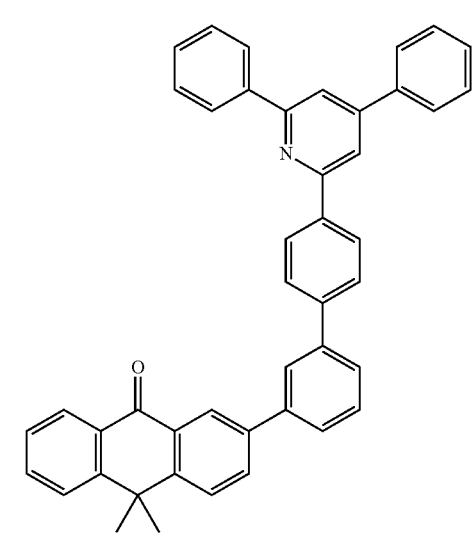
(104)
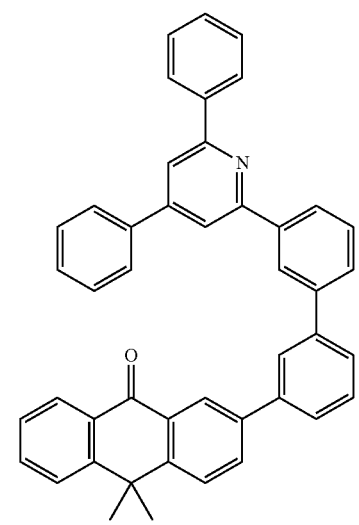

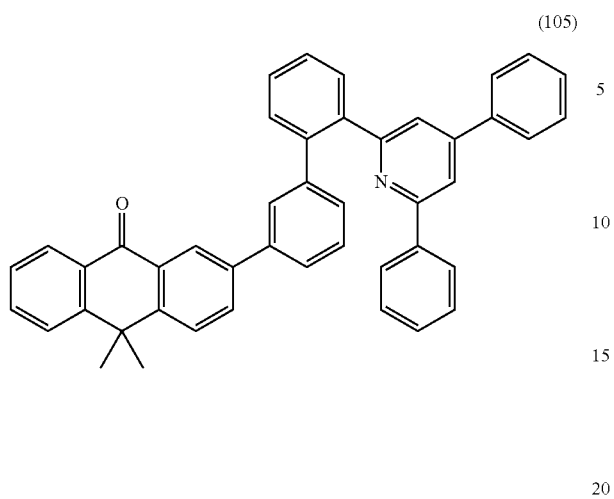
(105)
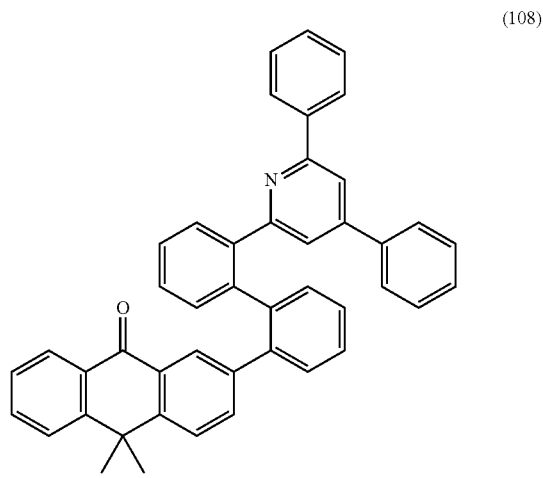
(108)
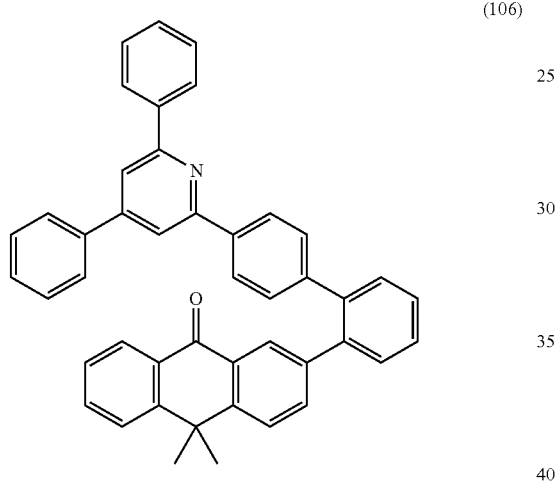
(106)
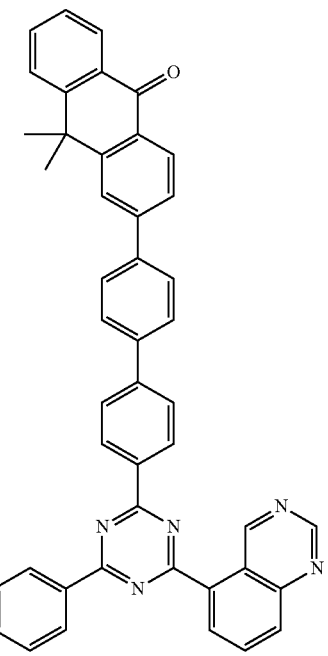
(109)
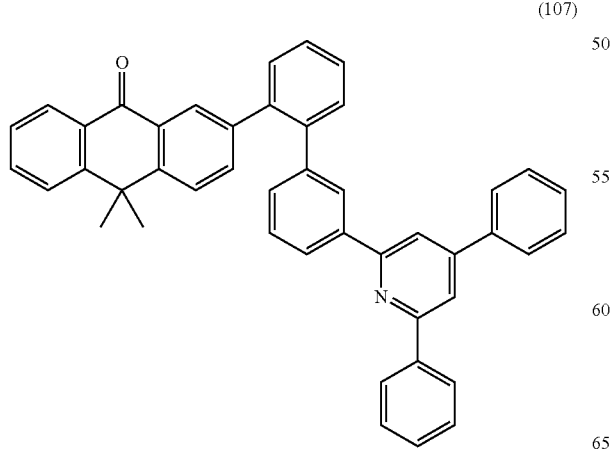
(107)

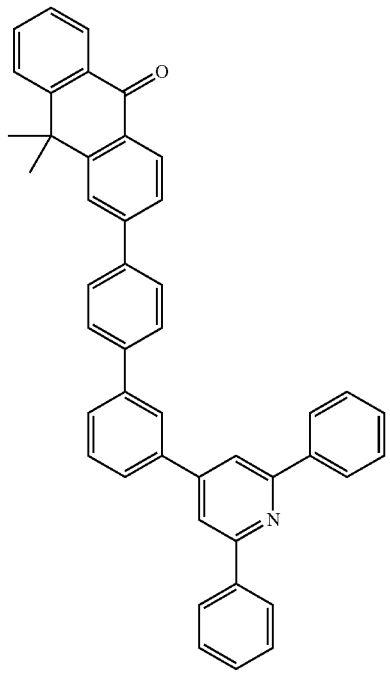
(110)
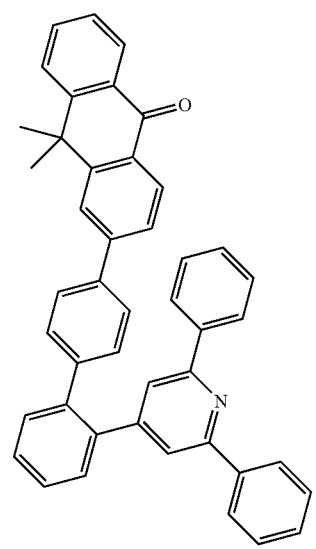
(111)
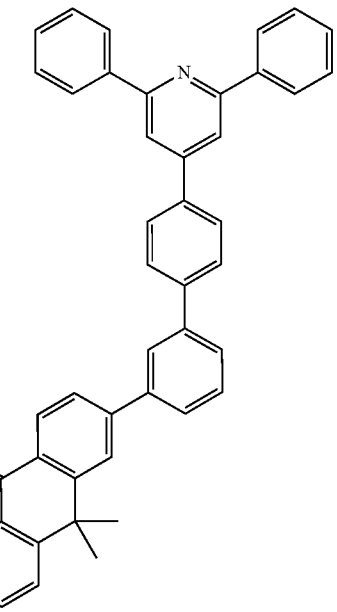
(112)
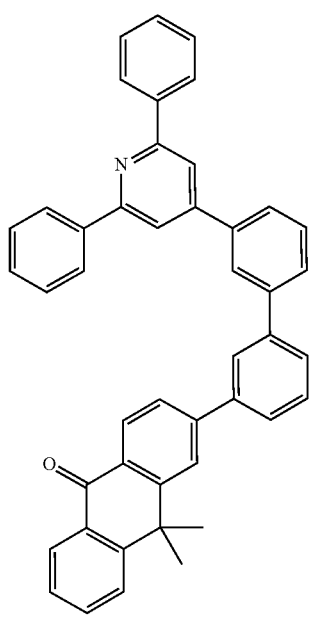
(113)

-continued
(114)
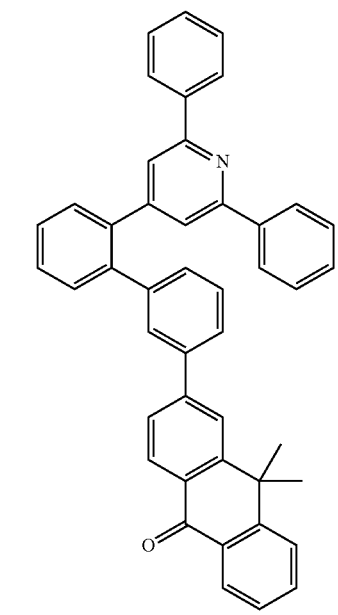
(115)
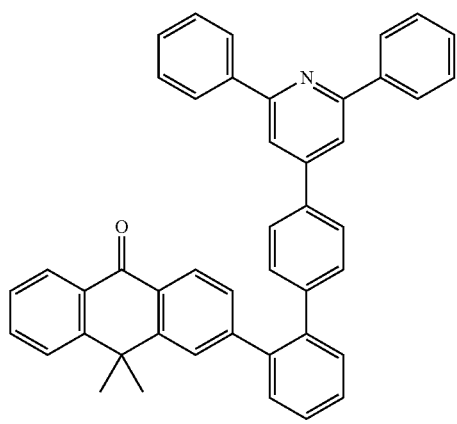
(116)
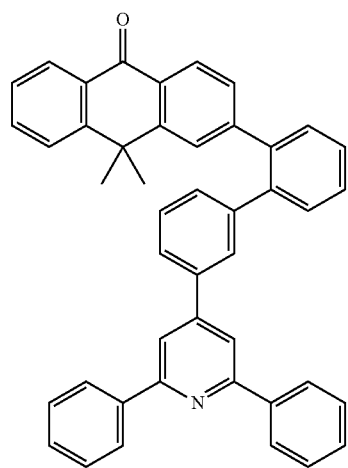
-continued
(117)
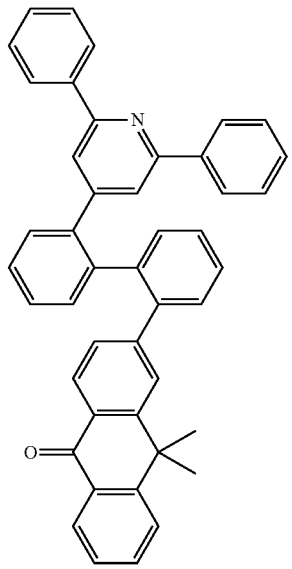
(118)
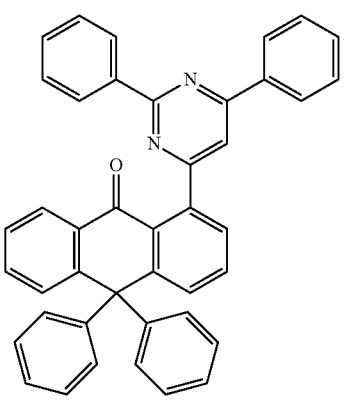
(119)
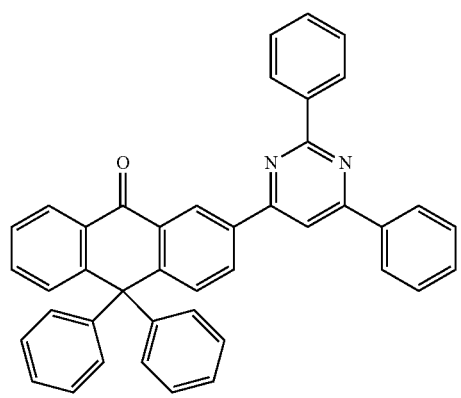

(120)
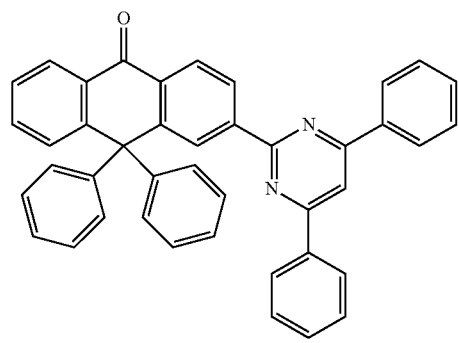
(121)
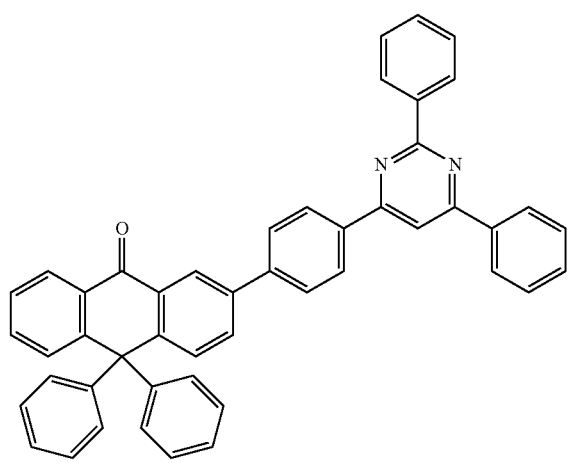
(122)
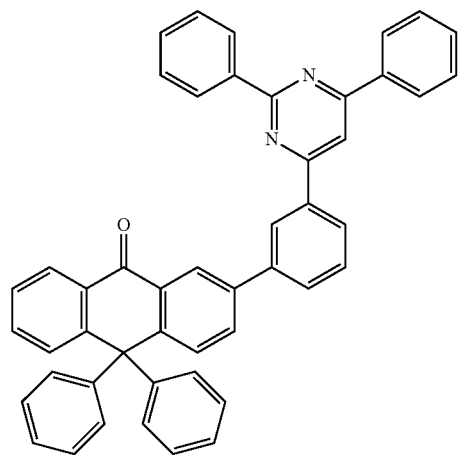
(123)
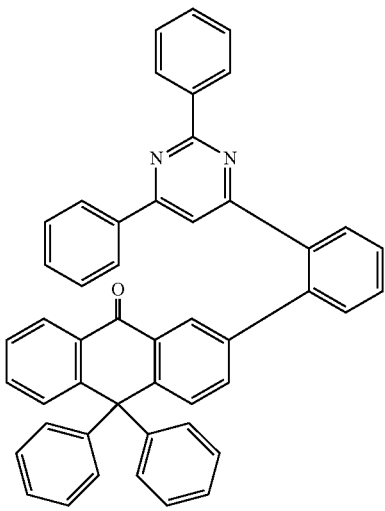
(124)
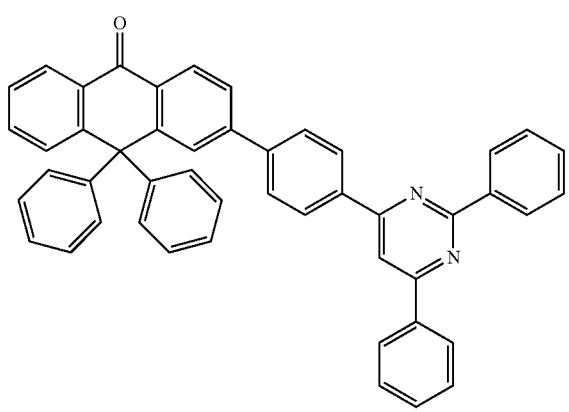
(125)
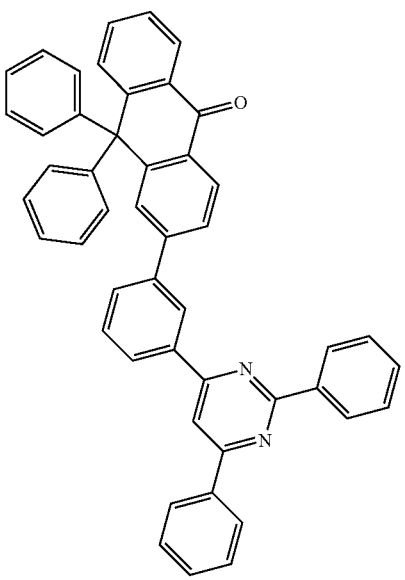

(126)
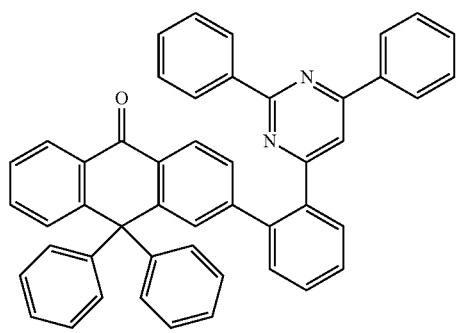
(127)
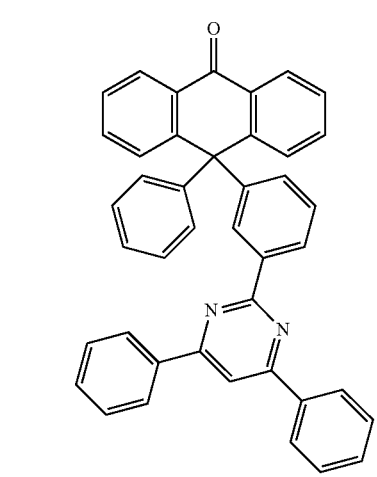
(128)
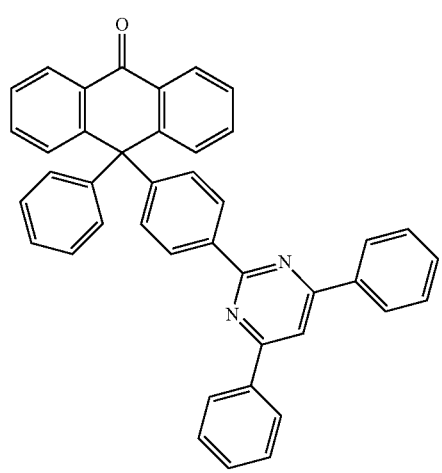
(129)
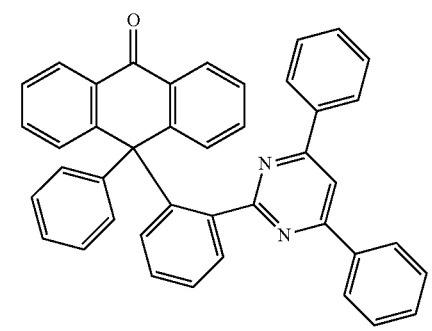
(130)
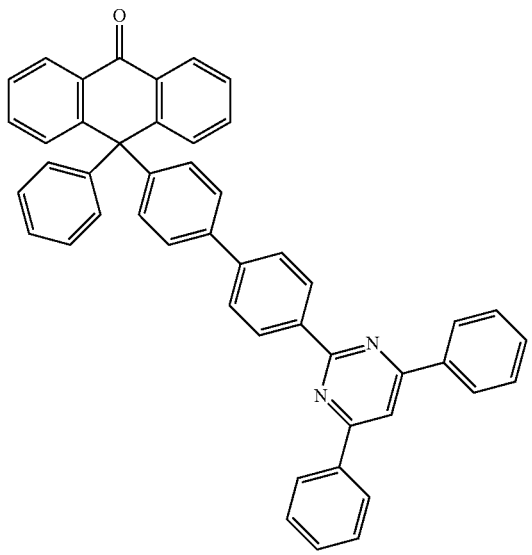
(131)
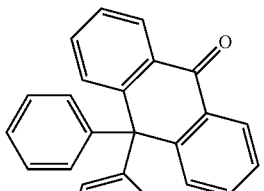
(132)
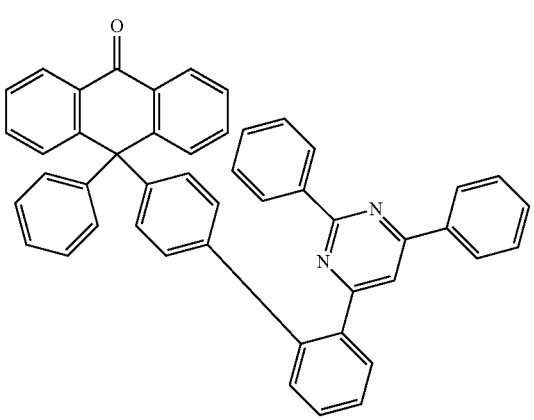

(133)
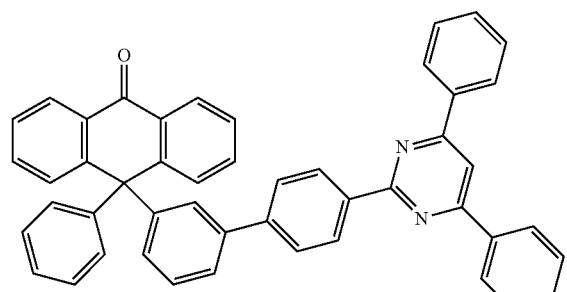
(134)
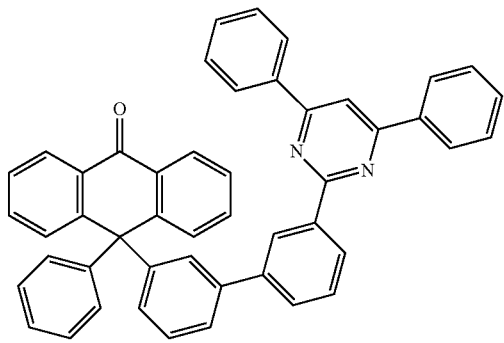
(135)
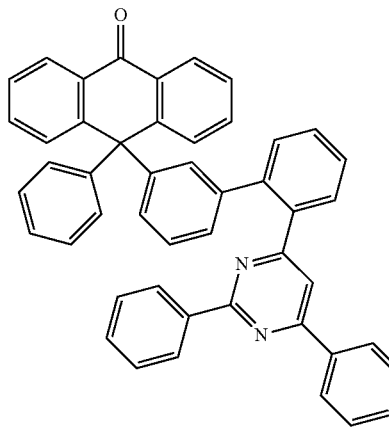
(136)
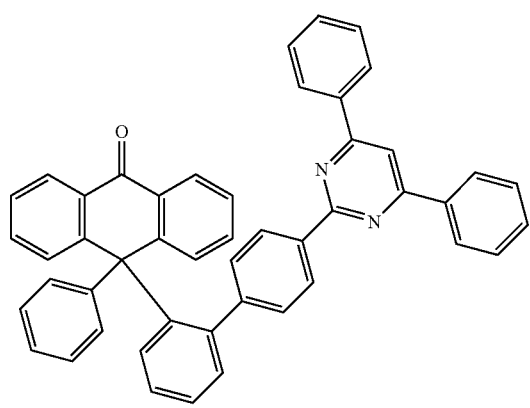
(137)
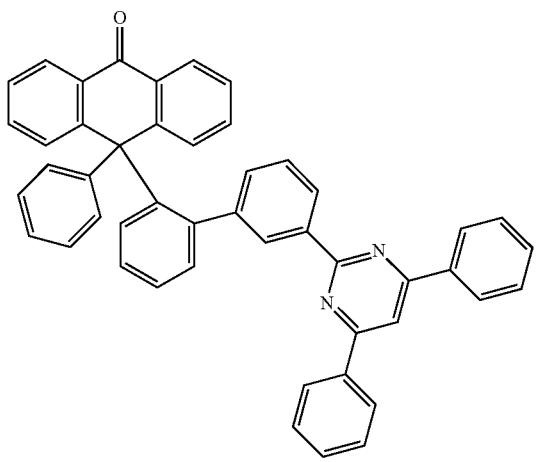
(138)
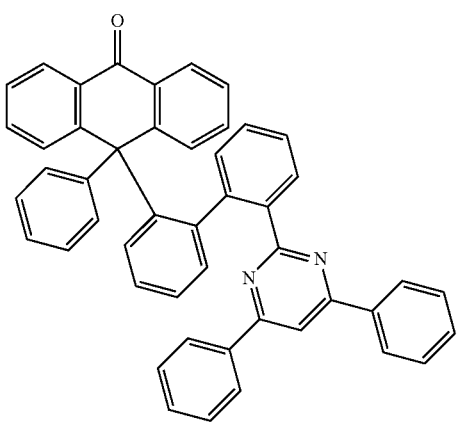
(139)
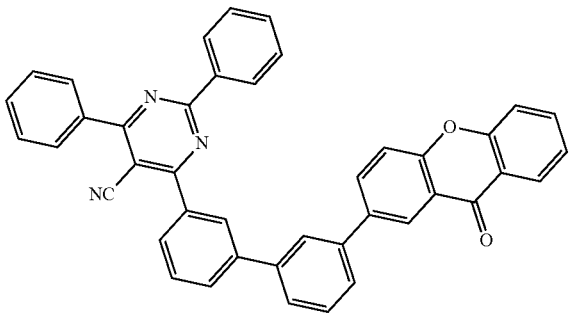
(140)
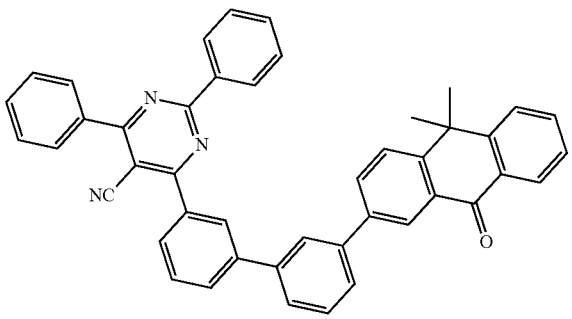

(141)
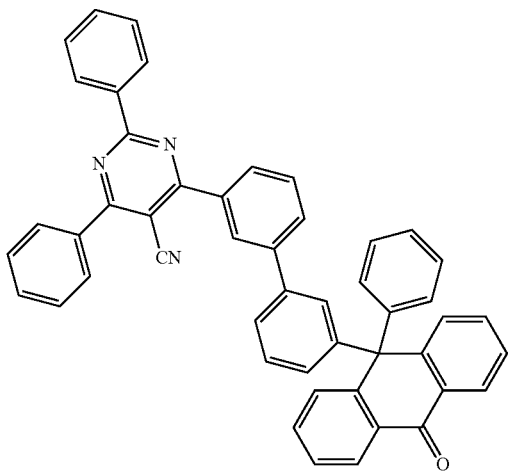
(142)
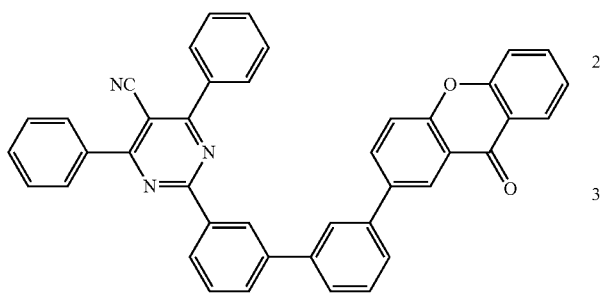
(143)
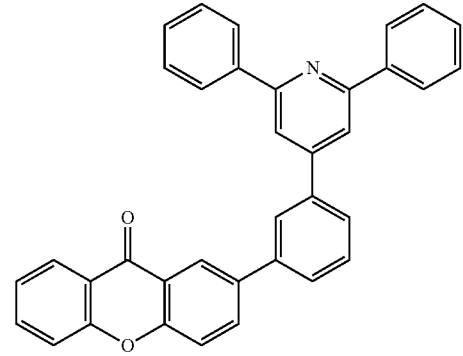
(144)
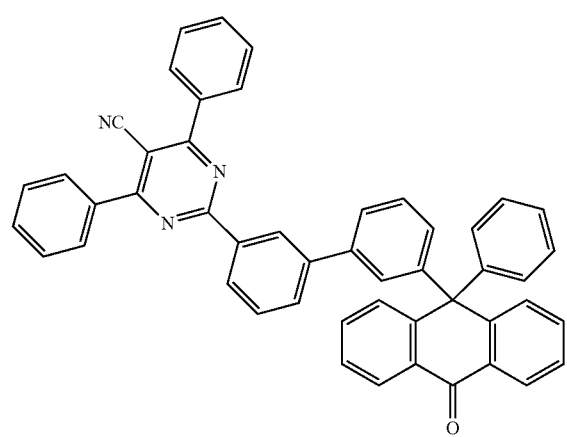
(145)
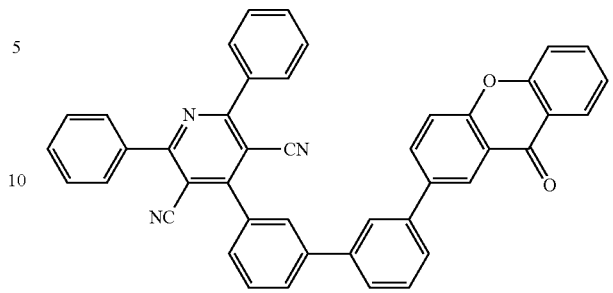
(146)
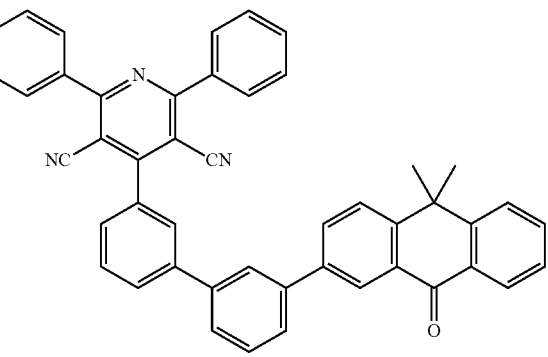
(147)
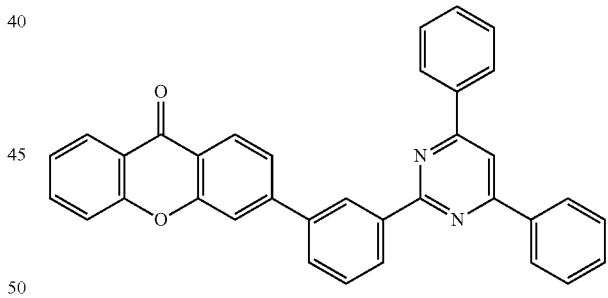
(148)
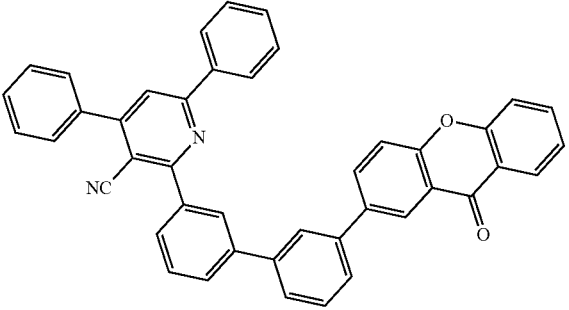

(149)
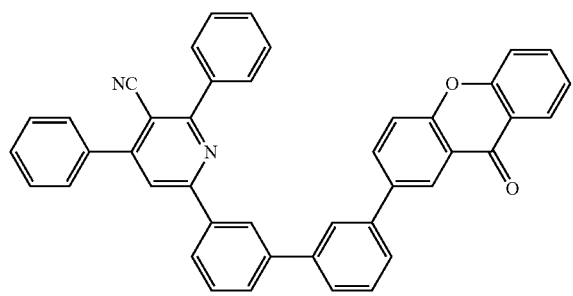
(150)
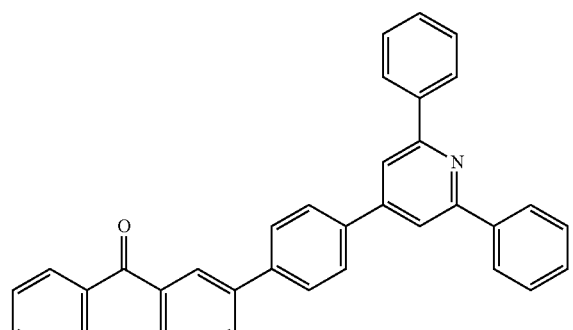
(151)
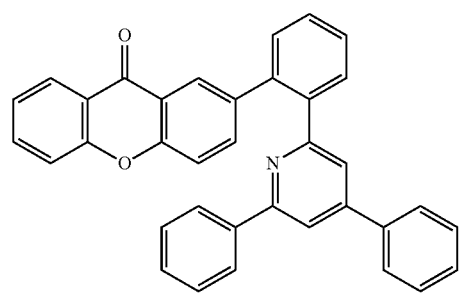
(152)
(153)
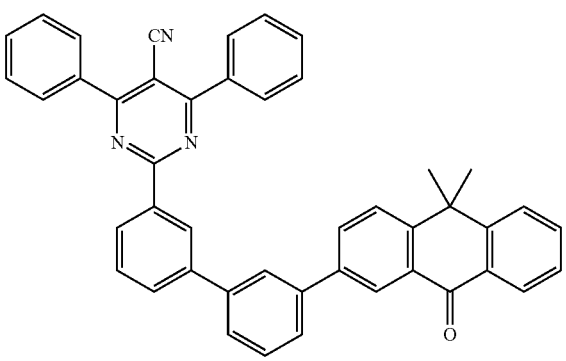
(154)
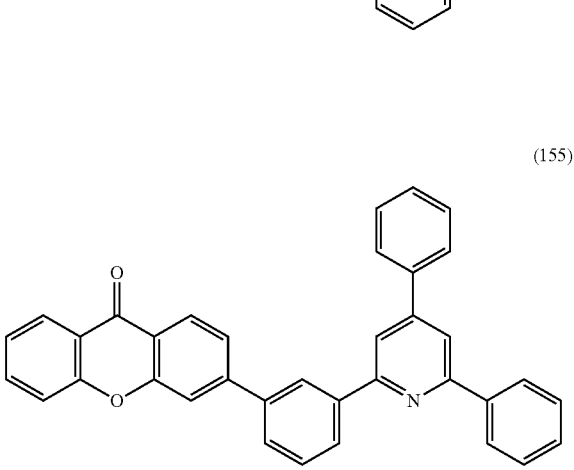
(155)
(156)
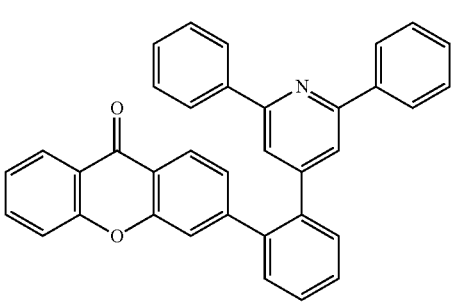

(157)
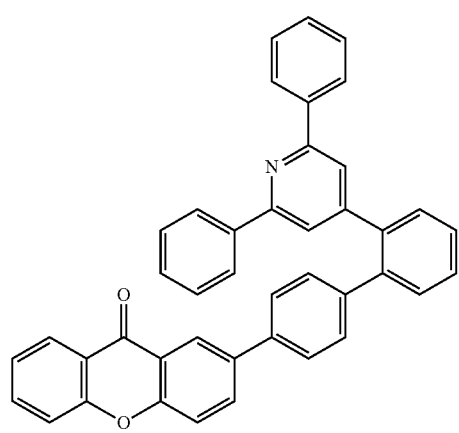
(158)
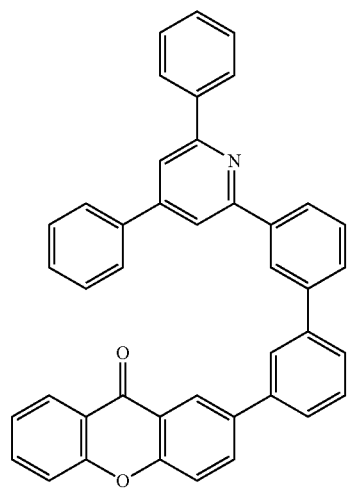
(159)
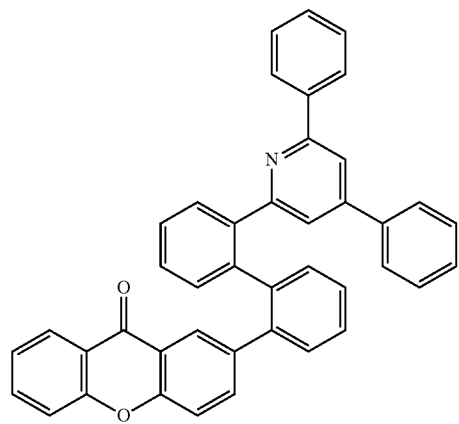
(160)
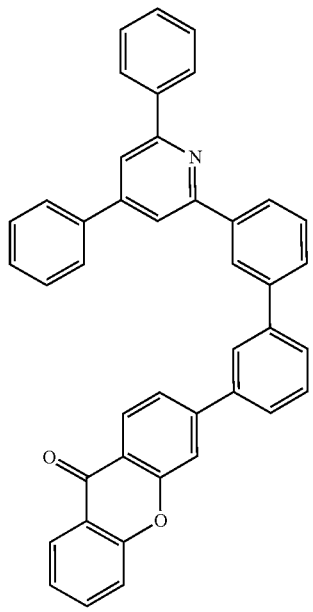
(161)
(162)
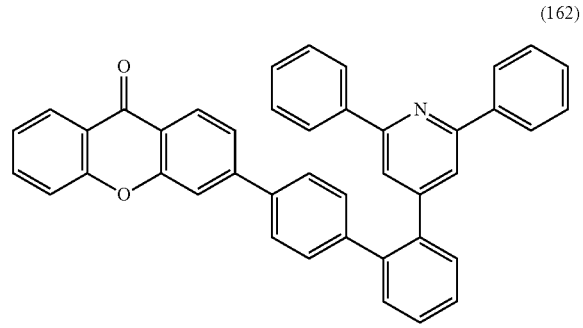

(163)
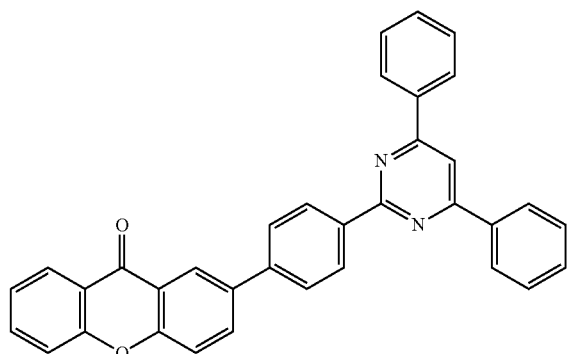
(164)
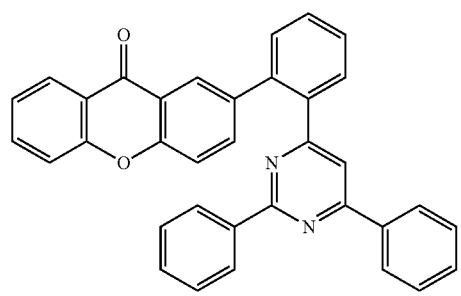
(165)
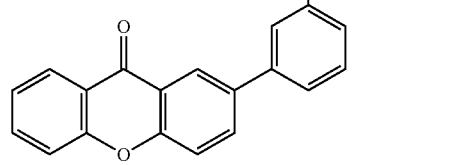
(166)
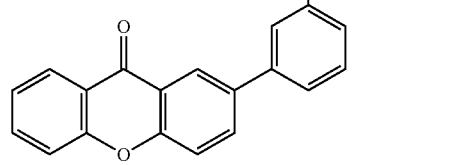
(167)
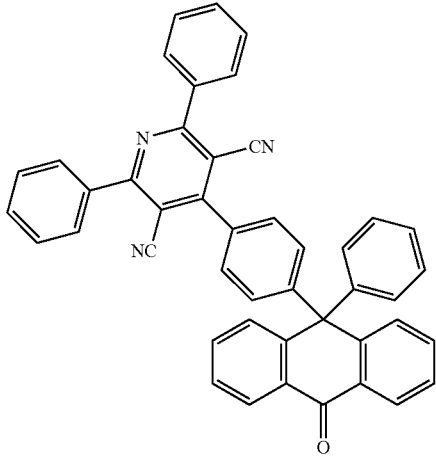
(168)
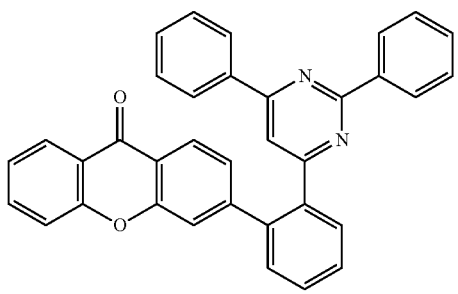
(169)
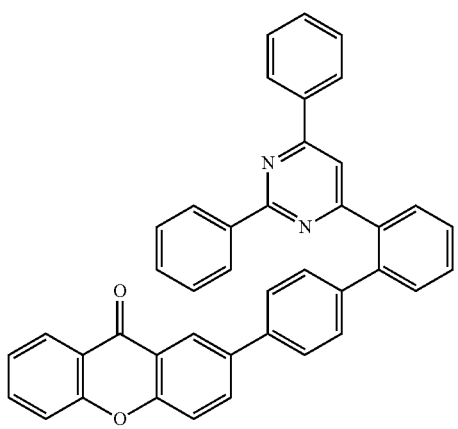

(170)
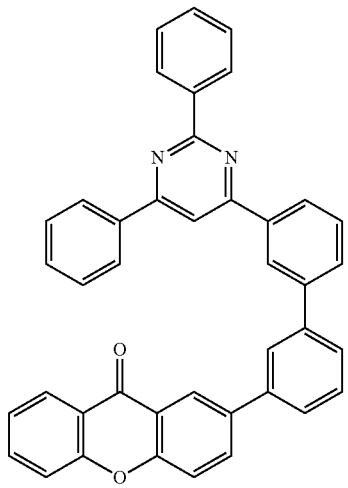
(171)
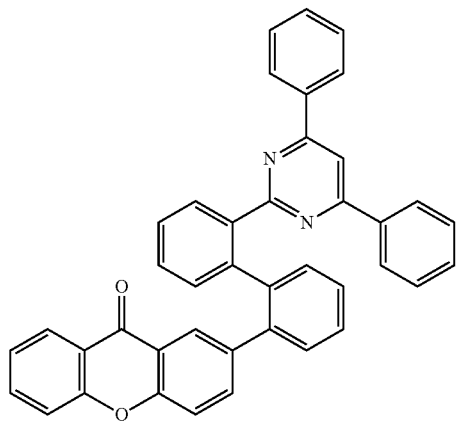
(172)
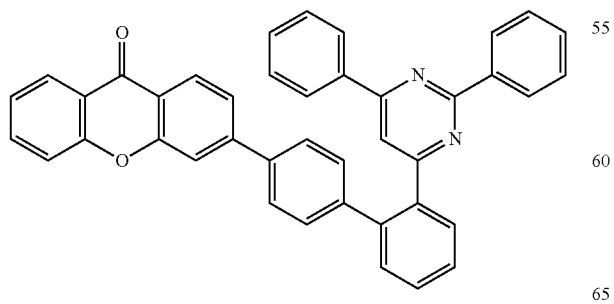
(173)
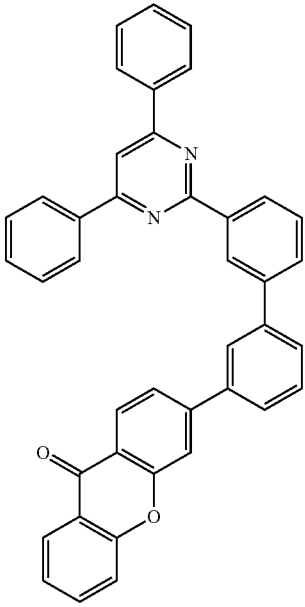
(174)
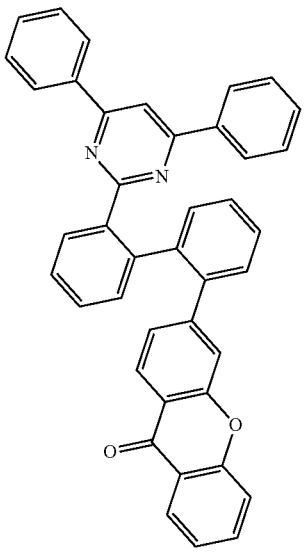
and
(175)
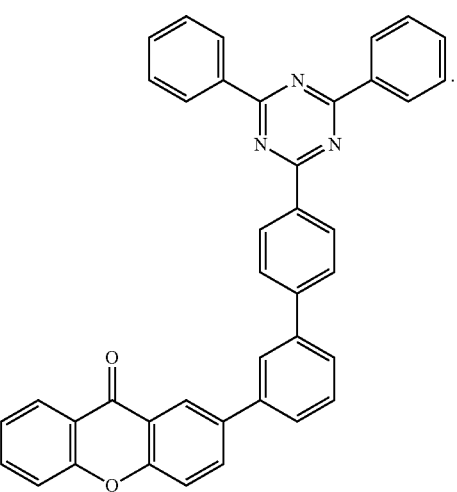

A preparation method of the compound, wherein reaction occurring in the preparation process follows an equation as follows:

(1) when X represents oxygen atom or sulfur atom, k=0, m=0, n=1:

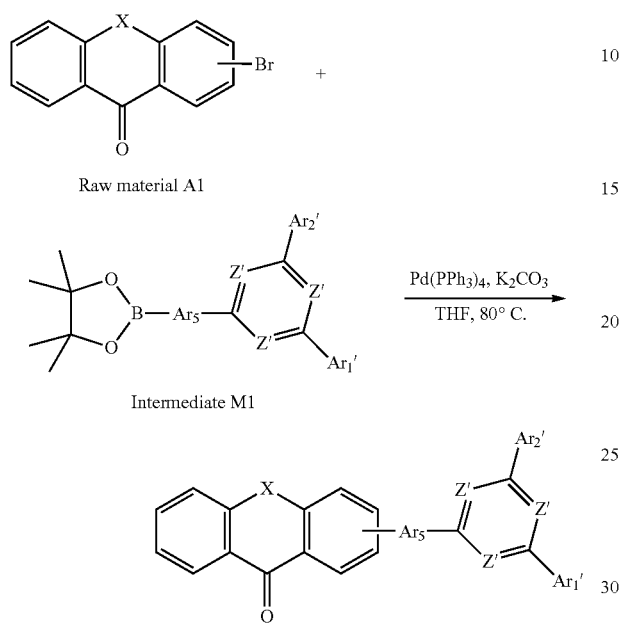

Raw material A1

Intermediate M1

The specific reaction process is as follows:

In a nitrogen atmosphere, weighing and dissolving raw material A1 in tetrahydrofuran (THF), then, adding intermediate M1 and tetrakis (triphenylphosphine) palladium, stirring the mixture, adding an aqueous solution of potassium carbonate, heating and refluxing the mixed solution containing the above reactants for 5-20 hours at a reaction temperature of 70° C. to 90° C.; after completion of the reaction, cooling and adding water, extracting the mixture with dichloromethane, drying extract liquid with anhydrous sodium sulfate, filtering and concentrating under reduced pressure, and purifying the resulting residue using a silica gel column to obtain a target compound;

wherein the molar ratio of raw material A1 to intermediate M1 is 1:1.0-1.5, the molar ratio of tetrakis (triphenylphosphine) palladium to raw material A1 is 0.001-0.02:1, the molar ratio of potassium carbonate to raw material A1 is 1.0-2.0:1, and the dosage ratio of raw material A1 to THF is 1 g:10-30 ml;

(2) when X represents carbon atom, k=1, m=0, n=1:

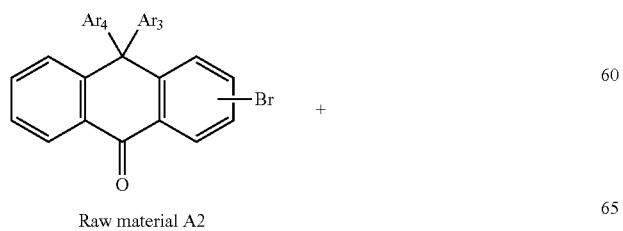

Raw material A2

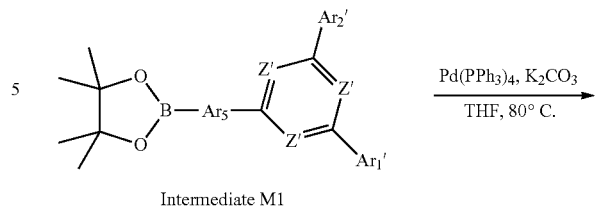

Intermediate M1

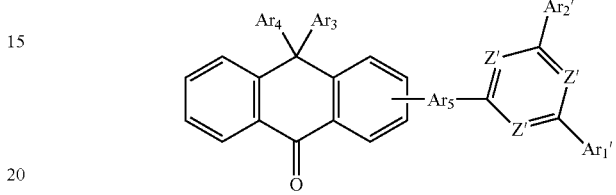

the specific reaction process is as follows:

In a nitrogen atmosphere, weighing and dissolving raw material A2 in tetrahydrofuran (THF), then, adding intermediate M1 and tetrakis (triphenylphosphine) palladium, stirring the mixture, adding an aqueous solution of potassium carbonate, heating and refluxing the mixed solution containing the above reactants for 5-20 hours at a reaction temperature of 70° C. to 90° C.; after completion of the reaction, cooling and adding water, extracting the mixture with dichloromethane, drying extract liquid with anhydrous sodium sulfate, filtering and concentrating under reduced pressure, and purifying the resulting residue using a silica gel column to obtain a target compound;

wherein the molar ratio of raw material A2 to intermediate M1 is 1:1.0-1.5, the molar ratio of tetrakis (triphenylphosphine) palladium to raw material A2 is 0.001-0.02:1, the molar ratio of potassium carbonate to raw material A2 is 1.0-2.0:1, and the dosage ratio of raw material A2 to THF is 1 g:10-30 ml;

(3) when X represents carbon atom, k=1, m=1, n=0:

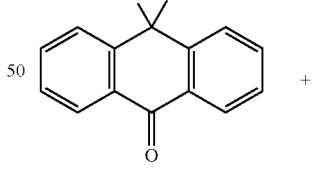

Raw material A3

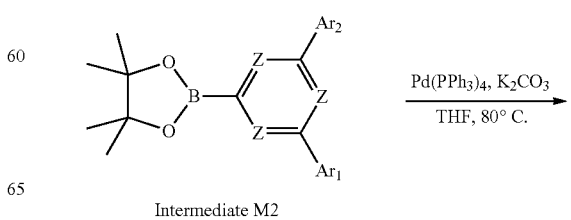

Intermediate M2

-continued

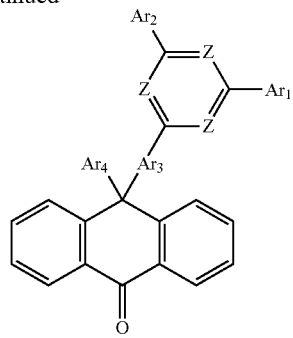

the specific reaction process is as follows:

In a nitrogen atmosphere, weighing and dissolving raw material A3 in tetrahydrofuran (THF), then, adding intermediate M2 and tetrakis (triphenylphosphine) palladium, stirring the mixture, adding an aqueous solution of potassium carbonate, heating and refluxing the mixed solution containing the above reactants for 5-20 hours at a reaction temperature of 70° C. to 90° C.; after completion of the reaction, cooling and adding water, extracting the mixture with dichloromethane, drying extract liquid with anhydrous sodium sulfate, filtering and concentrating under reduced pressure, and purifying the resulting residue using a silica gel column to obtain a target compound;

wherein the molar ratio of raw material A3 to intermediate M2 is 1:1.0-1.5, the molar ratio of tetrakis (triphenylphosphine) palladium to raw material A3 is 0.001-0.02:1, the molar ratio of potassium carbonate to raw material A3 is 1.0-2.0:1, and the dosage ratio of raw material A3 to THF is 1 g:10-30 ml.

An organic electroluminescent device containing the compound, wherein the organic electroluminescent device includes at least one functional layer containing the compound with anthrone and N-containing heterocycle.

An organic electroluminescent device containing the compound, wherein the organic electroluminescent device includes a hole block layer or an electron transport layer, wherein, the hole block layer or the electron transport layer contains the compound with anthrone and N-containing heterocycle.

An organic electroluminescent device containing the compound, wherein the organic electroluminescent device includes a light-emitting layer, wherein the light-emitting layer contains the compound with anthrone and N-containing heterocycle.

A lighting or display element, comprising the organic electroluminescent device, wherein the lighting or display element comprises the organic electroluminescent device.

The present invention achieves the following beneficial effects:

The compound of the present invention takes anthrone and N-containing heterocycle as skeletons and is connected by aromatic groups. Both anthrone and N-containing heterocycle are strong electronic-withdrawing groups, with a deep HOMO energy level and high electron mobility. Through the modification with other aromatic groups, the HOMO energy level can be adjusted freely. Therefore, the material can be used as an electron-type luminescent material, or as a material for a hole block layer or an electron transport layer. The structure containing hole groups in the present invention can balance the electrons and holes of the material, so that the material can be used as a host material for an electron-type light-emitting layer. The specific structure of anthrone can affect the distribution of HOMO energy level, LUMO energy level and triplet energy level of the material. A material with a deeper HOMO energy level and a slightly lower T1 energy level can be used as a material for a hole block or electron transport layer. A material with a shallower HOMO energy level and a higher T1 energy level can be used as a host material for the electron-type light-emitting layer.

In addition, both the anthrone part and the N-containing heterocycle are strong electron-withdrawing groups, separated by aromatic groups in the middle, which breaks the symmetry of the molecules and avoids the aggregation between molecules. The compound of the present invention has strong rigidity, not easily causes crystallization and aggregation between molecules, has good film-forming property, and has a high glass transition temperature and thermal stability. Therefore, when the compound of the present invention is applied to an OLED device, it can maintain the stability of the film layer made of the material and improve the service life of the OLED device. After the compound of the present invention is applied to an OLED device as an organic electroluminescent functional layer material, the current efficiency, power efficiency and external quantum efficiency of the device are greatly improved; moreover, the effect of the compound in improving the service life of the device is very obvious. The compound of the present invention has good application effects in OLED light-emitting devices and has good industrialization prospects.

BRIEF DESCRIPTION OF THE DRAWINGS

wherein, 1, a transparent substrate layer, 2, an ITO anode layer, 3, a hole injection layer, 4, a hole transport or electron block layer, 5, a light-emitting layer, 6, an electron transport or hole block layer, 7, an electron injection layer, and 8, a cathode reflective electrode layer.

DETAILED DESCRIPTION OF THE EMBODIMENTS

Example 1: Synthesis of Intermediate M

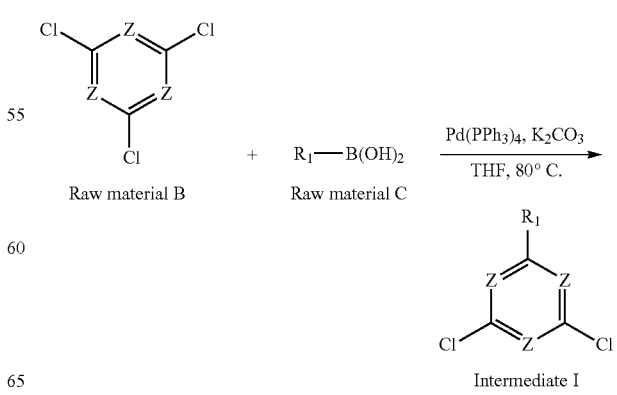

Figure 1:
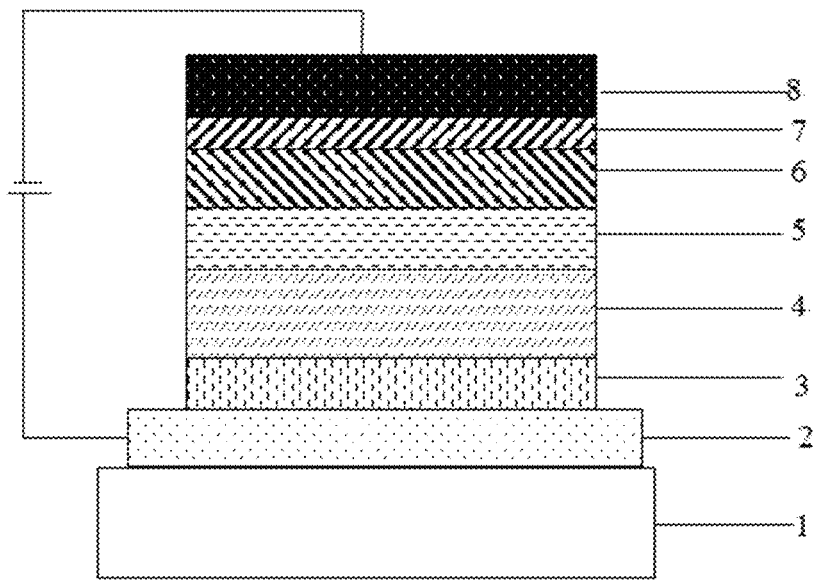
FIG. 1 is a schematic structural diagram when materials set forth in the present invention are applied to an OLED device.

(1) in a nitrogen atmosphere, raw material B was weighed and dissolved in tetrahydrofuran (THF), then, raw material C and tetrakis (triphenylphosphine) palladium were added, the mixture was stirred, an aqueous solution of potassium carbonate was then added, and the mixed solution containing the above reactants was heated and refluxed for 5-20 hours at a reaction temperature of 70° C. to 90° C. After completion of the reaction, the mixed solution was cooled and added with water, the mixture was extracted with dichloromethane, extract liquid was dried over anhydrous sodium sulfate, then filtered and concentrated under reduced pressure, and the resulting residue was purified using a silica gel column to obtain intermediate I;

wherein the molar ratio of raw material B to raw material C is 1:1.0-1.5, the molar ratio of tetrakis (triphenylphosphine) palladium to raw material B is 0.001-0.02:1, the molar ratio of potassium carbonate to raw material B is 1.0-2.0:1, and the dosage ratio of THF to raw material B is 1 g:10-30 ml.

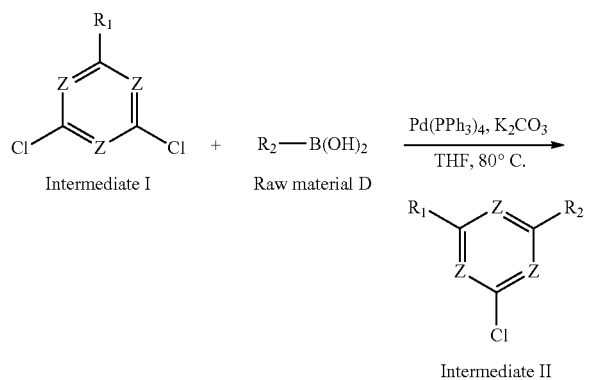

(2) In a nitrogen atmosphere, intermediate I was weighed and dissolved in tetrahydrofuran (THF), then, raw material D and tetrakis (triphenylphosphine) palladium were added, the mixture was stirred, an aqueous solution of potassium carbonate was then added, and the mixed solution containing the above reactants was heated and refluxed for 5-20 hours at a reaction temperature of 70° C. to 90° C. After completion of the reaction, the mixed solution was cooled and added with water, the mixture was extracted with dichloromethane, extract liquid was dried over anhydrous sodium sulfate, then filtered and concentrated under reduced pressure, and the resulting residue was purified using a silica gel column to obtain intermediate II;

wherein the molar ratio of intermediate I to raw material D is 1:1.0-1.5, the molar ratio of tetrakis (triphenylphosphine) palladium to intermediate I is 0.001-0.02:1, the molar ratio of potassium carbonate to intermediate I is 1.0-2.0:1, and the dosage ratio of THF to intermediate I is 1 g:10-30 ml.

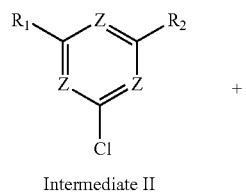

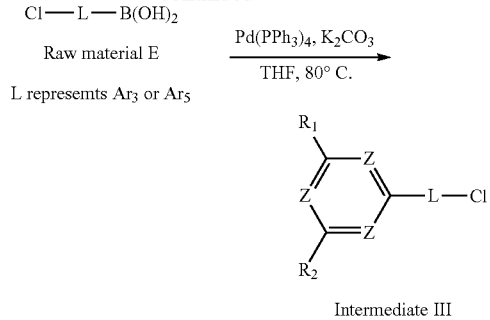

(3) In a nitrogen atmosphere, intermediate II was weighed and dissolved in tetrahydrofuran (THF), then, raw material E and tetrakis (triphenylphosphine) palladium were added, the mixture was stirred, an aqueous solution of potassium carbonate was then added, and the mixed solution containing the above reactants was heated and refluxed for 5-20 hours at a reaction temperature of 70° C. to 90° C. After completion of the reaction, the mixed solution was cooled and added with water, the mixture was extracted with dichloromethane, extract liquid was dried over anhydrous sodium sulfate, then filtered and concentrated under reduced pressure, and the resulting residue was purified using a silica gel column to obtain intermediate III;

wherein the molar ratio of intermediate II to raw material E is 1:1.0-1.5, the molar ratio of tetrakis (triphenylphosphine) palladium to intermediate II is 0.001-0.02:1, the molar ratio of potassium carbonate to intermediate II is 1.0-2.0:1, and the dosage ratio of THF to intermediate II is 1 g:10-30 ml.

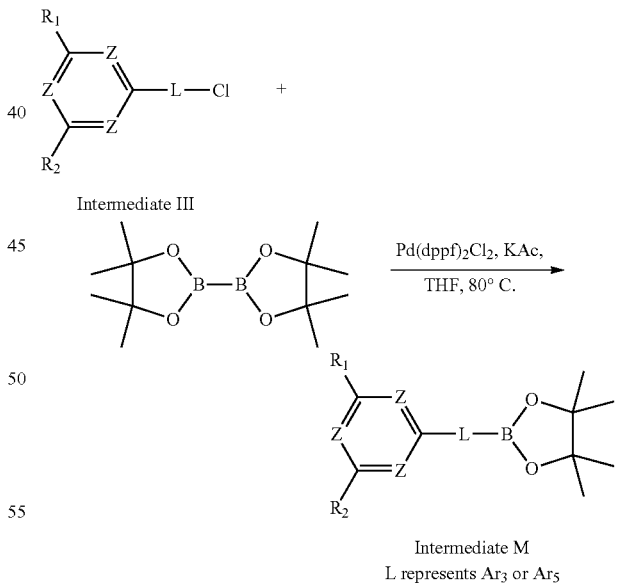

In a nitrogen atmosphere, intermediate III was weighed and dissolved in tetrahydrofuran (THF), then, bis (pinacolyl) diboron, (1,1'-bis (diphenylphosphino) ferrocene) dichloropalladium (II) and potassium acetate were added, the mixture was stirred, and the mixed solution containing the above reactants was heated and refluxed for 5-10 hours at a reaction temperature of 70° C. to 90° C.; after completion of the reaction, the reaction solution was added with water and cooled and then the mixture was filtered and dried in a vacuum oven. The resulting residue was separated and purified using a silica gel column to obtain an intermediate M.

Taking the synthesis of intermediate M-5 as an example:

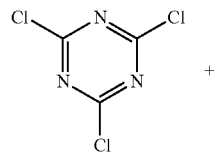

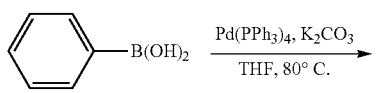

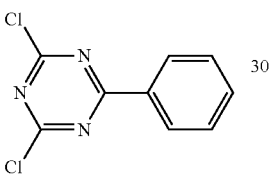

Intermediate X (1) In a 250 ml three-necked flask, nitrogen gas was introduced, 0.04 mol of raw material 2,4,6-Trichloropyridine, 150 ml of THF, 0.05 mol of 4-biphenylboronic acid, and 0.0004 mol of tetrakis (triphenylphosphine) palladium were added, the mixture was stirred, 0.06 mol of the aqueous solution of $K_2CO_3$ (2M) was added, and the mixed solution was heated to 80° C. and refluxed for 10 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain intermediate X; the purity of the product by HPLC was 99.5%, and the yield was 75.4%. Elemental analysis structure (molecular formula $C_9H_5Cl_2N_3$): theoretical values: C, 47.82; H, 2.23; Cl, 31.36; N, 18.59; test values: C, 47.81; H, 2.23; Cl, 31.36; N, 18.60. ESI-MS(m/z)($M^+$): the theoretical value is 224.99, and the test value is 225.20.

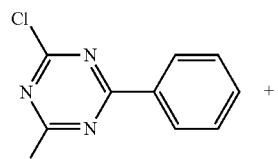

Intermediate X

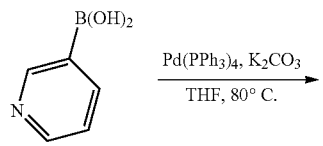

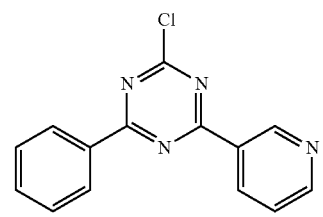

Intermediate Y (2) In a 250 ml three-necked flask, nitrogen gas was introduced, 0.02 mol of intermediate X, 120 ml of THF, 0.025 mol of 9,9-dimethyl-2-boronic acid, and 0.0002 mol of tetrakis (triphenylphosphine) palladium were added, the mixture was stirred, 0.03 mol of the aqueous solution of $K_2CO_3$ (2M) was added, and the mixed solution was heated to 80° C. and refluxed for 10 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain an intermediate Y; the purity of the product by HPLC was 99.1%, and the yield was 67.3%. Elemental analysis structure (molecular formula $C_{14}H_9ClN_4$): theoretical values: C, 62.58; H, 3.38; Cl, 13.19; N, 20.85; test values: C, 62.58; H, 3.38; Cl, 13.20; N, 20.84. ESI-MS(m/z)($M^+$): the theoretical value is 268.05, and the test value is 268.65.

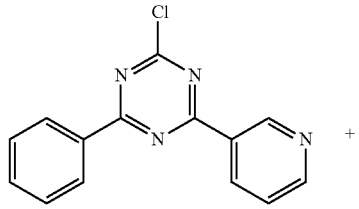

Intermediate Y

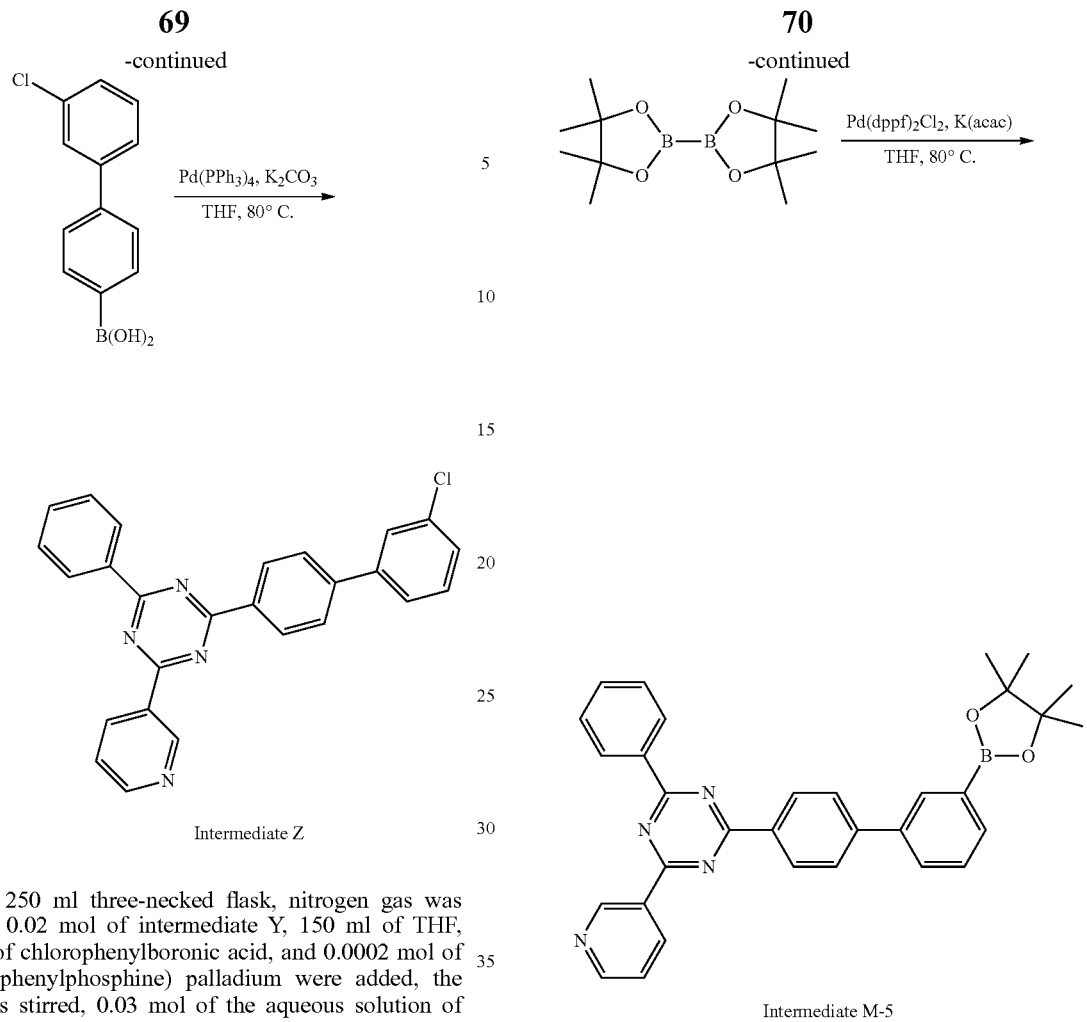

(3) In a 250 ml three-necked flask, nitrogen gas was introduced, 0.02 mol of intermediate Y, 150 ml of THF, 0.025 mol of chlorophenylboronic acid, and 0.0002 mol of tetrakis (triphenylphosphine) palladium were added, the mixture was stirred, 0.03 mol of the aqueous solution of $K_2CO_3$ (2M) was added, and the mixed solution was heated to 80° C. and refluxed for 10 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain an intermediate Z; the purity of the product by HPLC was 99.2%, and the yield was 67.1%. Elemental analysis structure (molecular formula $C_{26}H_{17}ClN_4$): theoretical values: C, 74.19; H, 4.07; Cl, 8.42; N, 13.31; test values: C, 74.20; H, 4.07; Cl, 8.42; N, 13.30. ESI-MS(m/z)(M+): the theoretical value is 420.11, and the test value is 420.70.

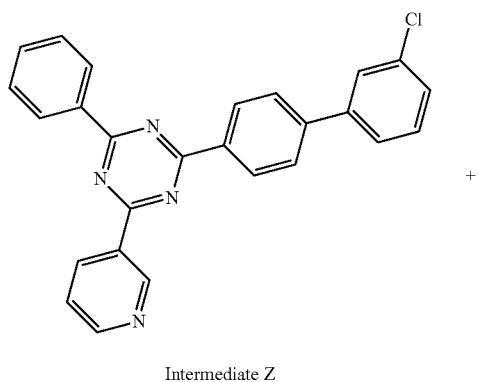

Intermediate Z (4) In a 250 ml three-necked flask, nitrogen gas was introduced, 0.02 mol of intermediate Z was added and dissolved to 150 ml of THF, 0.024 mol of bis (pinacolyl) diboron, 0.0002 mol of (1,1'-bis (diphenylphosphino) ferrocene) dichloropalladium (II) and 0.05 mol of potassium acetate were added, the mixture was stirred, the mixed solution of the above reactants was heated and refluxed for 5 hours at a reaction temperature of 80° C.; after completion of the reaction, the reaction solution was cooled and added with 100 ml of water, and the mixture was filtered and dried in a vacuum oven. The resulting residue was separated and purified using a silica gel column to obtain intermediate M-5. The purity of the product by HPLC was 99.6%, and the yield was 91.2%. Elemental analysis structure (molecular formula $C_{32}H_{29}BN_4O_2$): theoretical values: C, 75.01; H, 5.70; B, 2.11; N, 10.93; test values: C, 75.00; H, 5.70; B, 2.11; N, 10.94. ESI-MS(m/z)(M+): the theoretical value is 512.24, and the test value is 512.53.

Intermediate M was prepared by the synthesis method of intermediate M-5. The specific structure is shown in Table 1.

TABLE 1
| Raw material B | Raw material C | Raw material D | Raw material E | Intermediate M |
|---|---|---|---|---|
| 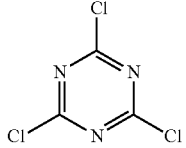 |  | 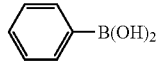 | 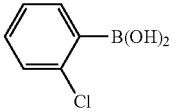 | 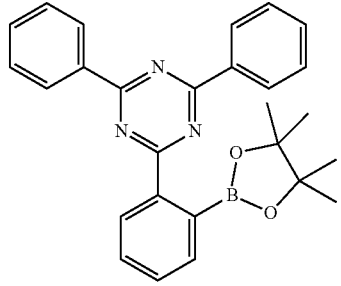 [SMILES: CC1(C)OB(c2ccccc2-c2nc(-c3ccccc3)nc(-c3ccccc3)n2)OC1(C)C]<br>Intermediate M-1 |
| 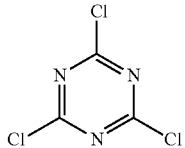 |  | 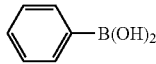 | 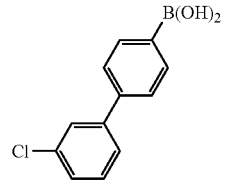 [SMILES: OB(O)c1ccc(-c2cccc(Cl)c2)cc1] | 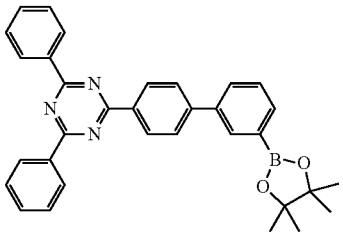 [SMILES: CC1(C)OB(c2cccc(-c3ccc(-c4nc(-c5ccccc5)nc(-c5ccccc5)n4)cc3)c2)OC1(C)C]<br>Intermediate M-2 |
| 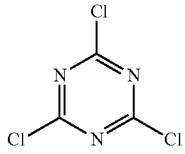 |  | 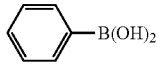 | 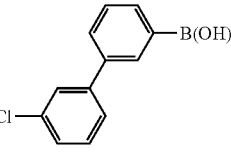 | 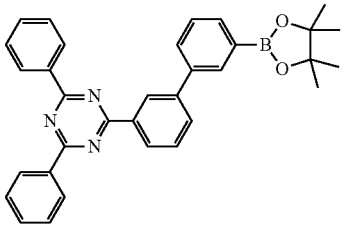 [SMILES: CC1(C)OB(c2cccc(-c3cccc(-c4nc(-c5ccccc5)nc(-c5ccccc5)n4)c3)c2)OC1(C)C]<br>Intermediate M-3 |
| 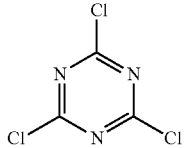 |  | 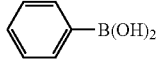 | / | 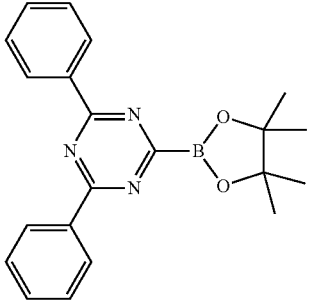 [SMILES: CC1(C)OB(c2nc(-c3ccccc3)nc(-c3ccccc3)n2)OC1(C)C]<br>Intermediate M-4 |
| 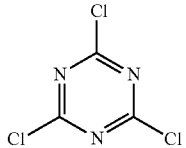 |  | 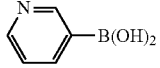 | 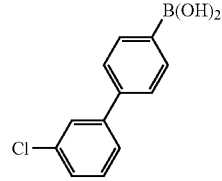 [SMILES: OB(O)c1ccc(-c2cccc(Cl)c2)cc1] | 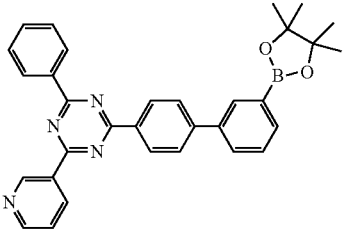 [SMILES: CC1(C)OB(c2cccc(-c3ccc(-c4nc(-c5ccccc5)nc(-c5cccnc5)n4)cc3)c2)OC1(C)C]<br>Intermediate M-5 |

TABLE 1-continued

| Raw material B | Raw material C | Raw material D | Raw material E | Intermediate M |
|---|---|---|---|---|
| 2,4,6-trichloro-1,3,5-triazine | pyridin-3-yl boronic acid | pyridin-3-yl boronic acid | 3'-chloro-[1,1'-biphenyl]-3-yl boronic acid | Intermediate M-6 |
| 2,4,6-trichloro-1,3,5-triazine | phenylboronic acid | quinolin-8-yl boronic acid | 3'-chloro-[1,1'-biphenyl]-3-yl boronic acid | Intermediate M-7 |
| 2,4,6-trichloropyridine | phenylboronic acid | phenylboronic acid | 3-chlorophenyl boronic acid | Intermediate M-8 |
| 2,4,6-trichloropyridine | phenylboronic acid | phenylboronic acid | 3'-chloro-[1,1'-biphenyl]-3-yl boronic acid | Intermediate M-9 |

TABLE 1-continued
| Raw material B | Raw material C | Raw material D | Raw material E | Intermediate M |
|---|---|---|---|---|
| 2,4,6-trichloropyridine | PhB(OH)₂ | PhB(OH)₂ | 3'-chloro-[1,1'-biphenyl]-3-yl-B(OH)₂ | 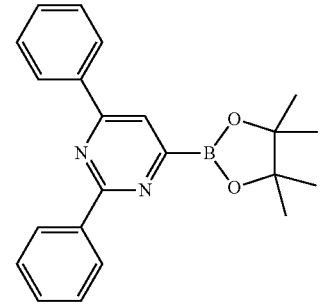 Intermediate M-10 |
| 2,4,6-trichloropyrimidine | PhB(OH)₂ | PhB(OH)₂ | / | Intermediate M-11 |
| 2,4,6-trichloropyrimidine | PhB(OH)₂ | PhB(OH)₂ | 2-chlorophenyl-B(OH)₂ | 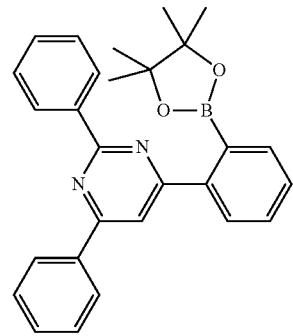 [SMILES: CC1(C)OB(c2ccccc2-c2cc(-c3ccccc3)nc(-c3ccccc3)n2)OC1(C)C] Intermediate M-12 |
| 2,4,6-trichloropyrimidine | PhB(OH)₂ | PhB(OH)₂ | / | 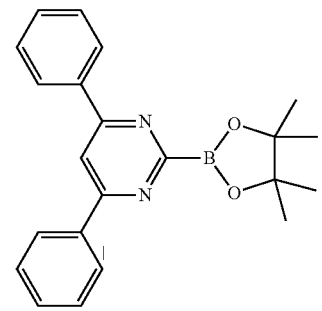 Intermediate M-13 |

TABLE 1-continued

| Raw material B | Raw material C | Raw material D | Raw material E | Intermediate M |
|---|---|---|---|---|
| | | | | Intermediate M-14 |
| | | | | Intermediate M-15 |
| | | | / | Intermediate M-16 |

Example 2: Synthesis of Compound 3

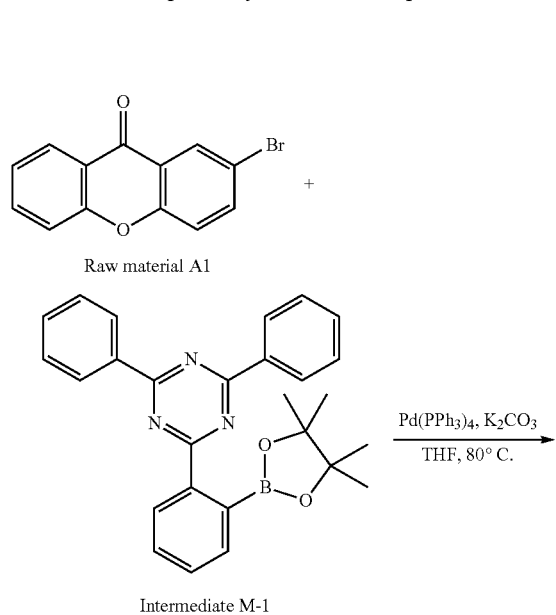

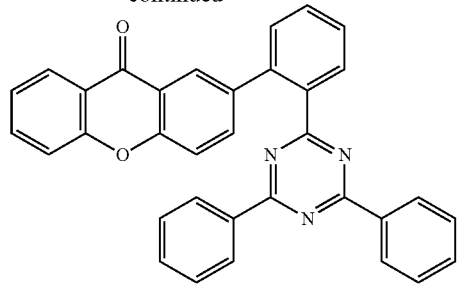

In a 250 ml three-necked flask, nitrogen gas was introduced, 0.01 mol of raw material A1, 150 ml of THF, 0.015 mol of intermediate M-1, and 0.0001 mol of tetrakis (triphenylphosphine) palladium were added, the mixture was stirred, 0.02 mol of the aqueous solution of $K_2CO_3$ (2M) was added, and the mixed solution was heated to 80° C. and refluxed for 15 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target compound; the purity of the target compound by HPLC was 99.1%, and the yield was 77.3%. Elemental analysis structure (molecular formula $C_{34}H_{21}N_3O_2$): theoretical values: C, 81.10; H, 4.20; N, 8.34; test values: C, 81.10; H, 4.20; N, 8.33. ESI-MS(m/z)(M+): the theoretical value is 503.16, and the test value is 503.65.

Example 3: Synthesis of Compound 10

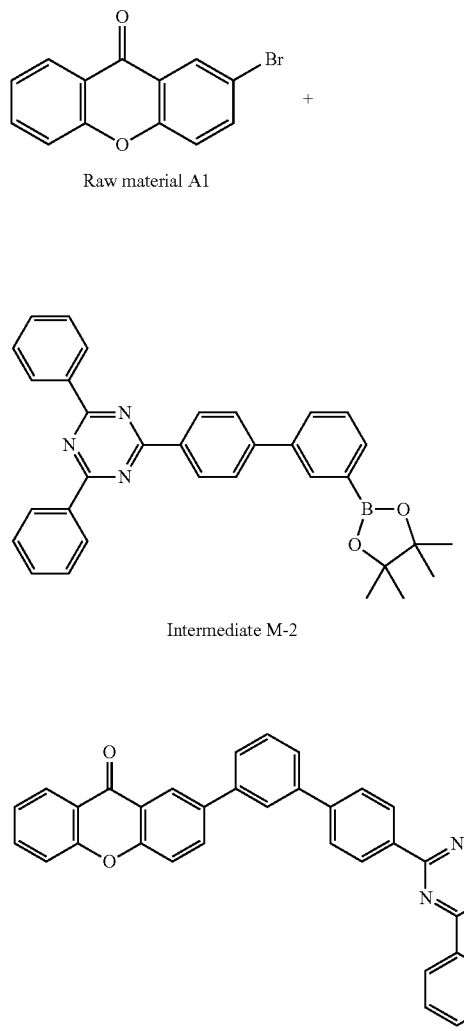

Intermediate M-2

In a 250 ml three-necked flask, nitrogen gas was introduced, 0.01 mol of raw material A1, 150 ml of THF, 0.015 mol of intermediate M-2, and 0.0001 mol of tetrakis (triphenylphosphine) palladium were added, the mixture was stirred, 0.02 mol of the aqueous solution of $K_2CO_3$ (2M) was added, and the mixed solution was heated to 80° C. and refluxed for 15 hours, sampled and spotted until completion of the reaction. The mixed solution was cooled naturally, extracted with 200 ml of dichloromethane, and layered, the extract liquid was dried over anhydrous sodium sulfate, and filtered, the filtrate was rotarily evaporated, and purified using a silica gel column to obtain a target compound; the purity of the target compound by HPLC was 99.3%, and the yield was 71.9%. Elemental analysis structure (molecular formula $C_{40}H_{25}N_3O_2$): theoretical values: C, 82.88; H, 4.35; N, 7.25; test values: C, 82.88; H, 4.35; N, 7.24. ESI-MS(m/z)(M+): the theoretical value is 579.19, and the test value is 579.75.

Example 4: Synthesis of Compound 11

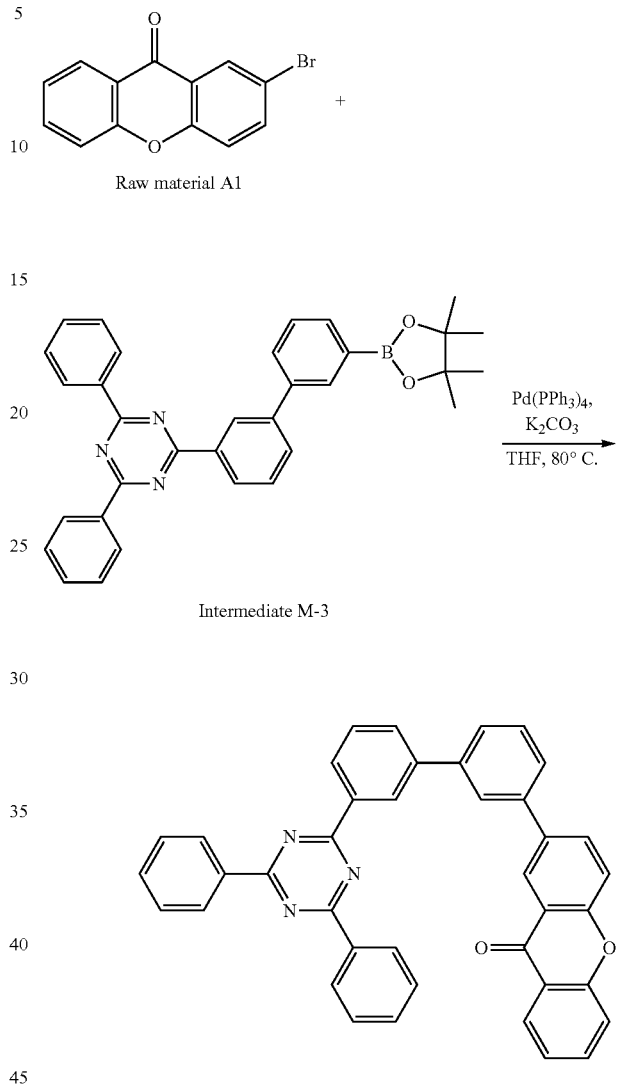

Intermediate M-3

The preparation method of the compound 11 was the same with that in Example 2, except that the intermediate M-1 was replaced with the intermediate M-3. Elemental analysis structure (molecular formula $C_{40}H_{25}N_3O_2$): theoretical values: C, 82.88; H, 4.35; N, 7.25; test values: C, 82.88; H, 4.35; N, 7.24. ESI-MS(m/z)(M+): the theoretical value is 579.19, and the test value is 580.10.

Example 5: Synthesis of Compound 20

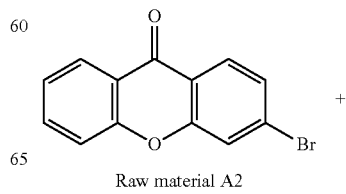

Raw material A2

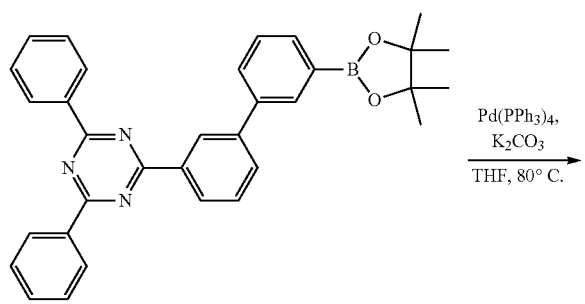

Intermediate M-3

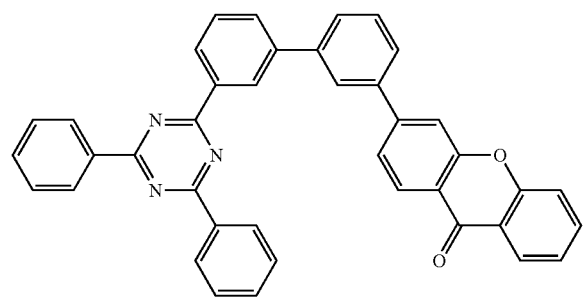

The preparation method of the compound 20 was the same with that in Example 2, except that the raw material A1 was replaced with raw material A2, and the intermediate M-1 was replaced with the intermediate M-3. Elemental analysis structure (molecular formula $C_{40}H_{25}N_3O_2$): theoretical values: C, 82.88; H, 4.35; N, 7.25; test values: C, 82.88; H, 4.35; N, 7.26. ESI-MS(m/z)(M+): the theoretical value is 579.19, and the test value is 579.45.

Example 6: Synthesis of Compound 27

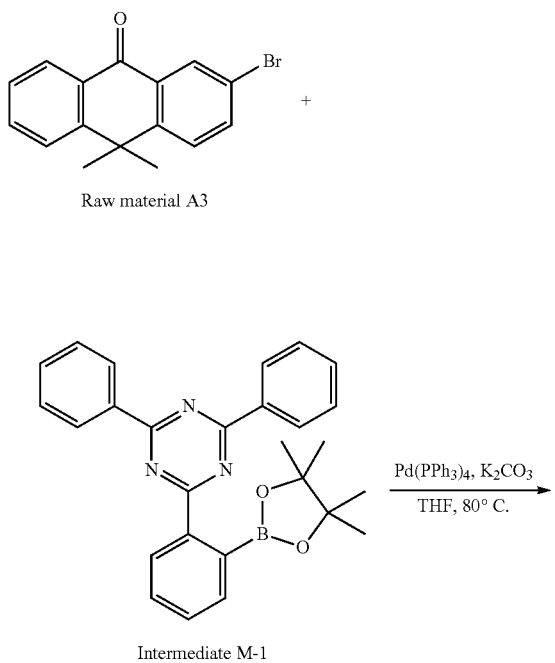

The preparation method of the compound 27 was the same with that in Example 2, except that raw material A1 was replaced with raw material A3. Elemental analysis structure (molecular formula $C_{37}H_{27}N_3O$): theoretical values: C, 83.91; H, 5.14; N, 7.93; test values: C, 83.91; H, 5.14; N, 7.94. ESI-MS(m/z)(M+): the theoretical value is 529.22, and the test value is 529.55.

Example 7: Synthesis of Compound 35

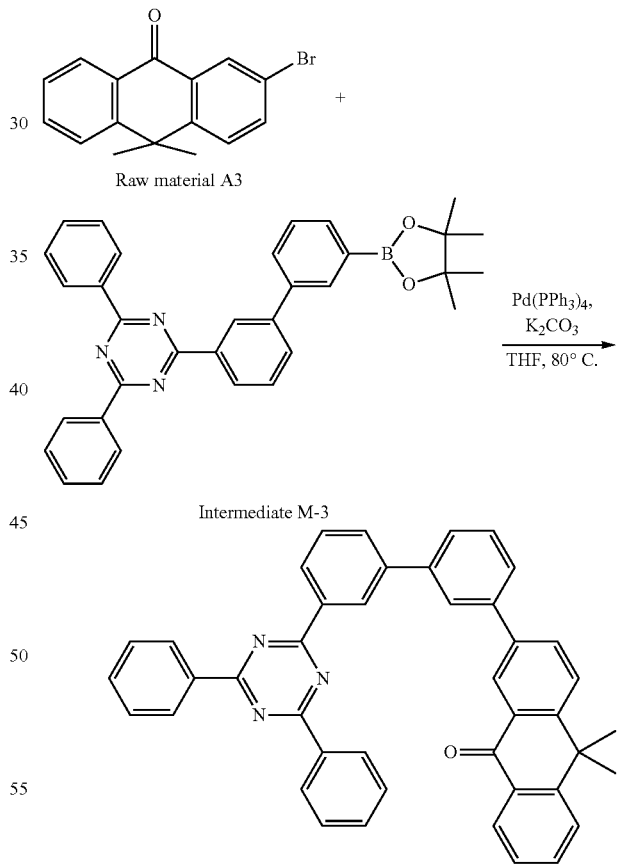

The preparation method of the compound 35 was the same with that in Example 2, except that the raw material A1 was replaced with raw material A3, and the intermediate M-1 was replaced with the intermediate M-3. Elemental analysis structure (molecular formula $C_{43}H_{31}N_3O$): theoretical values: C, 85.26; H, 5.16; N, 6.94; test values: C, 85.26; H, 5.16; N, 6.94. ESI-MS(m/z)(M+): the theoretical value is 605.74, and the test value is 605.94.

Example 8: Synthesis of Compound 44

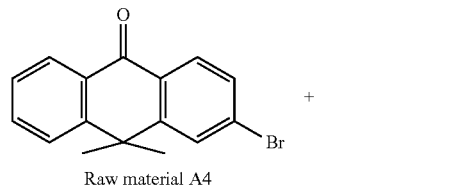

Raw material A4

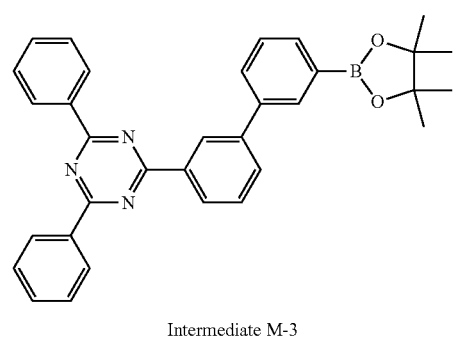

Intermediate M-3

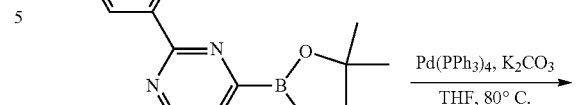

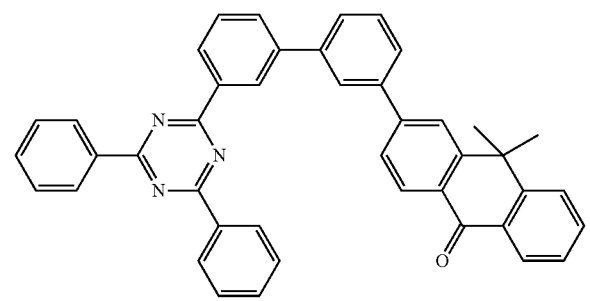

The preparation method of the compound 44 was the same with that in Example 2, except that the raw material A1 was replaced with raw material A4, and the intermediate M-1 was replaced with the intermediate M-3. Elemental analysis structure (molecular formula $C_{43}H_{31}N_3O$): theoretical values: C, 85.26; H, 5.16; N, 6.94; test values: C, 85.27; H, 5.16; N, 6.93. ESI-MS(m/z)(M+): the theoretical value is 605.25, and the test value is 605.88.

Example 9: Synthesis of Compound 50

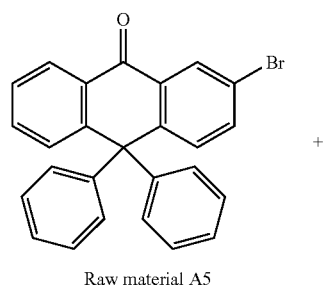

Raw material A5

-continued

Intermediate M-4

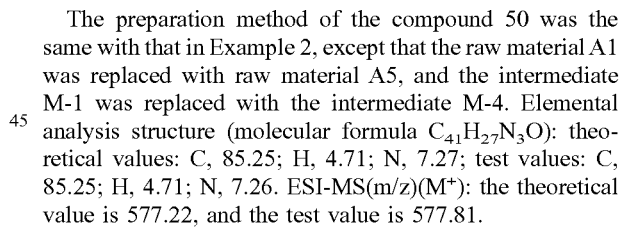

The preparation method of the compound 50 was the same with that in Example 2, except that the raw material A1 was replaced with raw material A5, and the intermediate M-1 was replaced with the intermediate M-4. Elemental analysis structure (molecular formula $C_{41}H_{27}N_3O$): theoretical values: C, 85.25; H, 4.71; N, 7.27; test values: C, 85.25; H, 4.71; N, 7.26. ESI-MS(m/z)(M+): the theoretical value is 577.22, and the test value is 577.81.

Example 10: Synthesis of Compound 59

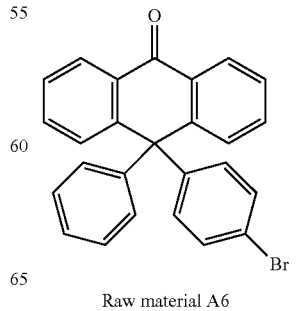

Raw material A6

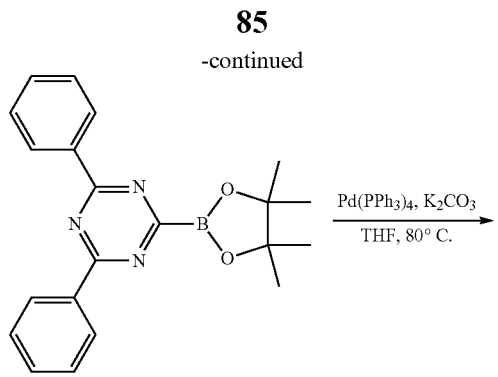

Intermediate M-4

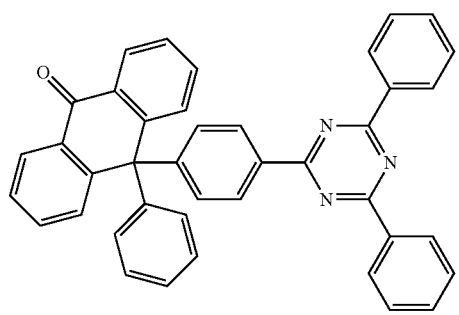

The preparation method of the compound 59 was the same with that in Example 2, except that the raw material A1 was replaced with raw material A6, and the intermediate M-1 was replaced with the intermediate M-4. Elemental analysis structure (molecular formula $C_{41}H_{27}N_3O$): theoretical values: C, 85.25; H, 4.71; N, 7.27; test values: C, 85.25; H, 4.71; N, 7.26. ESI-MS(m/z)(M$^+$): the theoretical value is 577.22, and the test value is 577.82.

Example 11: Synthesis of Compound 69

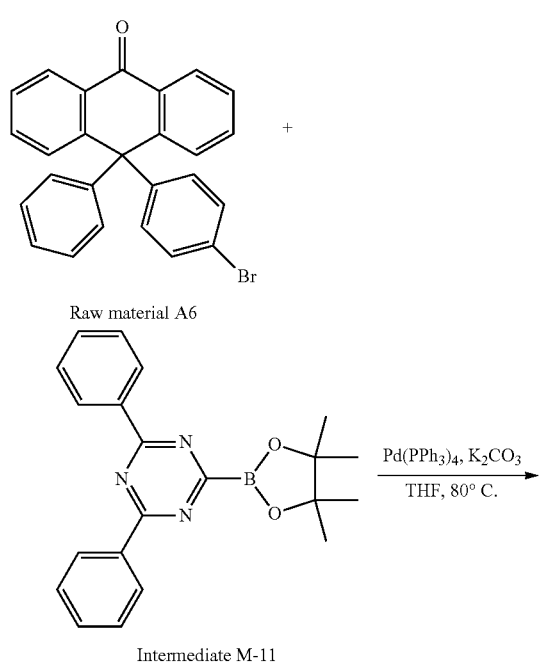

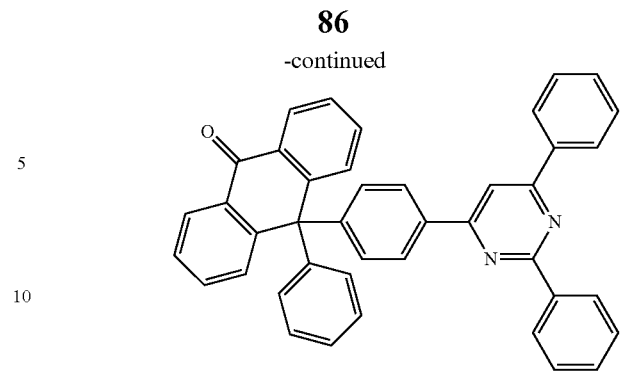

The preparation method of the compound 69 was the same with that in Example 2, except that the raw material A1 was replaced with raw material A6, and the intermediate M-1 was replaced with the intermediate M-11. Elemental analysis structure (molecular formula $C_{42}H_{28}N_2O$): theoretical values: C, 87.47; H, 4.89; N, 4.86; test values: C, 87.47; H, 4.89; N, 4.85. ESI-MS(m/z)(M$^+$): the theoretical value is 576.22, and the test value is 576.55.

Example 12: Synthesis of Compound 79

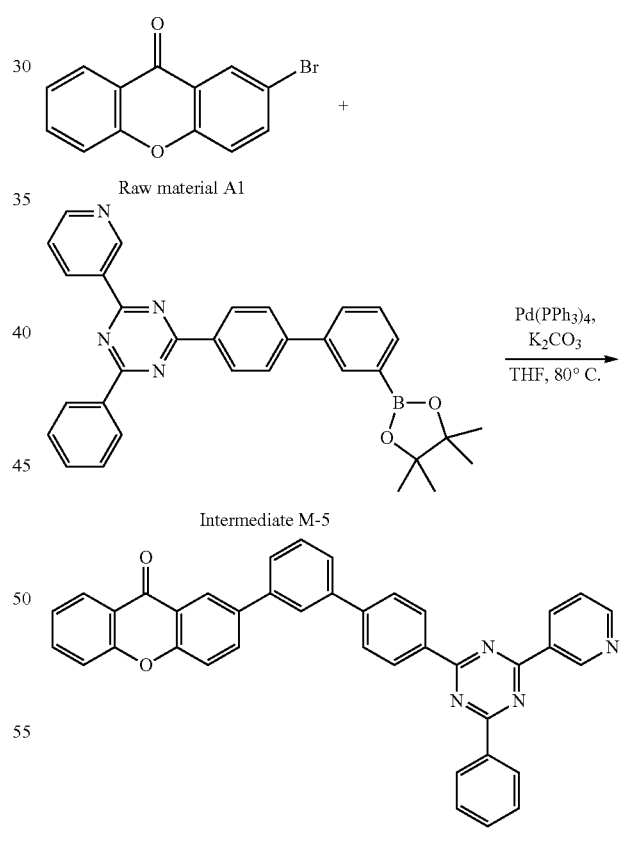

The preparation method of the compound 79 was the same with that in Example 2, except that the intermediate M-1 was replaced with the intermediate M-5. Elemental analysis structure (molecular formula $C_{39}H_{24}N_4O_2$): theoretical values: C, 80.67; H, 4.17; N, 9.65; test values: C, 80.67; H, 4.17; N, 9.64. ESI-MS(m/z)(M$^+$): the theoretical value is 580.19, and the test value is 580.56.

Example 13: Synthesis of Compound 80

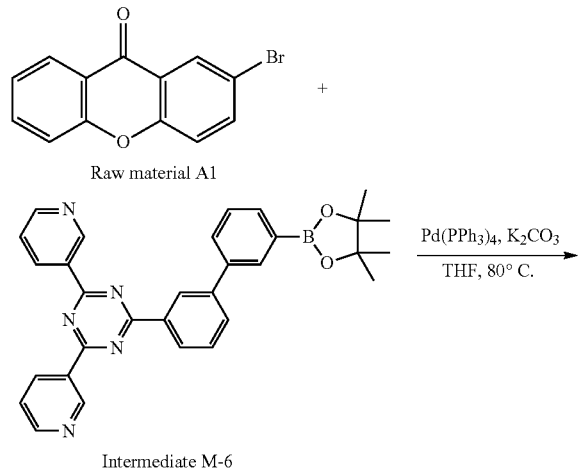

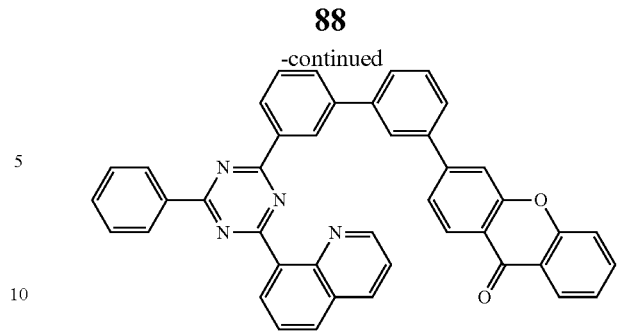

The preparation method of the compound 80 was the same with that in Example 2, except that the intermediate M-1 was replaced with the intermediate M-6. Elemental analysis structure (molecular formula $C_{38}H_{23}N_5O_2$): theoretical values: C, 78.47; H, 3.99; N, 12.04; test values: C, 78.46; H, 3.99; N, 12.04. ESI-MS(m/z)(M$^+$): the theoretical value is 581.19, and the test value is 581.75.

Example 14: Synthesis of Compound 89

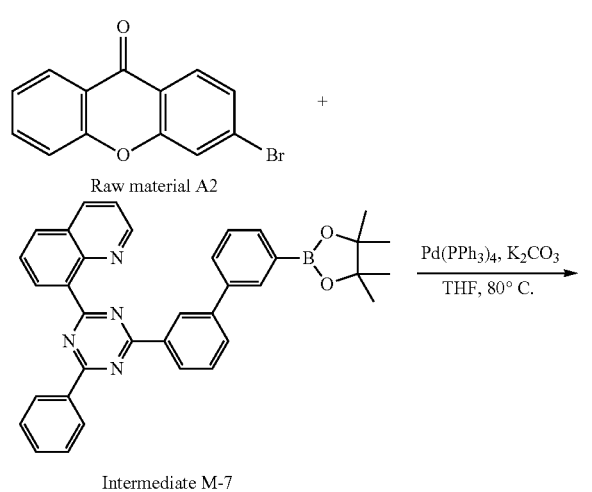

The preparation method of the compound 89 was the same with that in Example 2, except that the raw material A1 was replaced with raw material A2, and the intermediate M-1 was replaced with the intermediate M-7. Elemental analysis structure (molecular formula $C_{43}H_{26}N_4O_2$): theoretical values: C, 81.89; H, 4.16; N, 8.88; test values: C, 81.89; H, 4.16; N, 8.89. ESI-MS(m/z)(M$^+$): the theoretical value is 630.21, and the test value is 630.81.

Example 15: Synthesis of Compound 95

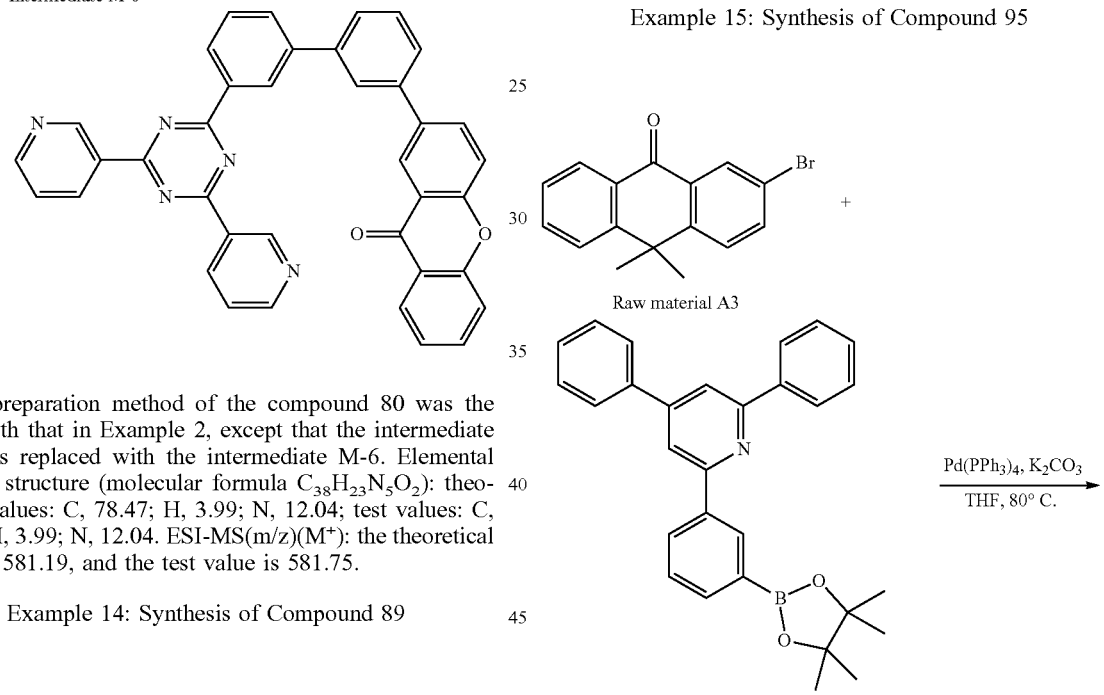

The preparation method of the compound 95 was the same with that in Example 2, except that the raw material A1 was replaced with raw material A3, and the intermediate M-1 was replaced with the intermediate M-8. Elemental analysis structure (molecular formula $C_{39}H_{29}NO$): theoretical values: C, 88.77; H, 5.54; N, 2.65; test values: C, 88.78;

H, 5.54; N, 2.65. ESI-MS(m/z)(M⁺): the theoretical value is 527.22, and the test value is 527.62.

Example 16: Synthesis of Compound 104

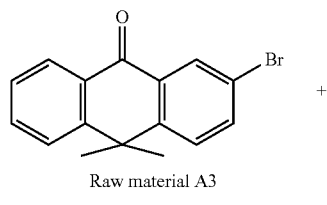

Raw material A3

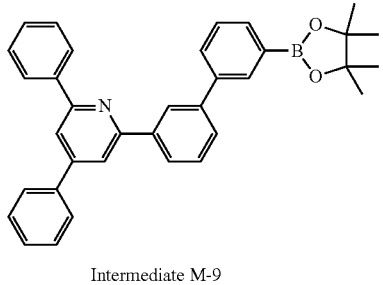

Intermediate M-9

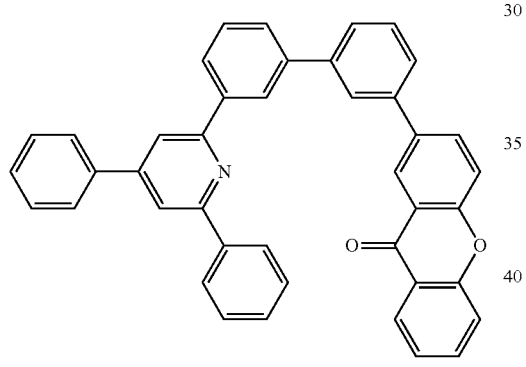

The preparation method of the compound 104 was the same with that in Example 2, except that the raw material A1 was replaced with raw material A3, and the intermediate M-1 was replaced with the intermediate M-9. Elemental analysis structure (molecular formula C$_{45}$H$_{33}$NO): theoretical values: C, 89.52; H, 5.51; N, 2.32; test values: C, 89.52; H, 5.51; N, 2.33. ESI-MS(m/z)(M⁺): the theoretical value is 603.26, and the test value is 603.76.

Example 17: Synthesis of Compound 113

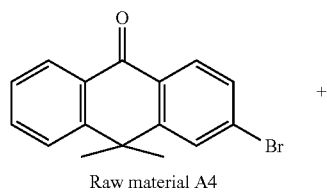

Raw material A4

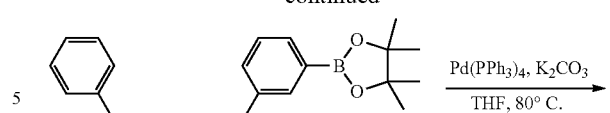

Intermediate M-10

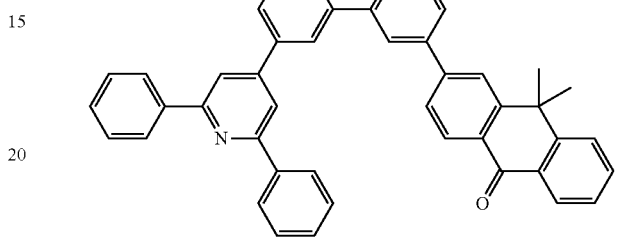

The preparation method of the compound 113 was the same with that in Example 2, except that the raw material A1 was replaced with raw material A4, and the intermediate M-1 was replaced with the intermediate M-10. Elemental analysis structure (molecular formula C$_{45}$H$_{33}$NO): theoretical values: C, 89.52; H, 5.51; N, 2.32; test values: C, 89.52; H, 5.51; N, 2.33. ESI-MS(m/z)(M⁺): the theoretical value is 603.26, and the test value is 603.36.

Example 18: Synthesis of Compound 119

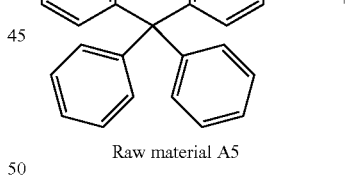

Raw material A5

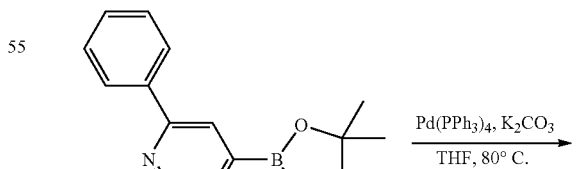

Intermediate M-11

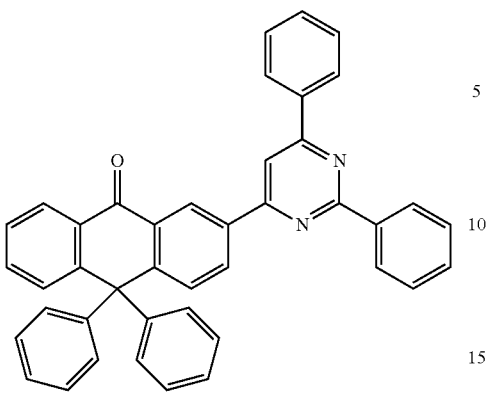

The preparation method of the compound 119 was the same with that in Example 2, except that the raw material A1 was replaced with raw material A5, and the intermediate M-1 was replaced with the intermediate M-11. Elemental analysis structure (molecular formula $C_{42}H_{28}N_2O$): theoretical values: C, 87.47; H, 4.89; N, 4.86; test values: C, 87.47; H, 4.89; N, 4.87. ESI-MS(m/z)(M$^+$): the theoretical value is 576.22, and the test value is 576.82.

Example 19: Synthesis of Compound 126

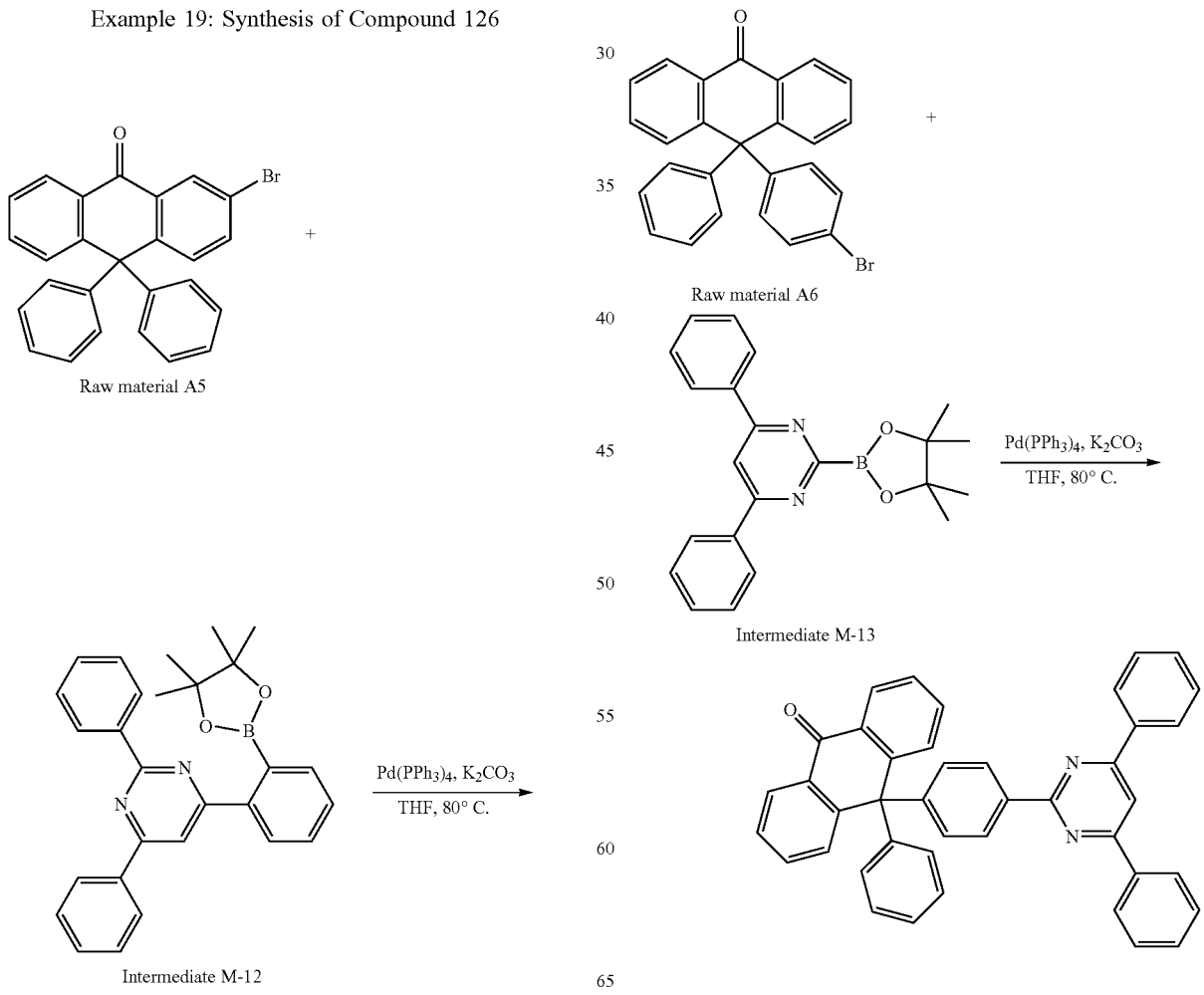

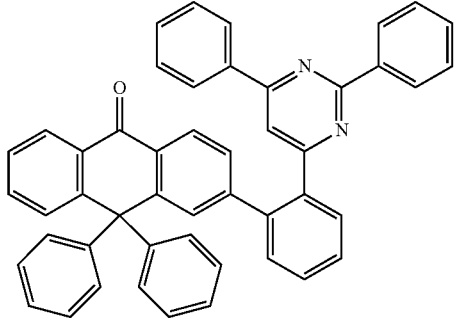

The preparation method of the compound 126 was the same with that in Example 2, except that the raw material A1 was replaced with raw material A5, and the intermediate M-1 was replaced with the intermediate M-12. Elemental analysis structure (molecular formula $C_{48}H_{32}N_2O$): theoretical values: C, 88.32; H, 4.94; N, 4.29; test values: C, 88.31; H, 4.94; N, 4.29. ESI-MS(m/z)(M$^+$): the theoretical value is 652.25, and the test value is 652.45.

Example 20: Synthesis of Compound 128

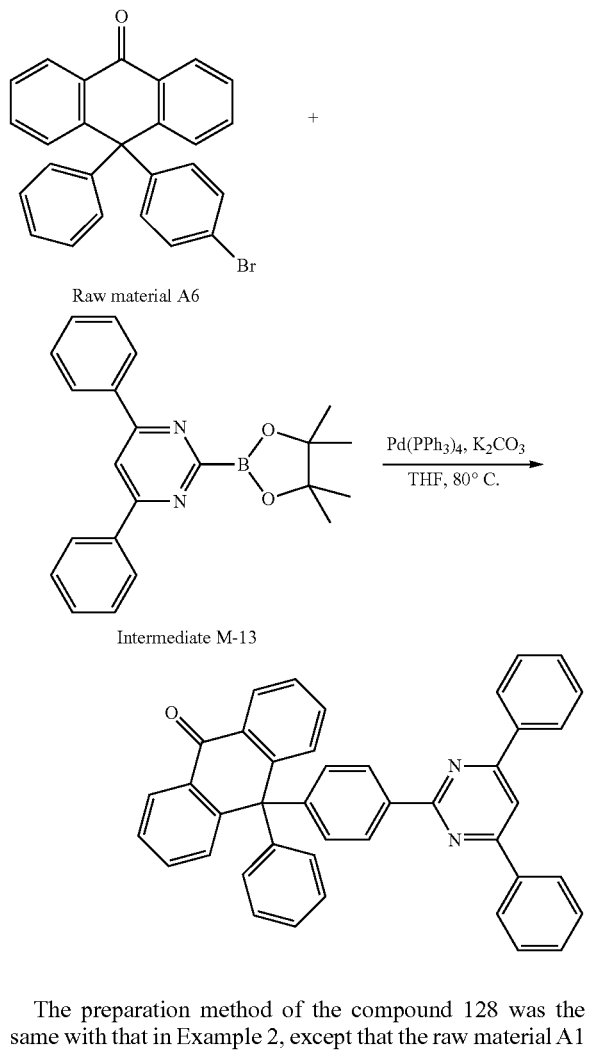

The preparation method of the compound 128 was the same with that in Example 2, except that the raw material A1 was replaced with raw material A6, and the intermediate M-1 was replaced with the intermediate M-13. Elemental analysis structure (molecular formula $C_{42}H_{28}N_2O$): theoretical values: C, 87.47; H, 4.89; N, 4.86; test values: C, 87.47; H, 4.89; N, 4.85. ESI-MS(m/z)(M+): the theoretical value is 576.22, and the test value is 576.98.

Example 21: Synthesis of Compound 139

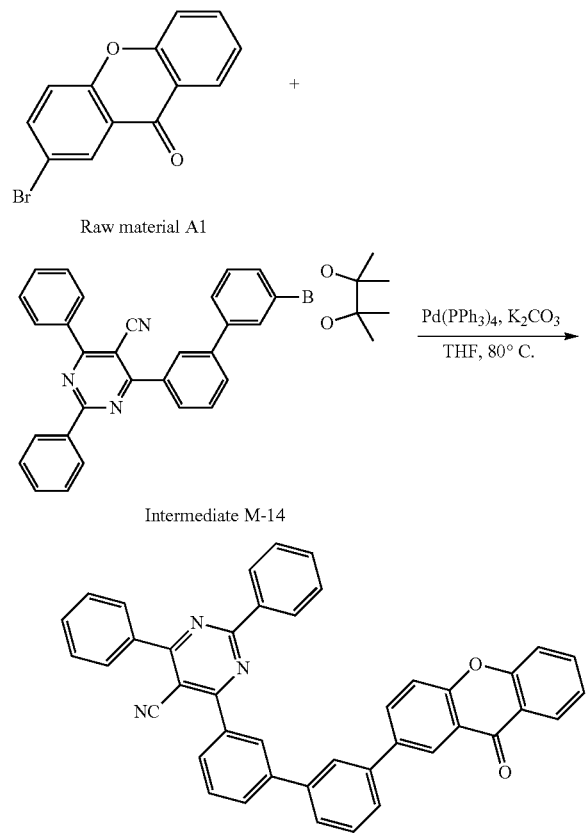

Intermediate M-14

The preparation method of the compound 139 was the same with that in Example 2, except that the intermediate M-1 was replaced with the intermediate M-14. Elemental analysis structure (molecular formula $C_{42}H_{25}N_3O_2$): theoretical values: C, 83.56; H, 4.17; N, 6.96; test values: C, 83.56; H, 4.17; N, 6.95. ESI-MS(m/z)(M+): the theoretical value is 603.19, and the test value is 603.77.

Example 22: Synthesis of Compound 153

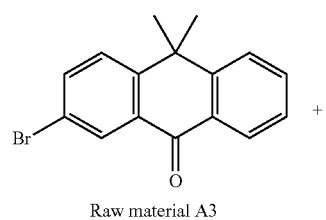

Raw material A3

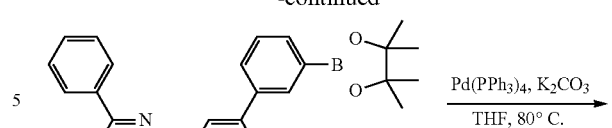

Intermediate M-15

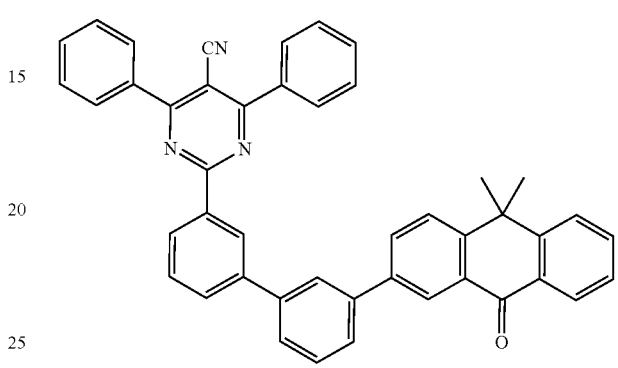

The preparation method of the compound 153 was the same with that in Example 2, except that the raw material A1 was replaced with raw material A3, and the intermediate M-1 was replaced with the intermediate M-15. Elemental analysis structure (molecular formula $C_{45}H_{31}N_3O$): theoretical values: C, 85.83; H, 4.96; N, 6.67; test values: C, 85.83; H, 4.96; N, 6.66. ESI-MS(m/z)(M+): the theoretical value is 629.25, and the test value is 629.65.

Example 23: Synthesis of Compound 167

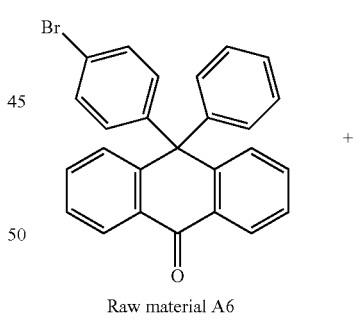

Raw material A6

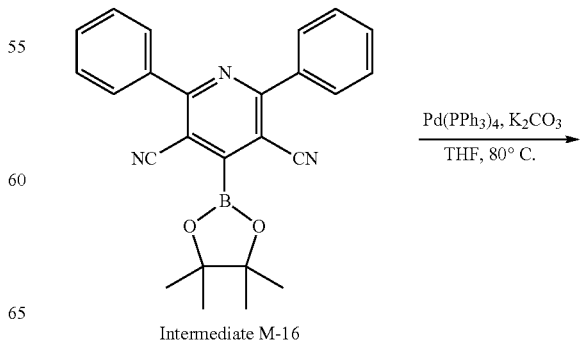

Intermediate M-16

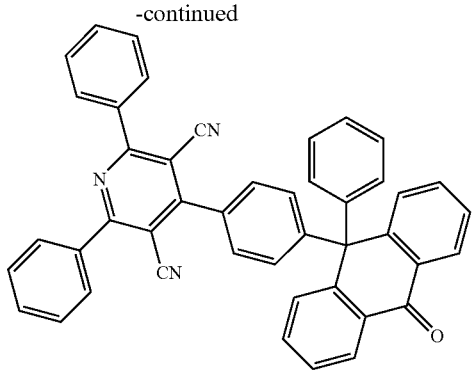

The preparation method of the compound 167 was the same with that in Example 2, except that the raw material A1 was replaced with raw material A6, and the intermediate M-1 was replaced with the intermediate M-16. Elemental analysis structure (molecular formula $C_{45}H_{27}N_3O$): theoretical values: C, 86.38; H, 4.35; N, 6.72; test values: C, 86.38; H, 4.35; N, 6.73. ESI-MS(m/z)(M$^+$): the theoretical value is 625.22, and the test value is 625.76.

When applied to a light-emitting device, the organic compound with a high Tg temperature (glass transition temperature) and triplet energy level (T1) and suitable HOMO and LUMO energy level can be used as a hole block/electron transport material and can also be uses as light-emitting layer material. Thermal property tests, T1 energy level tests and HOMO energy level tests were performed on the compounds of the present invention and the existing materials, respectively, and the results are as shown in Table 2.

TABLE 2

| Compound | T1 (ev) | Tg (° C.) | Td (° C.) | HOMO energy level (ev) | Functional layer |
|---|---|---|---|---|---|
| Compound 3 | 2.85 | 136 | 406 | −6.23 | Light-emitting layer |
| Compound 10 | 2.86 | 148 | 427 | −6.21 | Light-emitting layer |
| Compound 11 | 2.76 | 150 | 434 | −6.18 | Light-emitting layer |
| Compound 20 | 2.78 | 146 | 417 | −6.23 | Light-emitting layer |
| Compound 27 | 2.77 | 143 | 422 | −6.18 | Light-emitting layer |
| Compound 35 | 2.82 | 144 | 423 | −6.18 | Light-emitting layer |
| Compound 44 | 2.79 | 145 | 429 | −6.21 | Light-emitting layer |
| Compound 50 | 2.81 | 136 | 405 | −6.47 | Hole block or electron transport layer |
| Compound 59 | 2.81 | 142 | 424 | −6.21 | Light-emitting layer |
| Compound 69 | 2.78 | 142 | 416 | −6.19 | Light-emitting layer |
| Compound 79 | 2.82 | 139 | 408 | −6.39 | Hole block or electron transport layer |
| Compound 80 | 2.80 | 157 | 436 | −6.46 | Hole block or electron transport layer |
| Compound 89 | 2.81 | 137 | 413 | −6.44 | Hole block or electron transport layer |
| Compound 95 | 2.82 | 143 | 424 | −6.19 | Light-emitting layer |
| Compound 104 | 2.71 | 140 | 400 | −6.18 | Light-emitting layer |
| Compound 113 | 2.74 | 146 | 429 | −6.16 | Light-emitting layer |
| Compound 119 | 2.80 | 154 | 436 | −6.45 | Hole block or electron transport layer |
| Compound 126 | 2.82 | 139 | 410 | −6.41 | Hole block or electron transport layer |
| Compound 128 | 2.85 | 148 | 426 | −6.20 | Light-emitting layer |
| Compound 139 | 2.82 | 135 | 413 | −6.45 | Hole block or electron transport layer |
| Compound 153 | 2.77 | 145 | 424 | −6.23 | Light-emitting layer |
| Compound 167 | 2.81 | 144 | 436 | −6.21 | Light-emitting layer |
| CBP | 2.52 | — | 373 | −6.17 | Light-emitting layer |
| TPBi | 2.58 | 121 | 390 | −6.44 | Hole block or electron transport layer |

Note:
The triplet energy level T1 was tested by F4600 fluorescence spectrometer provided by Hitachi, and the test condition of the materials was 2*10$^{-5}$ toluene solution; the glass transition temperature Tg was differential scanning calorimetry (DSC, DSC204F1 Differential Scanning Calorimeter, NETZSCH, Germany) at a heating rate of 10° C/min; the thermal weight loss temperature Td which refers to the temperature in the case of 1% weight loss in a nitrogen atmosphere was measured on the TGA-50H thermogravimetric analyzer provided by Shimadzu Corporation with a nitrogen flow rate of 20 mL/min; the HOMO energy level was tested by the ionization energy test system (IPS3) in an atmospheric environment.

As can be seen from the data in the above table, compared with the currently used CBP and TPBi materials, the organic compound of the present invention has a high glass transition temperature, can improve the phase-state stability of the material film and further improve the service life of the device; the organic compound of the present invention has a high triplet energy level and can block the energy loss of the light-emitting layer, thereby improving the light-emitting efficiency of the device. Meanwhile, the material of the present invention and the applied material have similar HOMO energy levels. Therefore, the organic material with anthrone and N-containing heterocycle of the present invention can effectively improve the light-emitting efficiency and service life of an OLED device after being applied to different functional layers of the OLED device.

Hereinafter, the application effect of the OLED material synthesized in the present invention in the device will be described in detail through Device examples 1 to 22 and Device comparative example 1. Compared to Device example 1, Device examples 2 to 22 and Device comparative example 1 of the present invention have identical device fabricating processes, adopt the same substrate materials and electrode materials, and maintain consistency in film thickness of the electrode material, except that Device examples 2 to 15 replace the light-emitting layer material in the device; Device examples 16 to 22 replace the hole block layer or the electron transport layer material, and performance test results of the device in each example are as shown in Table 3.

Device Example 1

As shown in FIG. 1, an electroluminescent device was prepared by the steps of: a) cleaning an ITO anode layer 2 on a transparent substrate layer 1, ultrasonic cleaning in deionized water, acetone and alcohol each for 15 minutes, and then treating in a plasma cleaner for 2 minutes; b) vapor-depositing a hole injection layer material HAT-CN with a thickness of 10 nm on the ITO anode layer 2 by vacuum vapor deposition, wherein, this layer functions as a hole injection layer 3; c) vapor-depositing a hole transport material NPB with a thickness of 80 nm on the hole injection layer 3 by vacuum vapor deposition, wherein, this layer functions as a hole transport layer or electron block layer 4; d) vapor-depositing a light-emitting layer 5 with a thickness of 40 nm on the hole transport layer or electron block layer 4, wherein, compound 3 of the present functions and compound GH function as the host material, Ir(ppy)$_3$ functions as a doping material, and a mass ratio of the compound 3 to GH to Ir(ppy)$_3$ is 50:50:10; e) vapor-depositing an electron transport material TPBI with a thickness of 35 nm on the light-emitting layer 5 by vacuum vapor deposition, wherein, this organic material layer is used as a hole block or electron transport layer 6; f) vapor-depositing an electron injection layer LiF with a thickness of 1 nm by vacuum vapor deposition on the hole block or electron transport layer 6, wherein, this layer functions as an electron injection layer 7; g) vapor-depositing a cathode Al (100 nm) on the electron injection layer 7 by vacuum vapor deposition, and this layer is a cathode reflective electrode layer 8. After completing the fabrication of the electroluminescent device according to the above steps, the driving voltage and current efficiency of the device were measured, and the results are shown in Table 3. Molecular structural formulas of related materials are as shown below:

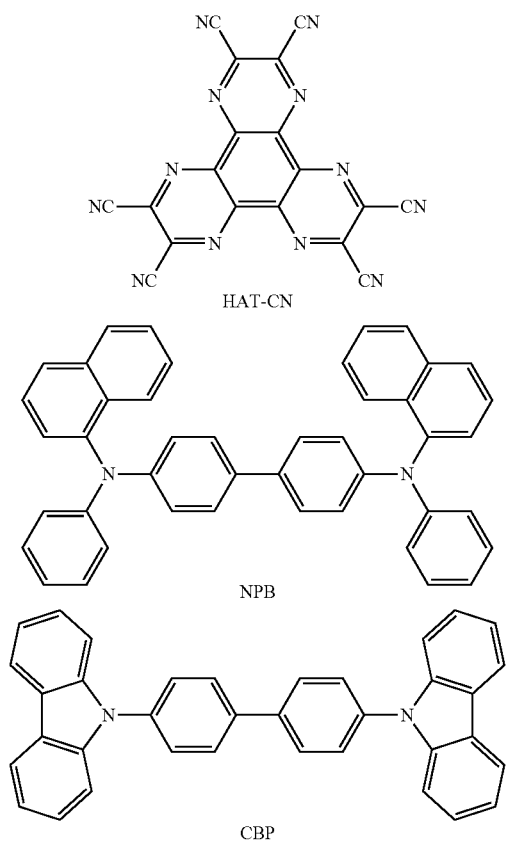

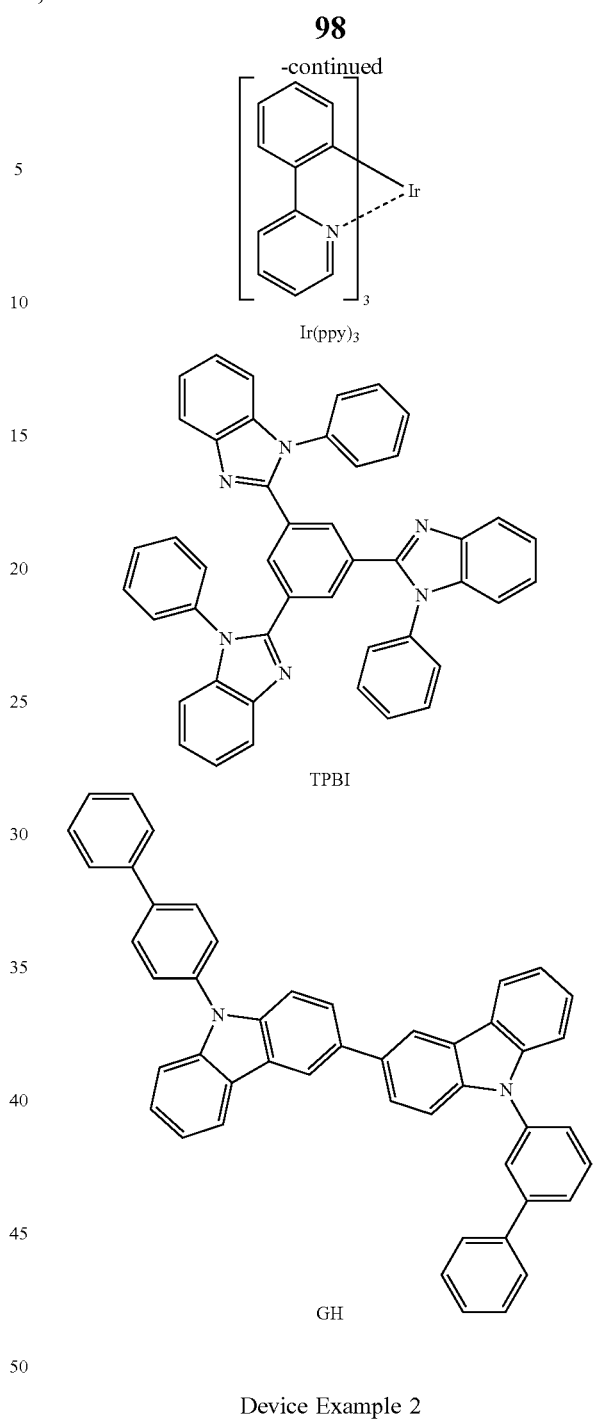

Device Example 2

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 10, GH and Ir(ppy)$_3$ mixed in a weight ratio of 40:60:10)/hole block or electron transport layer 6 (thickness: 35 nm, material: TPBI)/electron injection layer 7 (thickness: 1 nm, material: LiF)/Al (thickness: 100 nm).

Device Example 3

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 11, GH and Ir(ppy)$_3$ mixed in a weight ratio of 60:40:10)/hole block or electron transport layer 6 (thickness: 35 nm, material: TPBI)/electron injection layer 7 (thickness: 1 nm, material: LiF)/Al (thickness: 100 nm).

Device Example 4

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 20, GH and Ir(ppy)$_3$ mixed in a weight ratio of 70:30:10)/hole block or electron transport layer 6 (thickness: 35 nm, material: TPBI)/electron injection layer 7 (thickness: 1 nm, material: LiF)/Al (thickness: 100 nm).

Device Example 5

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 27, GH and Ir(ppy)$_3$ mixed in a weight ratio of 60:40:10)/hole block or electron transport layer 6 (thickness: 35 nm, material: TPBI)/electron injection layer 7 (thickness: 1 nm, material: LiF)/Al (thickness: 100 nm).

Device Example 6

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 35 and Ir(ppy)$_3$ mixed in a weight ratio of 90:10)/hole block or electron transport layer 6 (thickness: 35 nm, material: TPBI)/electron injection layer 7 (thickness: 1 nm, material: LiF)/Al (thickness: 100 nm).

Device Example 7

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 44 and Ir(ppy)$_3$ mixed in a weight ratio of 90:10)/hole block or electron transport layer 6 (thickness: 35 nm, material: TPBI)/electron injection layer 7 (thickness: 1 nm, material: LiF)/Al (thickness: 100 nm).

Device Example 8

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 59, GH and Ir(ppy)$_3$ mixed in a weight ratio of 50:50:10)/hole block or electron transport layer 6 (thickness: 35 nm, material: TPBI)/electron injection layer 7 (thickness: 1 nm, material: LiF)/Al (thickness: 100 nm).

Device Example 9

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 69, GH and Ir(ppy)$_3$ mixed in a weight ratio of 50:50:10)/hole block or electron transport layer 6 (thickness: 35 nm, material: TPBI)/electron injection layer 7 (thickness: 1 nm, material: LiF)/Al (thickness: 100 nm).

Device Example 10

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 95, GH and Ir(ppy)$_3$ mixed in a weight ratio of 50:50:10)/hole block or electron transport layer 6 (thickness: 35 nm, material: TPBI)/electron injection layer 7 (thickness: 1 nm, material: LiF)/Al (thickness: 100 nm).

Device Example 11

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 104, GH and Ir(ppy)$_3$ mixed in a weight ratio of 60:40:10)/hole block or electron transport layer 6 (thickness: 35 nm, material: TPBI)/electron injection layer 7 (thickness: 1 nm, material: LiF)/Al (thickness: 100 nm).

Device Example 12

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 113, GH and Ir(ppy)$_3$ mixed in a weight ratio of 70:30:10)/hole block or electron transport layer 6 (thickness: 35 nm, material: TPBI)/electron injection layer 7 (thickness: 1 nm, material: LiF)/Al (thickness: 100 nm).

Device Example 13

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 128, GH and Ir(ppy)$_3$ mixed in a weight ratio of 50:50:10)/hole block or electron transport layer 6 (thickness: 35 nm, material: TPBI)/electron injection layer 7 (thickness: 1 nm, material: LiF)/Al (thickness: 100 nm).

Device Example 14

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 153, GH and Ir(ppy)$_3$ mixed in a weight ratio of 50:50:10)/hole block or electron transport layer 6 (thickness: 35 nm, material: TPBI)/electron injection layer 7 (thickness: 1 nm, material: LiF)/Al (thickness: 100 nm).

Device Example 15

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: compound 167, GH and Ir(ppy)$_3$ mixed in a weight ratio of 40:60:10)/hole block or electron transport layer 6 (thickness: 35 nm, material: TPBI)/electron injection layer 7 (thickness: 1 nm, material: LiF)/Al (thickness: 100 nm).

Device Example 16

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 50)/electron injection layer 7 (thickness: 1 nm, material: LiF)/Al (thickness: 100 nm).

Device Example 17

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 79)/electron injection layer 7 (thickness: 1 nm, material: LiF)/Al (thickness: 100 nm).

Device Example 18

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 80)/electron injection layer 7 (thickness: 1 nm, material: LiF)/Al (thickness: 100 nm).

Device Example 19

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 89)/electron injection layer 7 (thickness: 1 nm, material: LiF)/Al (thickness: 100 nm).

Device Example 20

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 119)/electron injection layer 7 (thickness: 1 nm, material: LiF)/Al (thickness: 100 nm).

Device Example 21

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 126)/electron injection layer 7 (thickness: 1 nm, material: LiF)/Al (thickness: 100 nm).

Device Example 22

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: compound 139)/electron injection layer 7 (thickness: 1 nm, material: LiF)/Al (thickness: 100 nm).

Device Comparative Example 1

ITO anode layer 2 (thickness: 150 nm)/hole injection layer 3 (thickness: 10 nm, material: HAT-CN)/hole transport layer 4 (thickness: 80 nm, material: NPB)/light-emitting layer 5 (thickness: 40 nm, material: CBP and Ir(ppy)$_3$ mixed in a weight ratio of 90:10)/hole block or electron transport layer 6 (thickness: 35 nm, material: TPBI)/electron injection Layer 7 (thickness: 1 nm, material: LiF)/Al (thickness: 100 nm). The measured data of the electroluminescent device obtained is as shown in Table 3.

TABLE 3

| No. | Current efficiency (cd/A) | Color | LT95 life (Hr) @ 5000 nits |
| --- | --- | --- | --- |
| Device example 1 | 46.4 | Green light | 27.3 |
| Device example 2 | 45.5 | Green light | 26.5 |
| Device example 3 | 46.7 | Green light | 25.1 |
| Device example 4 | 45.9 | Green light | 25.7 |
| Device example 5 | 45.4 | Green light | 25.5 |
| Device example 6 | 36.9 | Green light | 27.6 |
| Device example 7 | 37.1 | Green light | 27.1 |
| Device example 8 | 42.9 | Green light | 25.6 |
| Device example 9 | 45.5 | Green light | 27.3 |
| Device example 10 | 45.7 | Green light | 25.1 |
| Device example 11 | 47.1 | Green light | 27.2 |
| Device example 12 | 46.3 | Green light | 25.9 |
| Device example 13 | 47.9 | Green light | 25.3 |
| Device example 14 | 45.1 | Green light | 26.1 |
| Device example 15 | 46.5 | Green light | 26.2 |
| Device example 16 | 36.3 | Green light | 35.3 |
| Device example 17 | 35.9 | Green light | 33.4 |
| Device example 18 | 36.5 | Green light | 32.1 |
| Device example 19 | 35.3 | Green light | 32.8 |
| Device example 20 | 38.1 | Green light | 33.9 |
| Device example 21 | 37.3 | Green light | 37.8 |
| Device example 22 | 36.4 | Green light | 32.0 |
| Device comparative example 1 | 28 | Green light | 10.5 |

As can be seen from the results in Table 3, the organic compound of the present invention can be applied to the fabrication of OLED light-emitting devices, and compared with the comparative examples, the organic compound of the present invention is greatly improved in both the efficiency and the life over the known OLED materials, especially the service life of the devices is improved greatly. Further, the OLED device prepared using the material of the present invention can maintain a long life at a high temperature. Device examples 1 to 22 and Device comparative example 1 were subjected to a high-temperature driving life test at 85° C. The results are shown in Table 4.

TABLE 4

| Device No.: | High-temperature LT95 life |
|---|---|
| Device example 1 | 22.8 |
| Device example 2 | 20.7 |
| Device example 3 | 22.1 |
| Device example 4 | 23.3 |
| Device example 5 | 22.5 |
| Device example 6 | 23.3 |
| Device example 7 | 23 |
| Device example 8 | 22.7 |
| Device example 9 | 21.9 |
| Device example 10 | 23.6 |
| Device example 11 | 23.7 |
| Device example 12 | 24.1 |
| Device example 13 | 22.7 |
| Device example 14 | 21.2 |
| Device example 15 | 22.0 |
| Device example 16 | 27.5 |
| Device example 17 | 29.7 |
| Device example 18 | 28.6 |
| Device example 19 | 29.4 |
| Device example 20 | 30.6 |
| Device example 21 | 29.9 |
| Device example 22 | 29.4 |
| Device comparative example 1 | 0.7 |

As can be seen from the results in Table 4, Device examples 1 to 22 disclose device structures using both the material of the present invention and known materials. Compared with Device comparative example 1, at a high temperature, the OLED device provided by the present invention has a very good driving life.

Further, the efficiency of the OLED device prepared by using the material of the present invention is relatively stable when operating at a low temperature. Device examples 2, 10 and 18 and Device comparative example 1 were tested for efficiency in the range of −10° C. to 80° C. The results are shown in Table 5 and the FIG. 2.

TABLE 5

| Current efficiency (cd/A) | Temperature (° C.) | | | | | | | | | |
|---|---|---|---|---|---|---|---|---|---|---|
| | −10 | 0 | 10 | 20 | 30 | 40 | 50 | 60 | 70 | 80 |
| Device example 2 | 43.3 | 44.4 | 45.1 | 45.5 | 46.2 | 46.7 | 48.1 | 47.4 | 46.6 | 46.9 |
| Device example 10 | 43.6 | 44.2 | 44.8 | 45.7 | 46.3 | 47.0 | 47.9 | 47.7 | 47.0 | 47.5 |
| Device example 18 | 34.4 | 35.2 | 35.7 | 36.5 | 37.2 | 37.7 | 38.0 | 38.2 | 37.8 | 37.4 |
| Device comparative example 1 | 23.5 | 25.1 | 27.1 | 28.0 | 28.5 | 28.9 | 28.9 | 27.1 | 25.3 | 22.4 |

Figure 2:
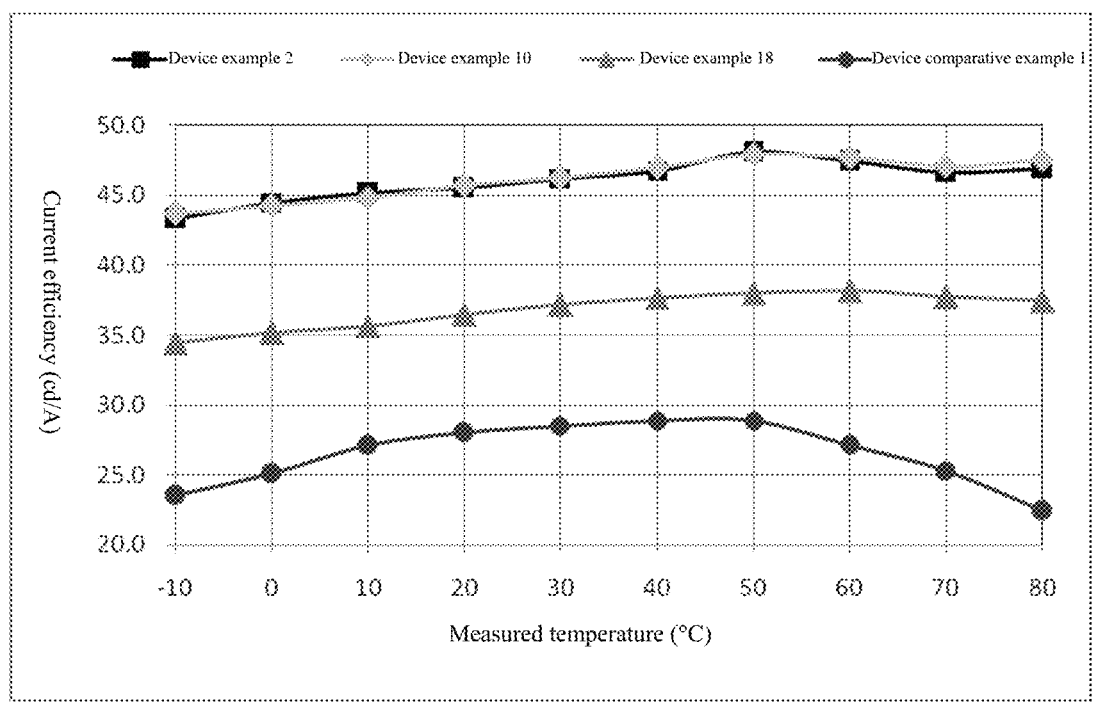
FIG. 2 is the efficiency curve of the device according to examples of the present invention measured at different temperatures.

As can be seen from the results in Table 5 and FIG. 2, Device examples 2, 10 and 18 disclose device structures using both the material of the present invention and known materials. Compared with Device comparative example 1, these Device examples have higher low-temperature efficiency, and also have the efficiency increased steadily during the temperature rise.

To sum up, the embodiments mentioned above are merely preferred embodiments of the present invention and not intended to limit the present invention. Any of modifications, equivalent substitutions and improvements, etc. made within the spirit and principle of the present invention shall be covered in the protection scope of the present invention.

What is claimed is:

1. A compound, wherein a structure of the compound is any one of:

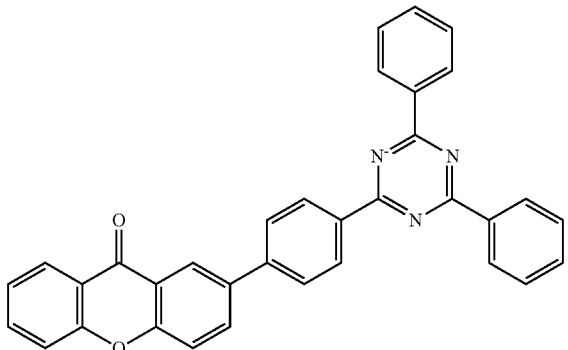

(1)

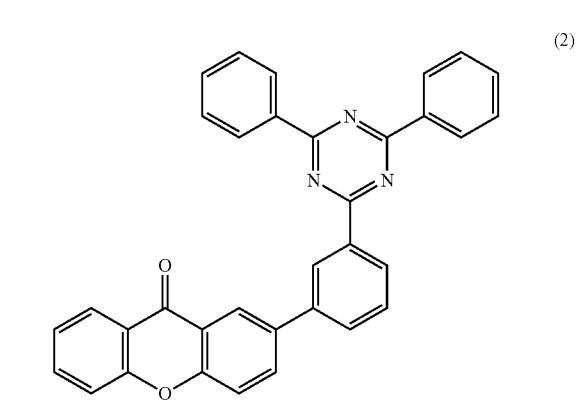

(2)

-continued

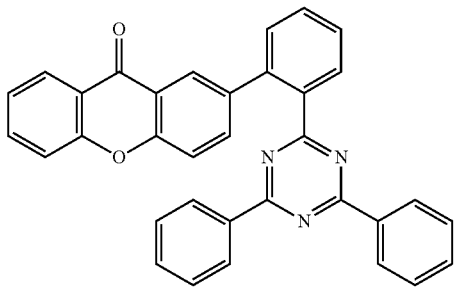

(3)

(4)
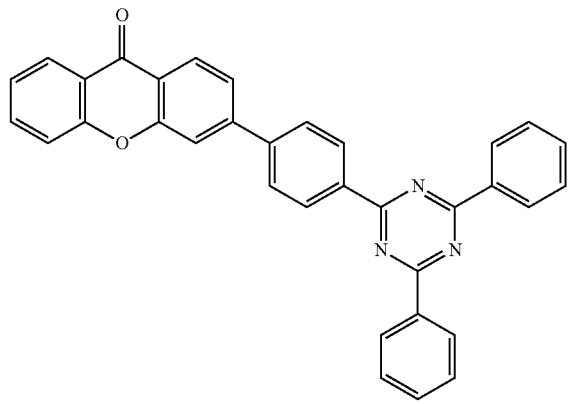
(5)
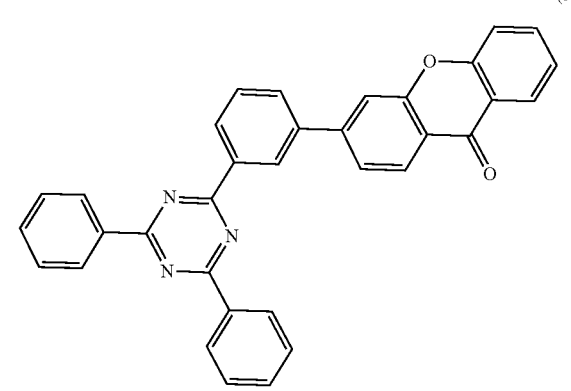
(6)
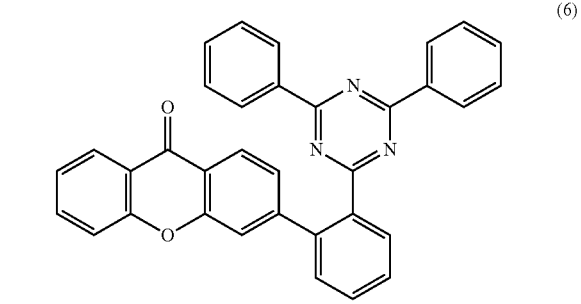
(7)
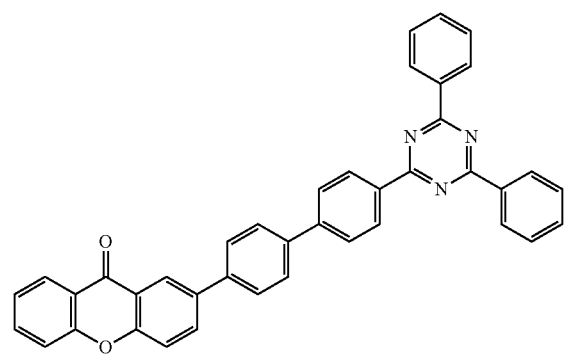
(8)
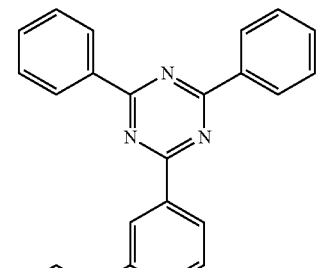
(9)
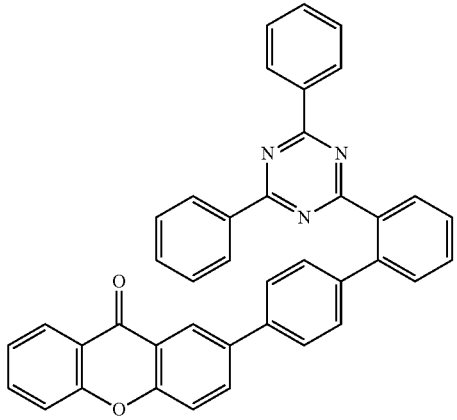
(10)
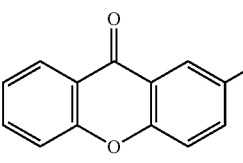

-continued
(11)
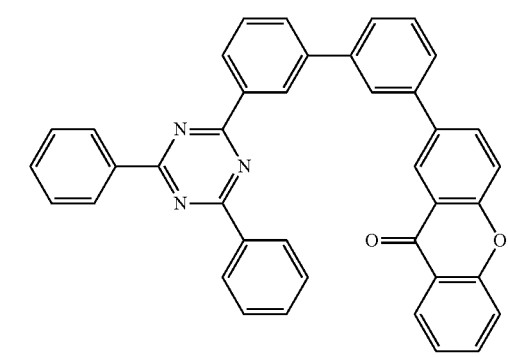
(12)
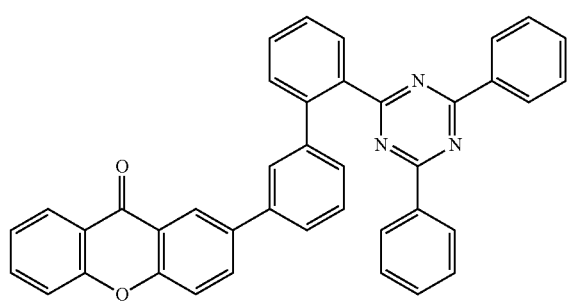
(13)
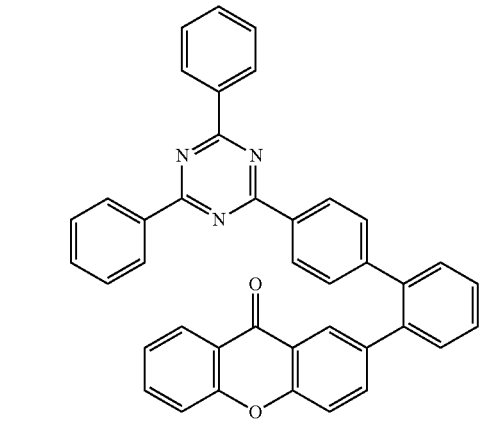
(14)
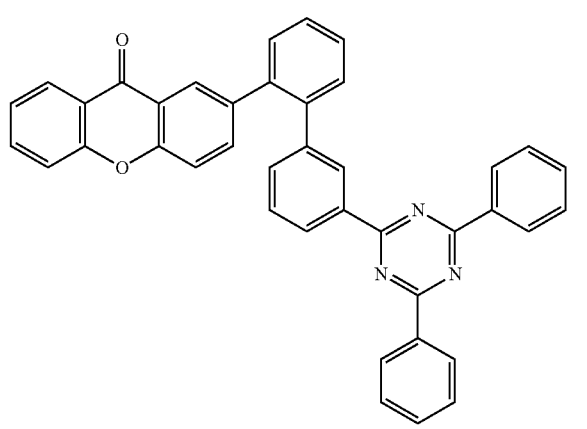
-continued
(15)
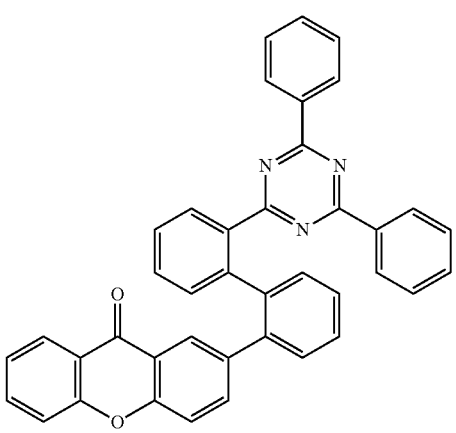
(16)
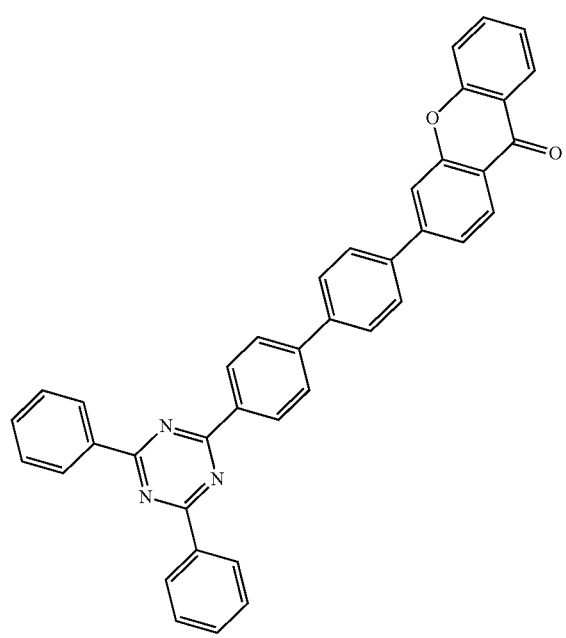
(17)
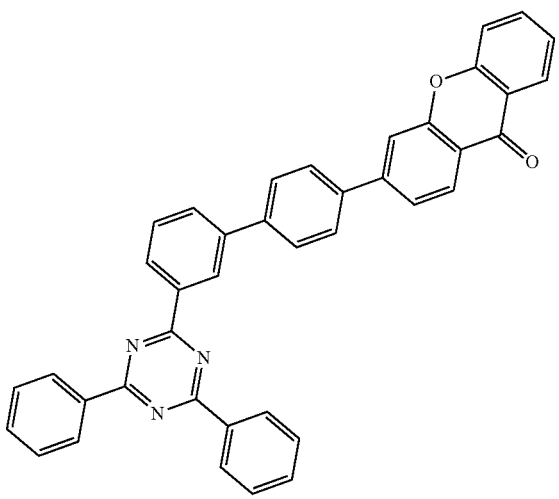

(18)
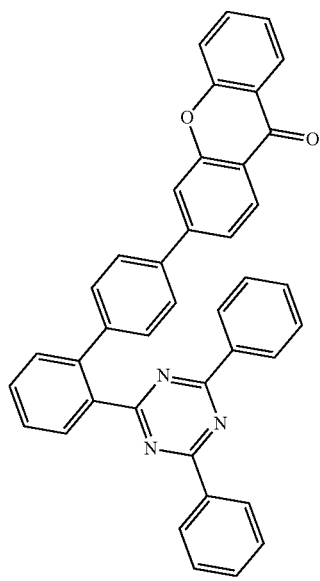
(21)
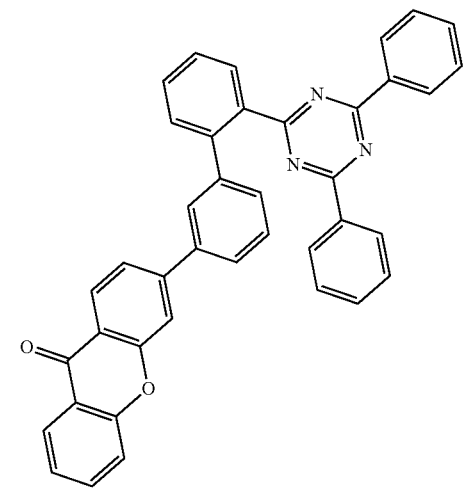
(19)
(22)
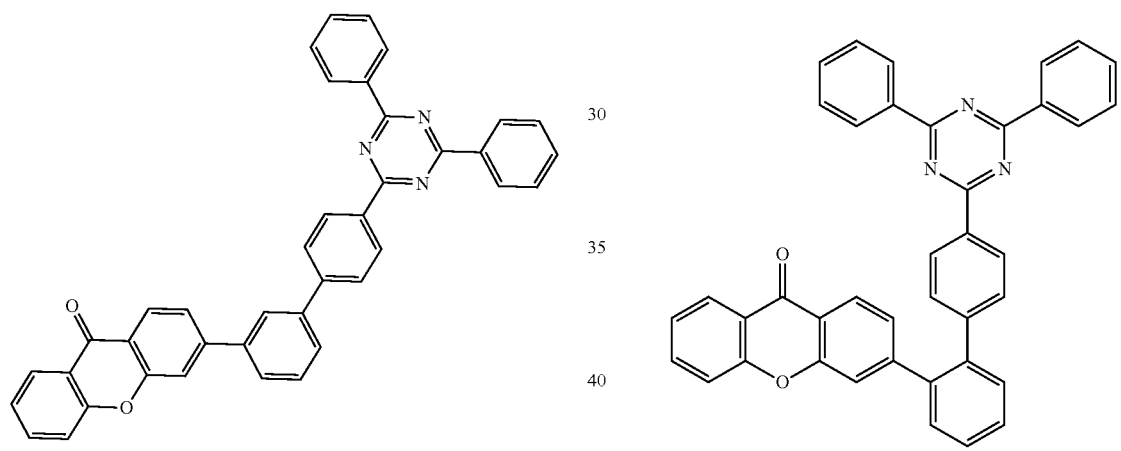
(20)
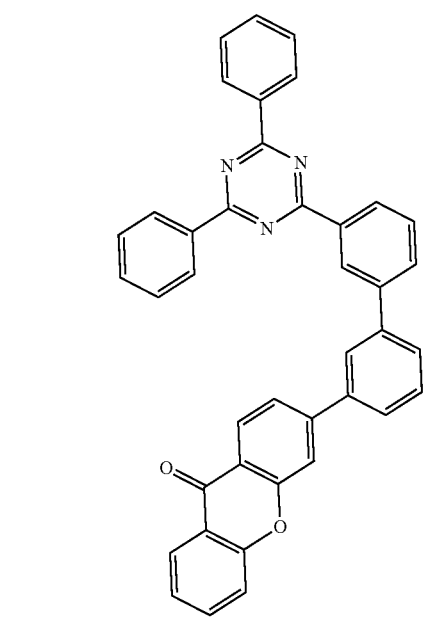
(23)
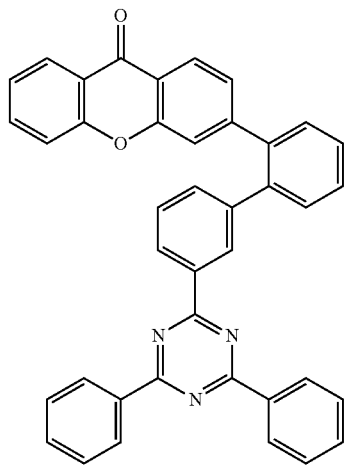

(24)
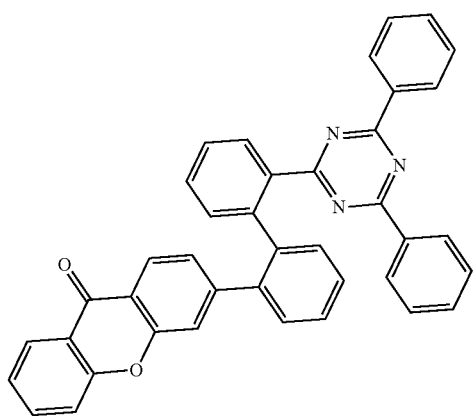
(28)
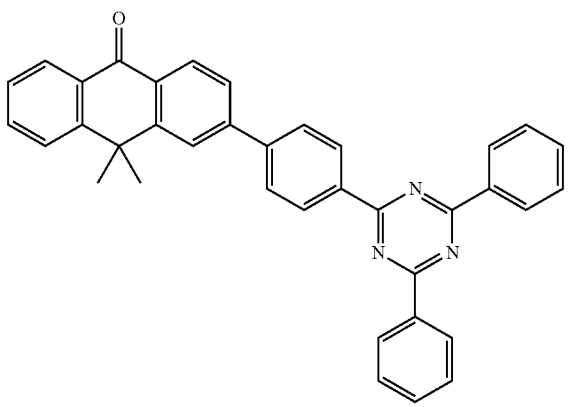
(25)
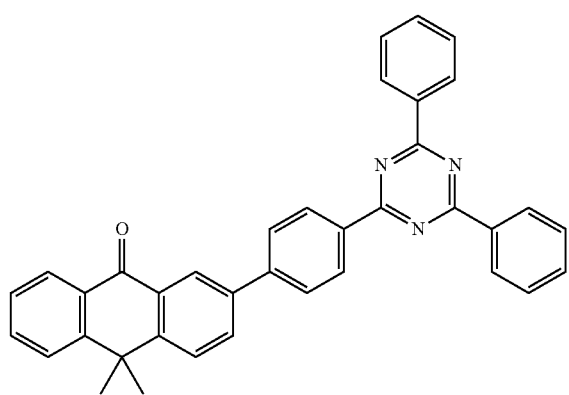
(29)
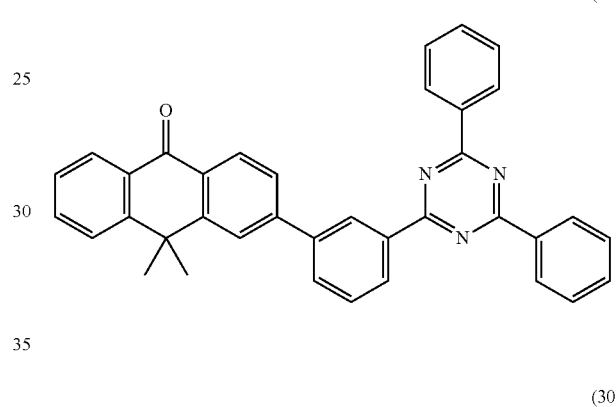
(26)
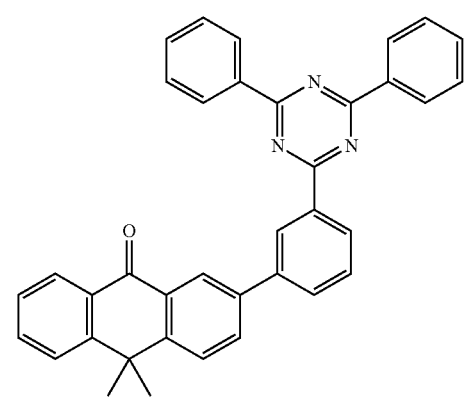
(30)
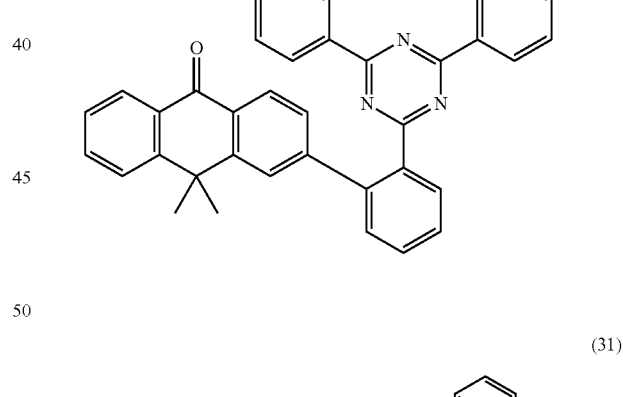
(27)
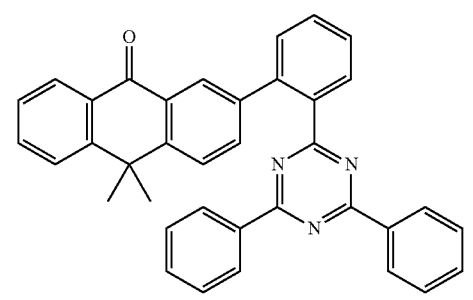
(31)
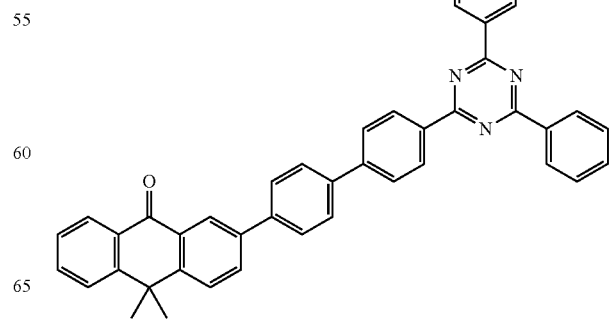

(32)
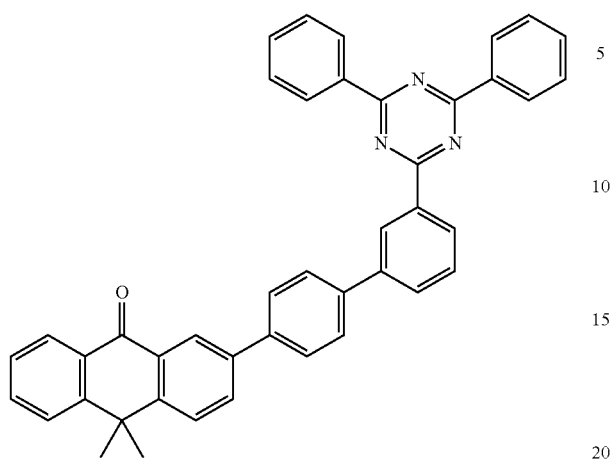
(35)
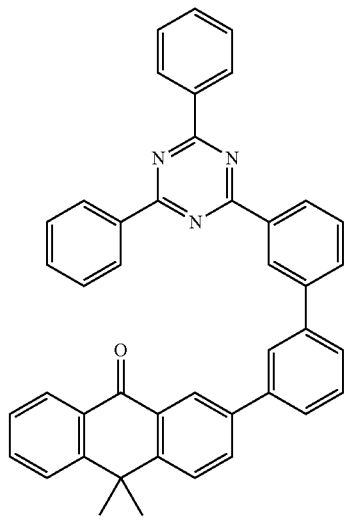
(33)
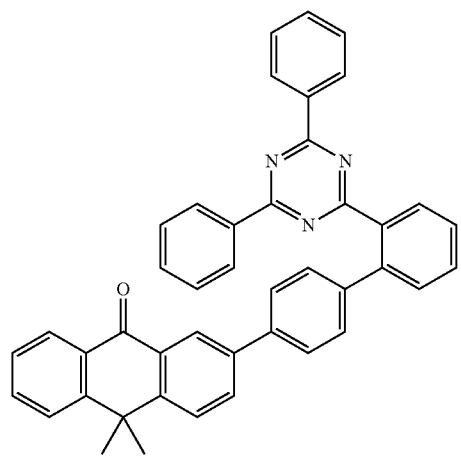
(36)
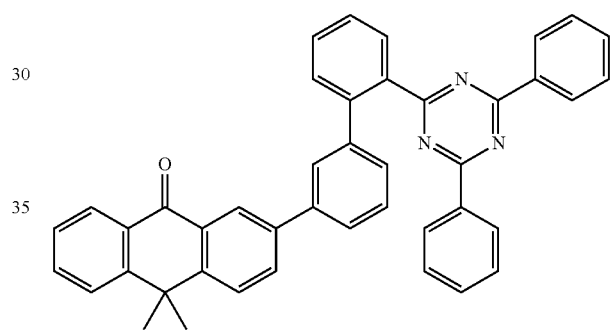
(34)
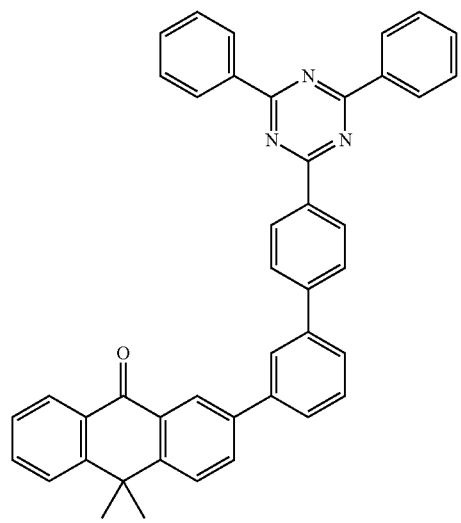
(37)
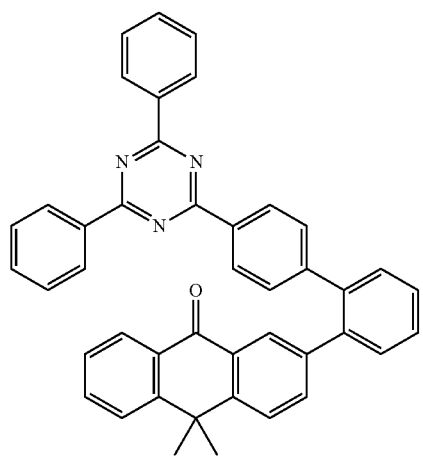

-continued
(38)
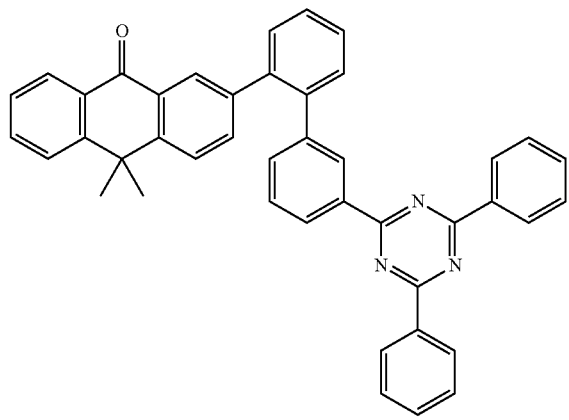
(39)
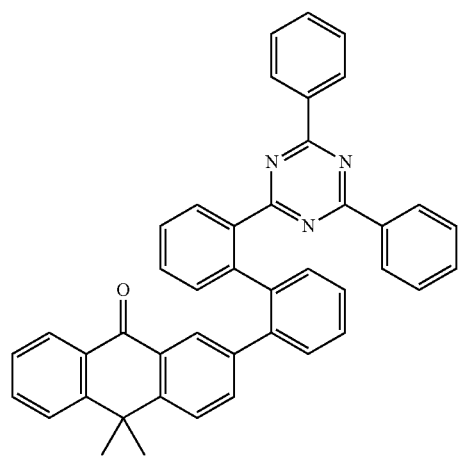
(40)
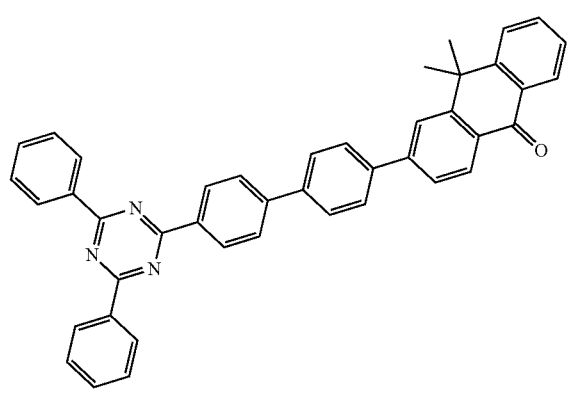
-continued
(41)
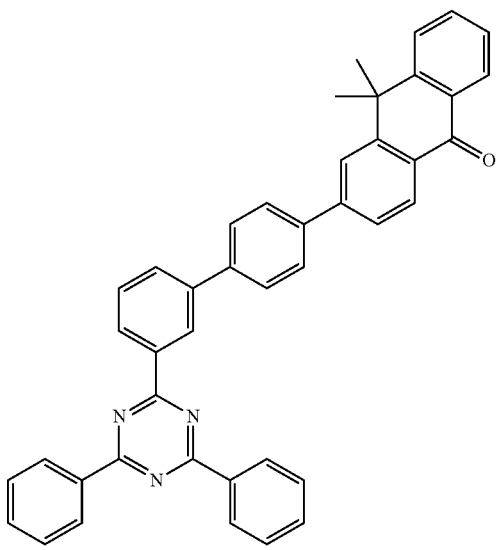
(42)
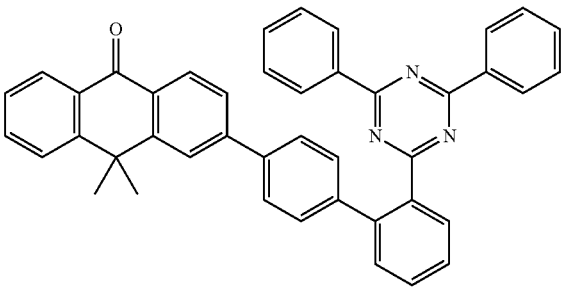
(43)
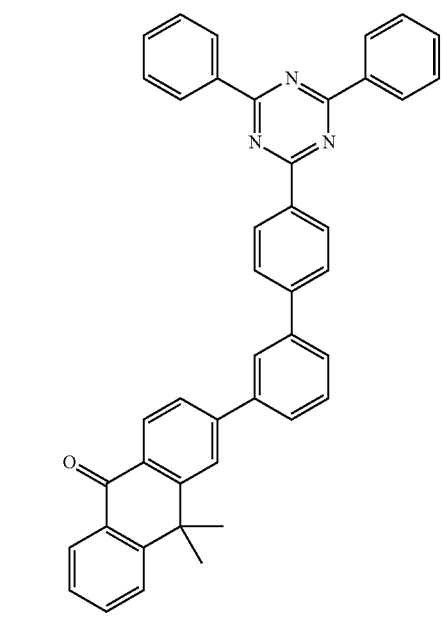

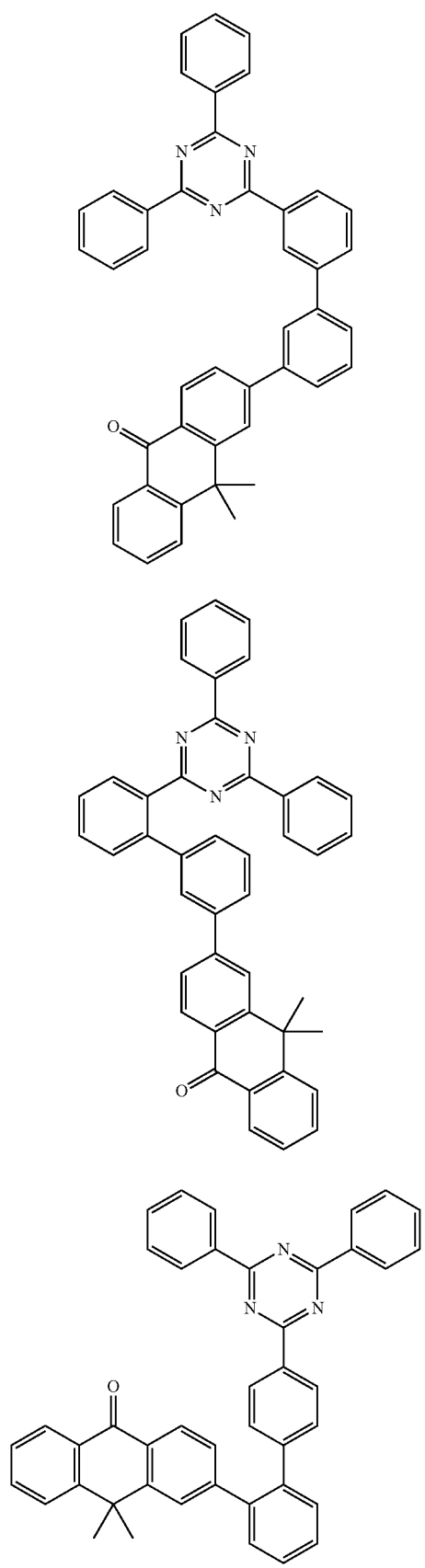
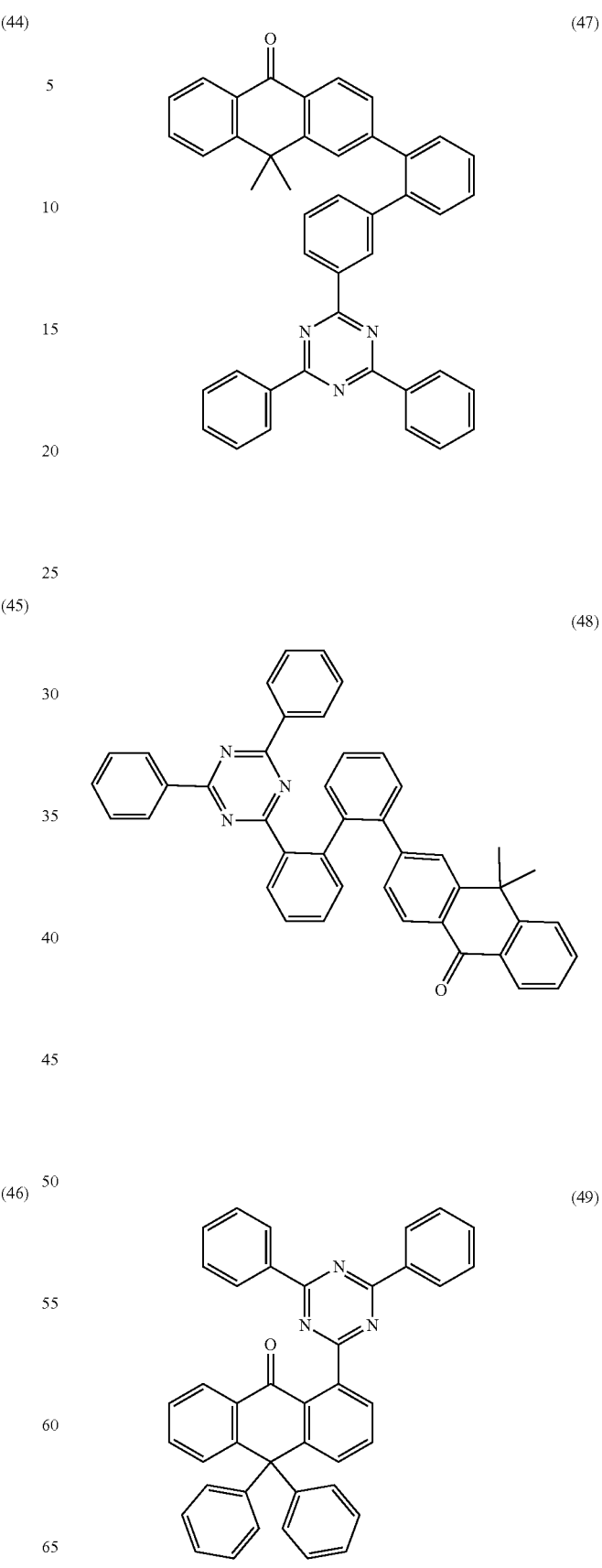

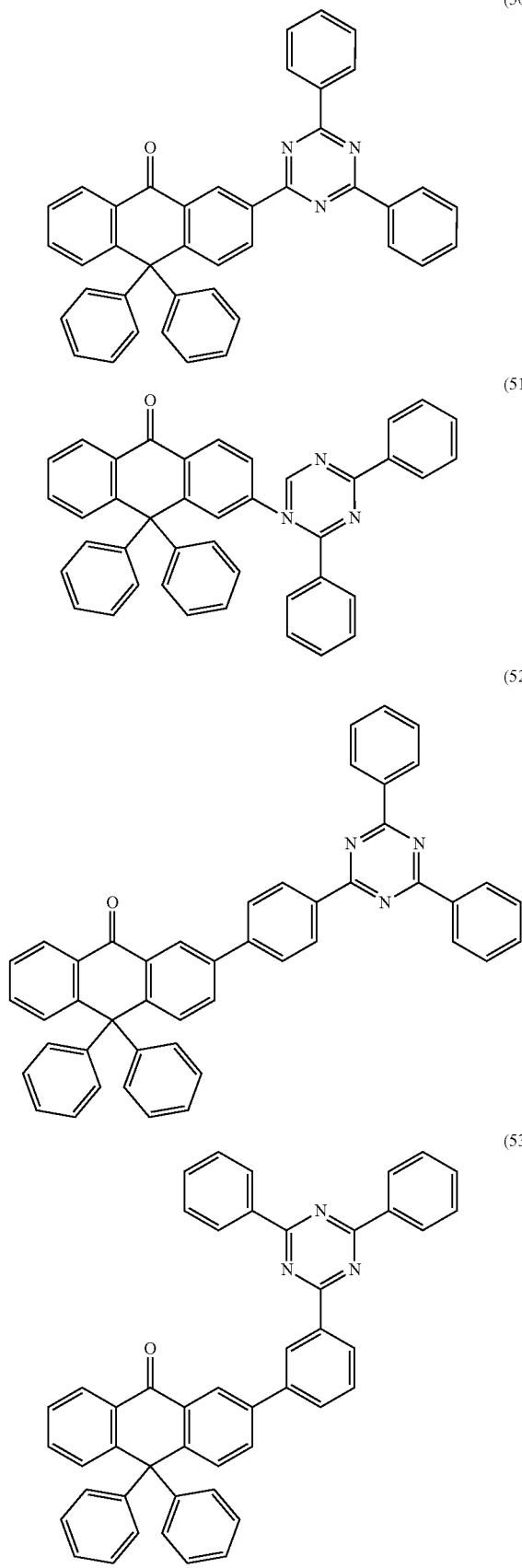
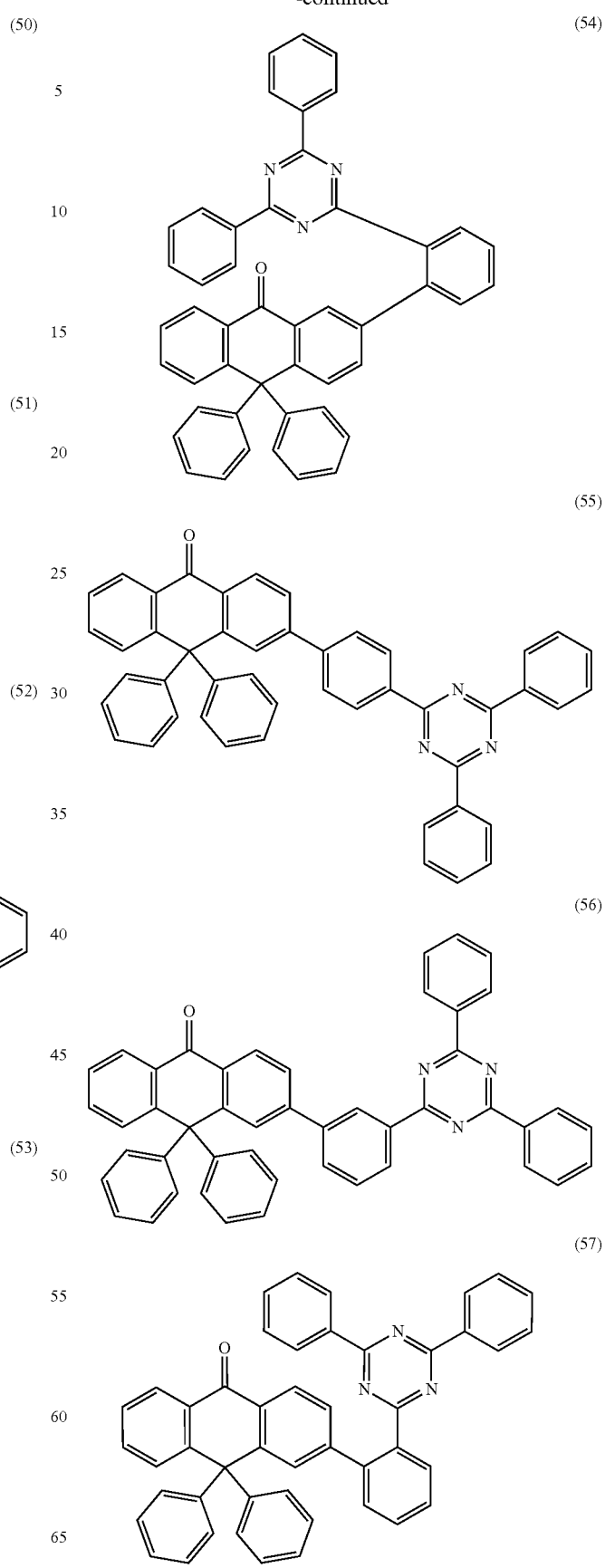

(58)
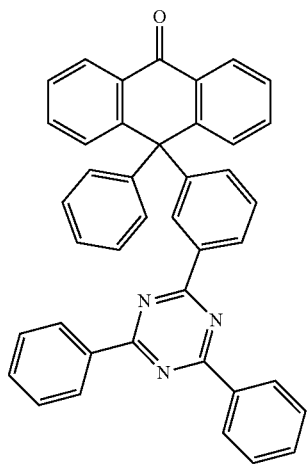
(59)
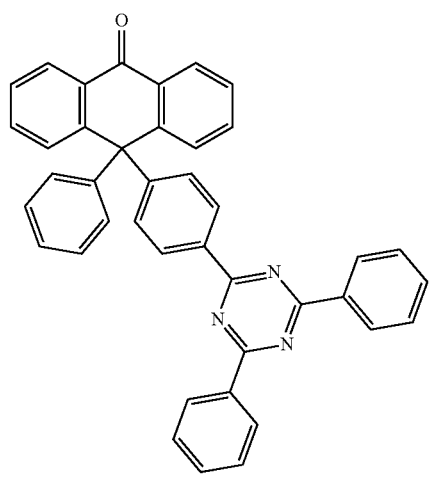
(60)
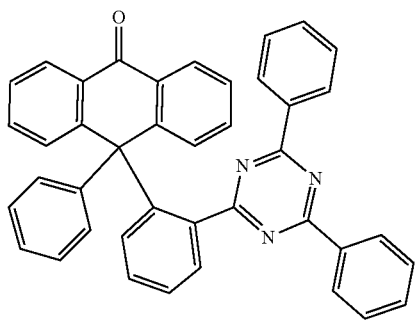
(61)
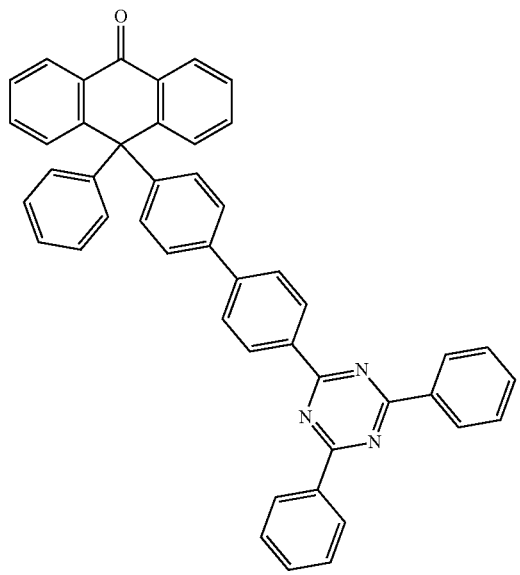
(62)
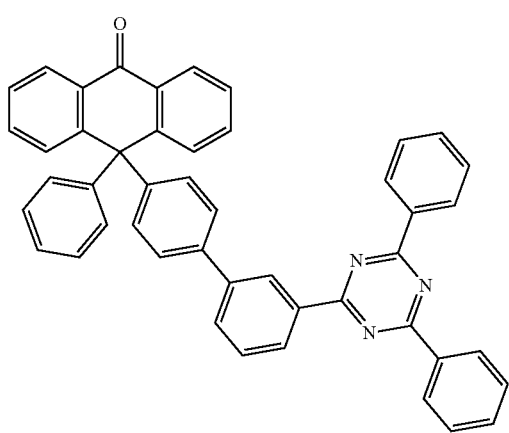
(63)
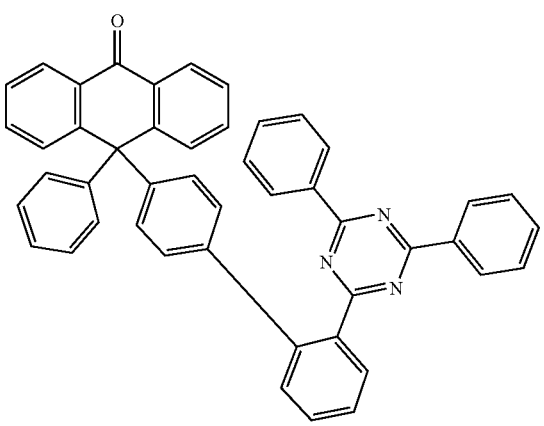

-continued
(64)
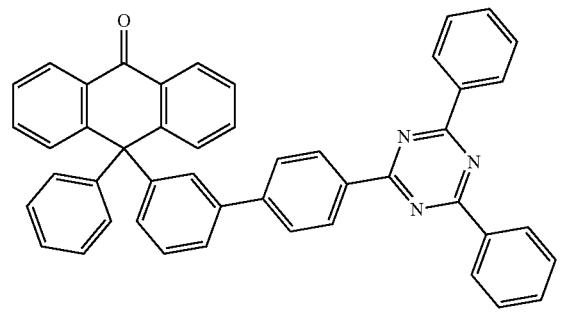
(65)
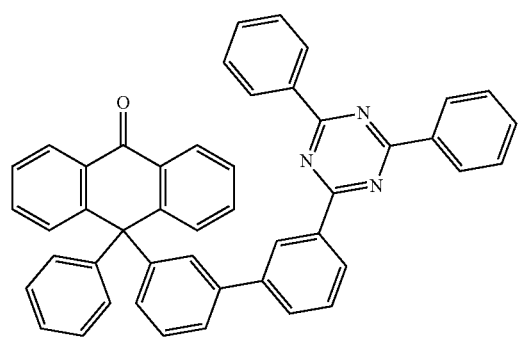
(66)
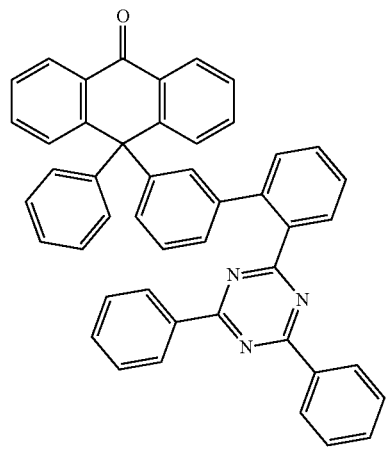
(67)
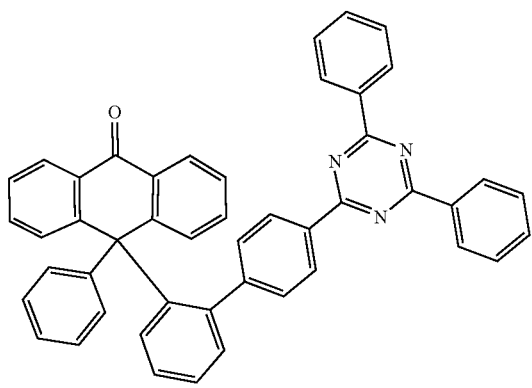
-continued
(68)
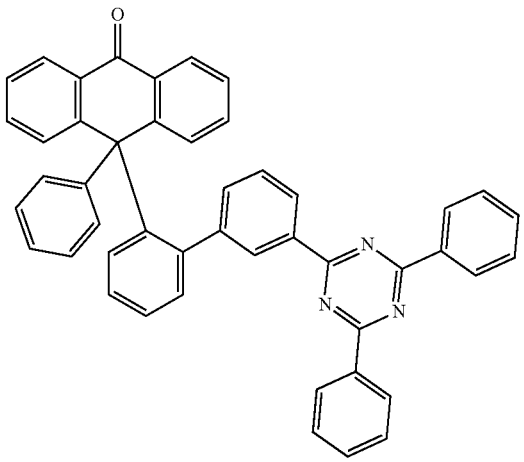
(69)
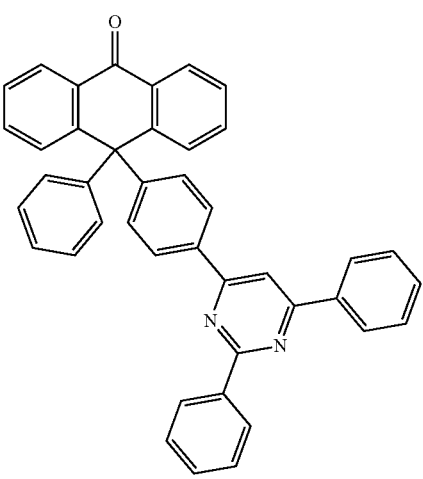
(70)
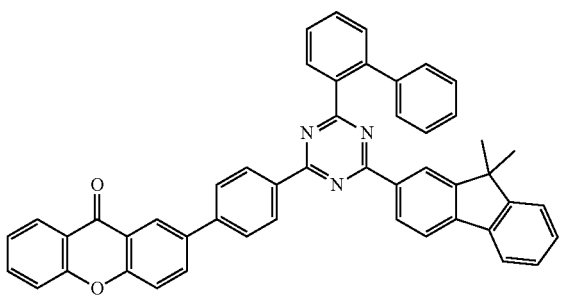
(71)
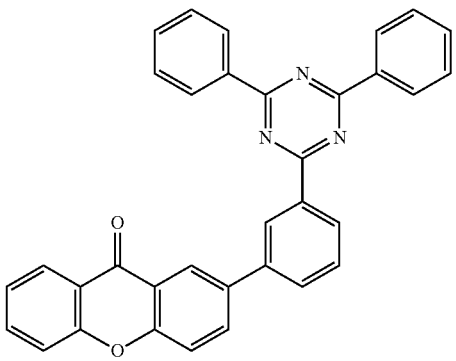

(72)
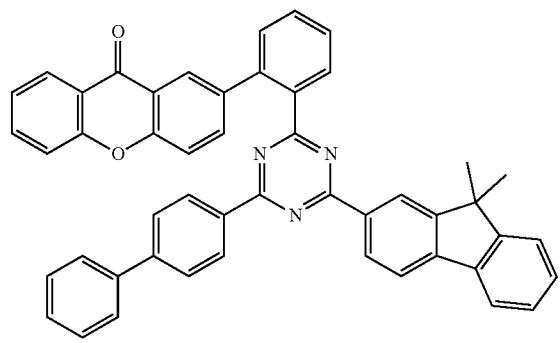
(73)
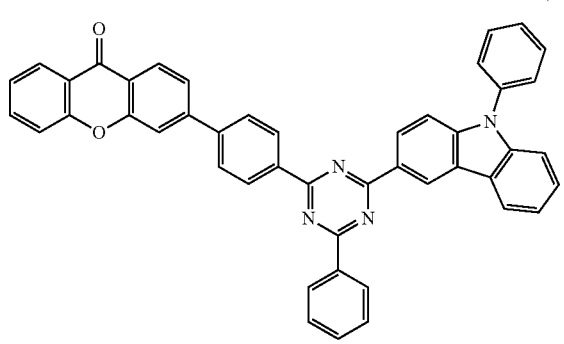
(74)
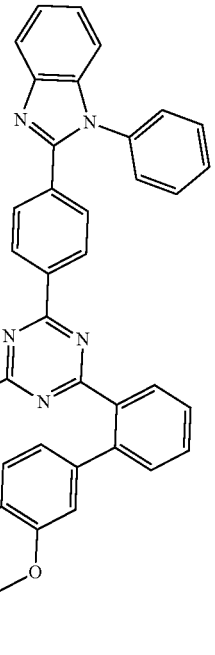
(75)
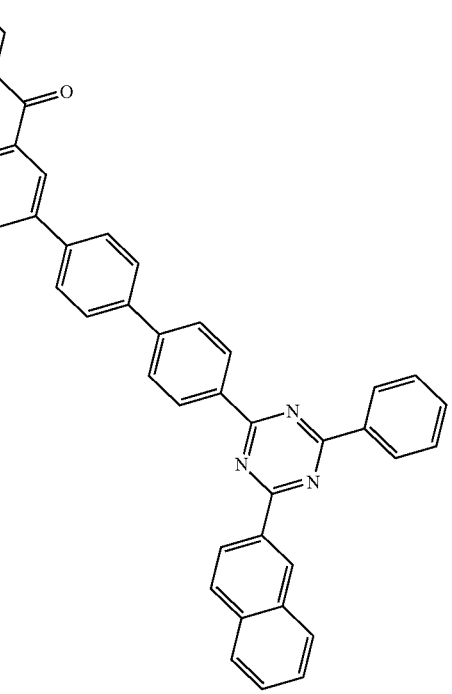
(76)

(77)
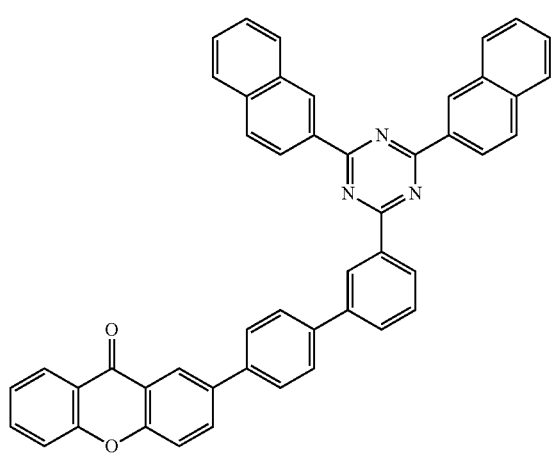
(78)
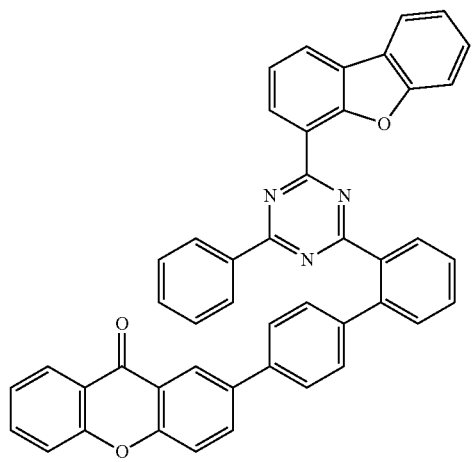
(79)
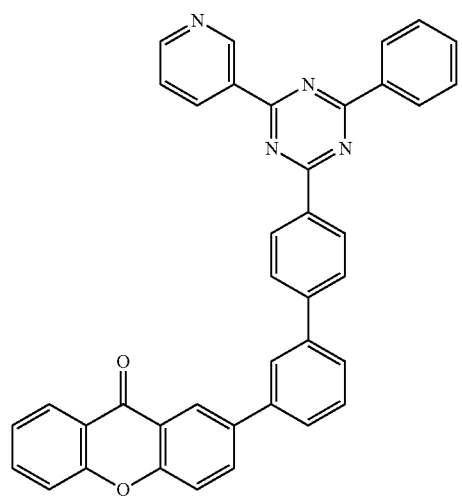
(80)
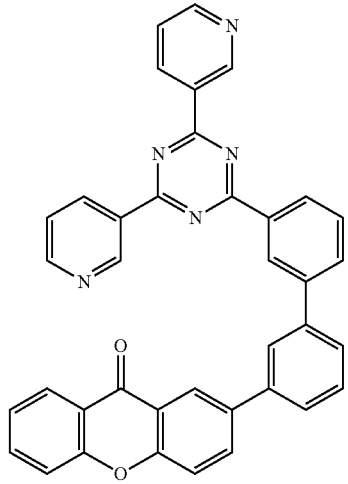
(81)
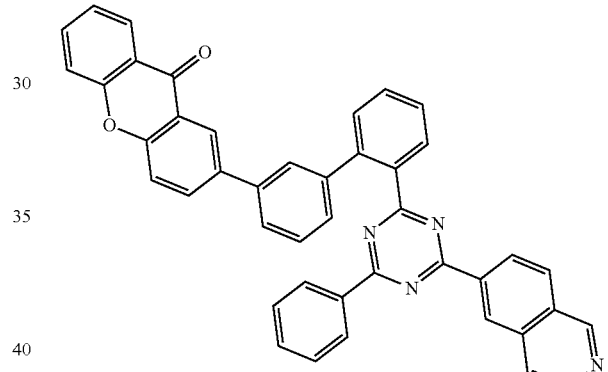
(82)
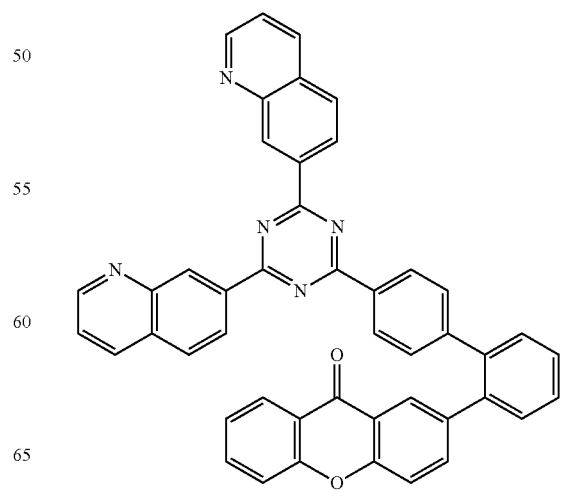

(83)
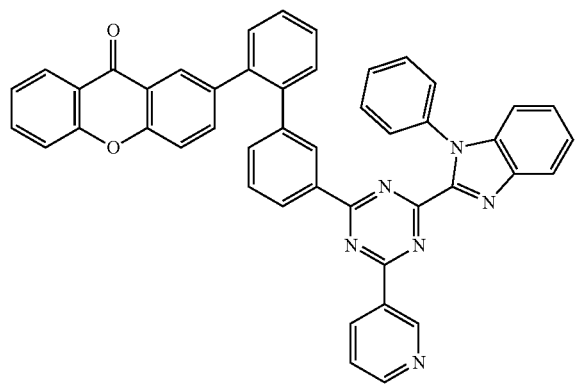
(84)
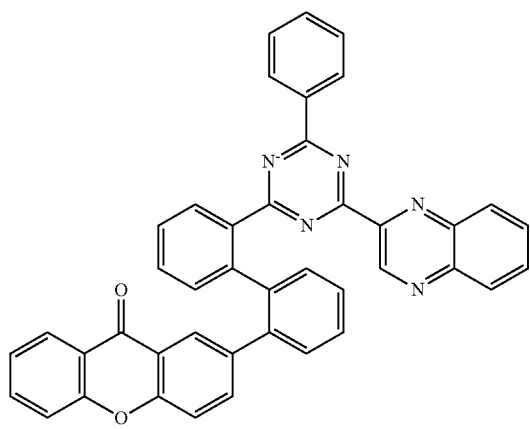
(85)
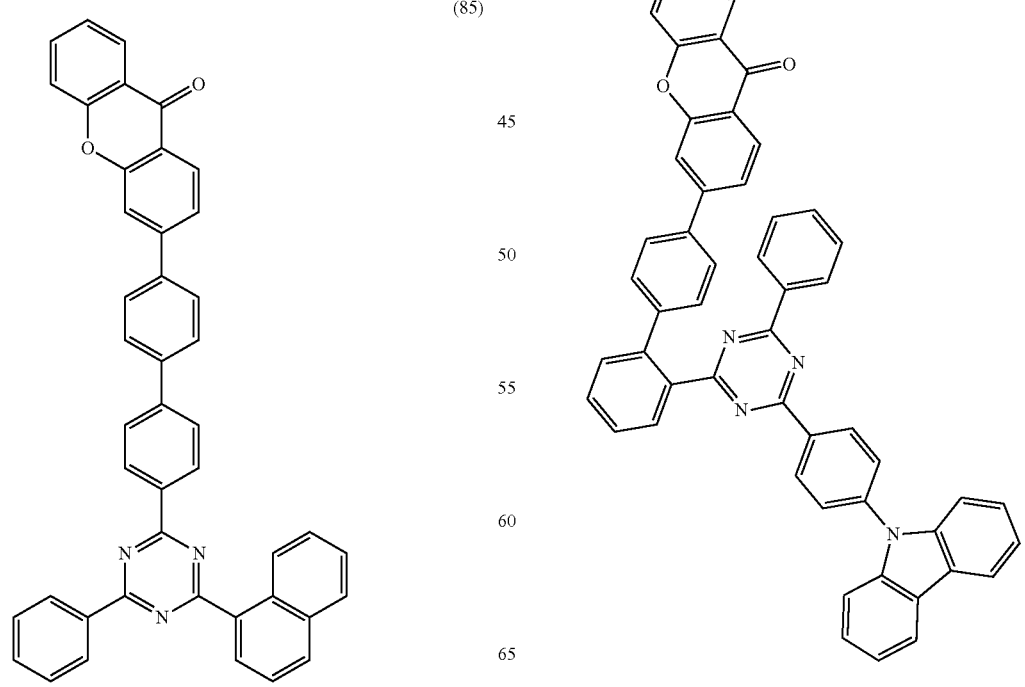
(86)
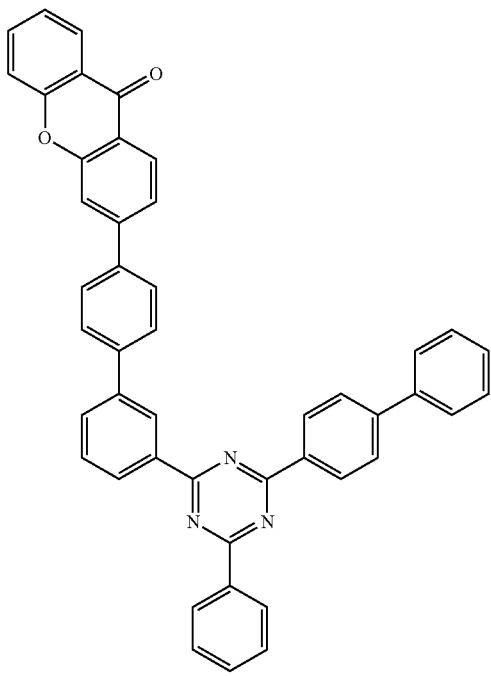
(87)

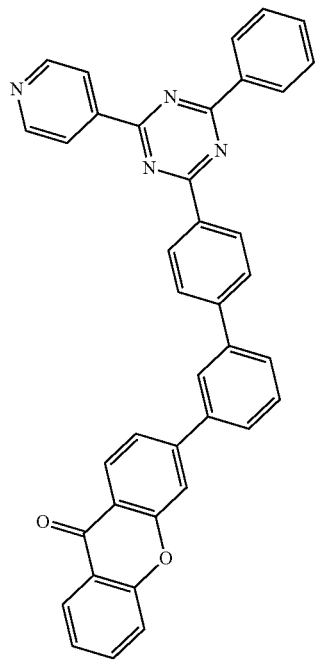
(88)
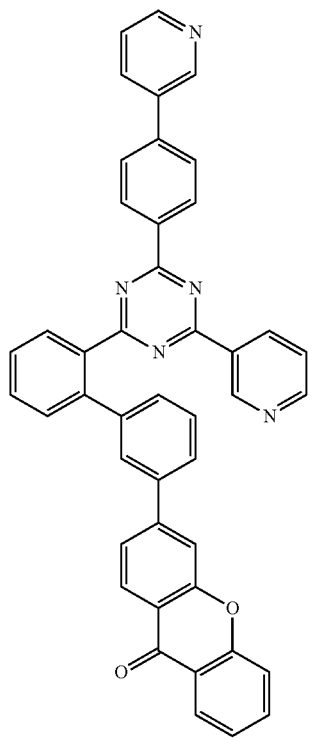
(90)
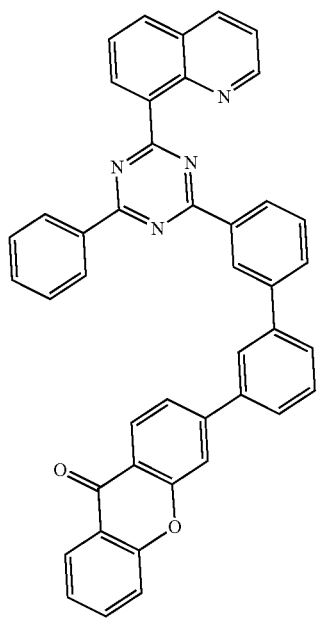
(89)
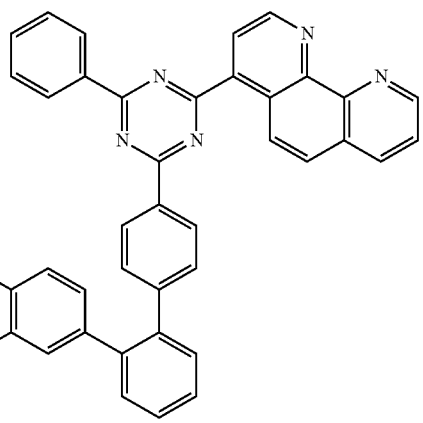
(91)

(92)
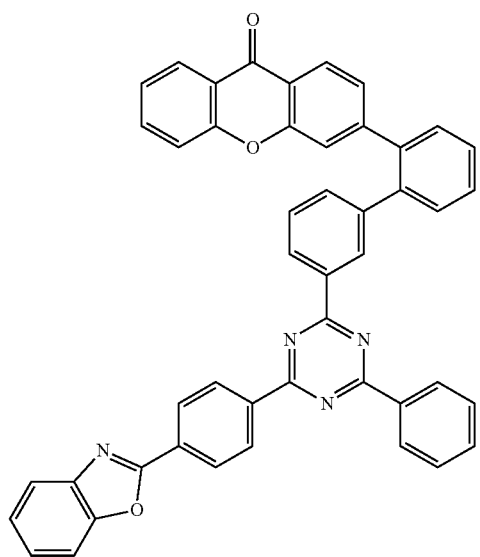
(93)
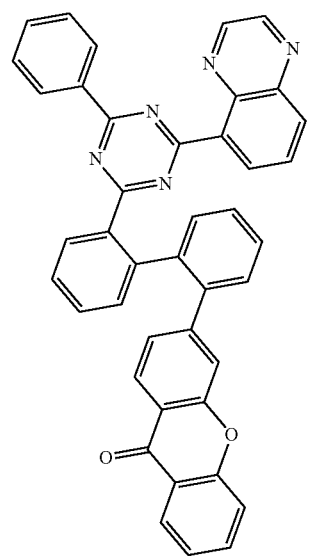
(94)
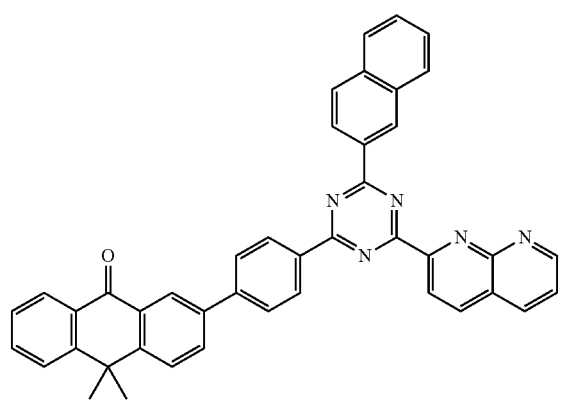
(95)
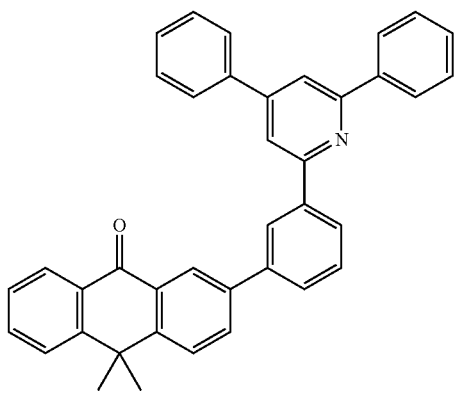
(96)
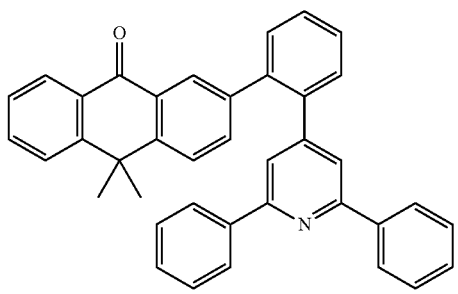
(97)
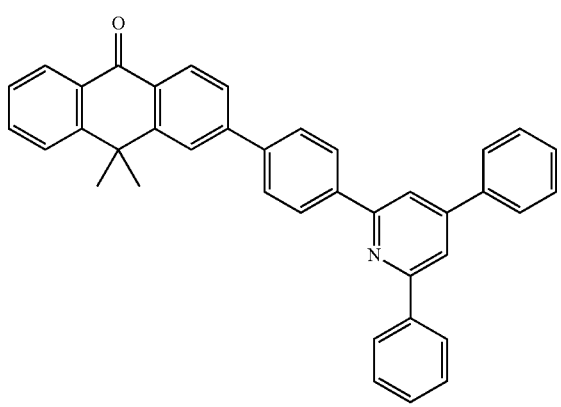
(98)
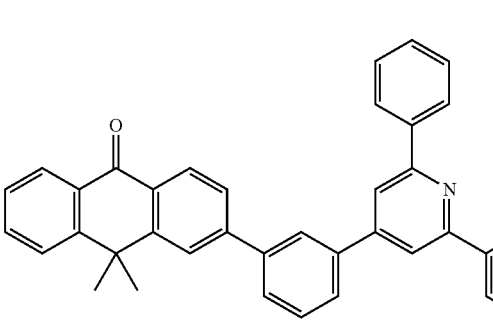

(99)
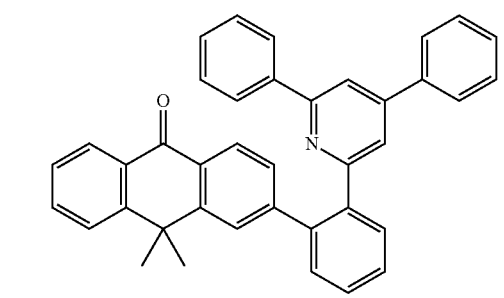
(100)
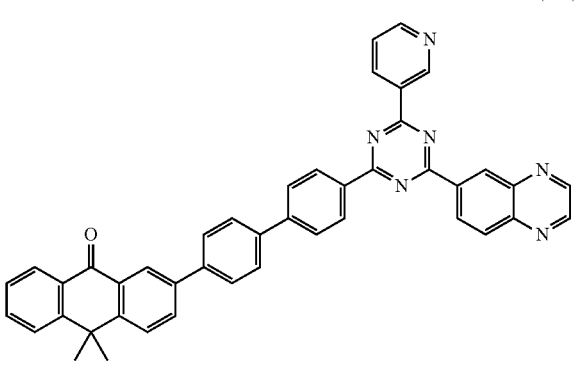
(101)
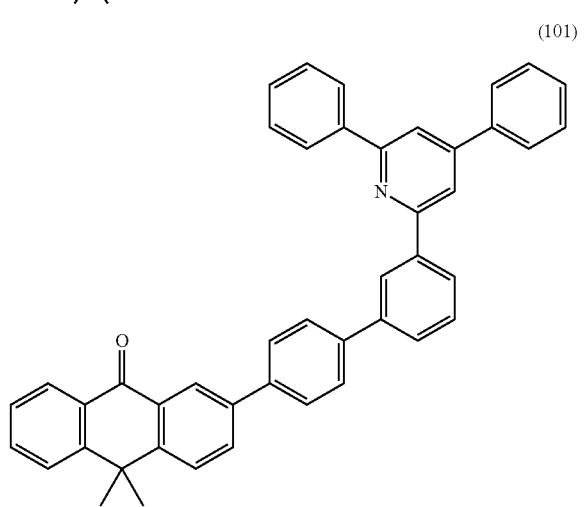
(102)
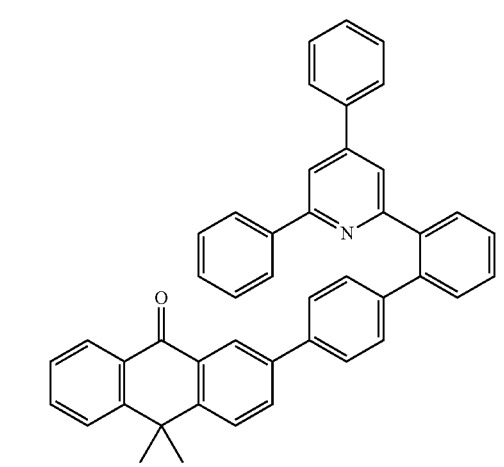
(103)
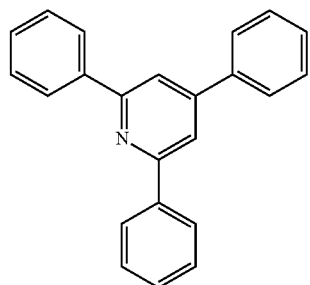
(104)
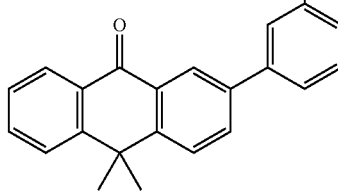
(105)
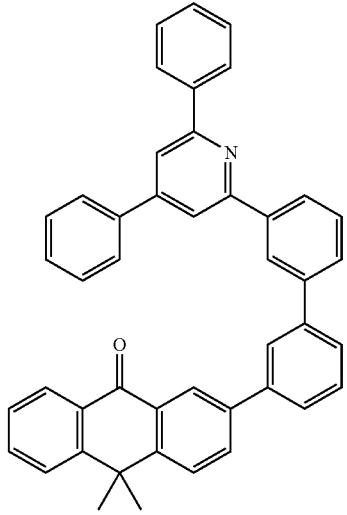

(106)
(107)
(108)
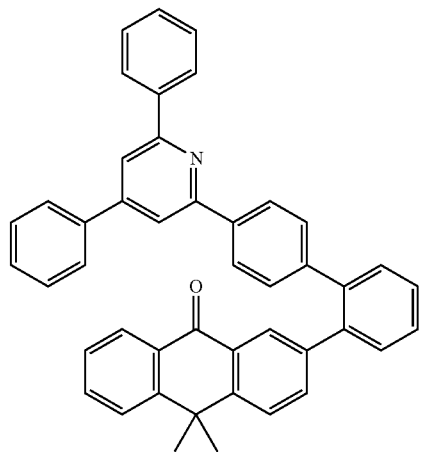
(109)
(110)
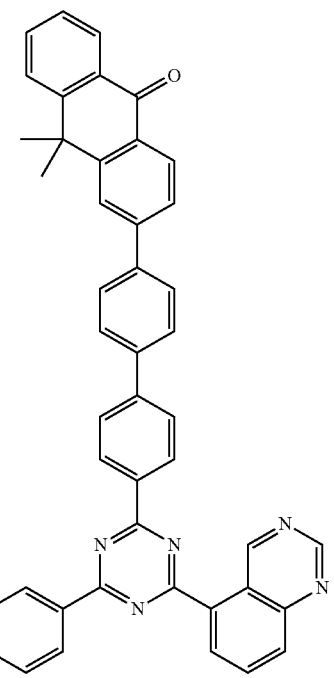
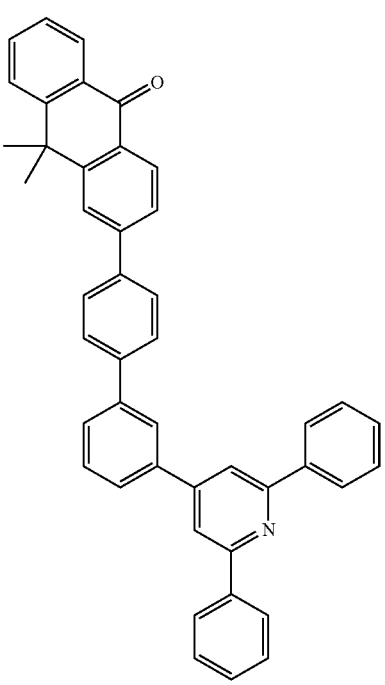

(111)
(112)
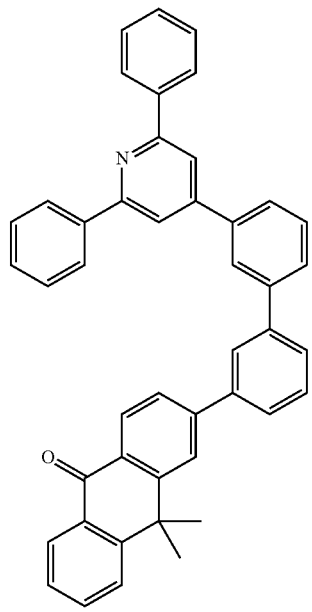
(113)
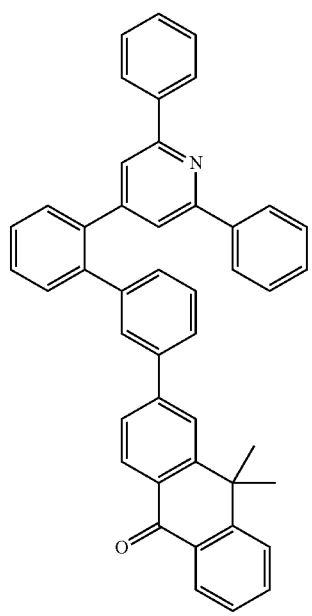
(114)
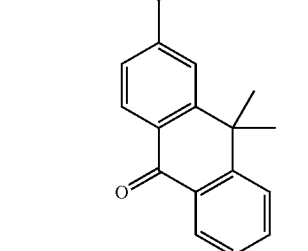
(115)
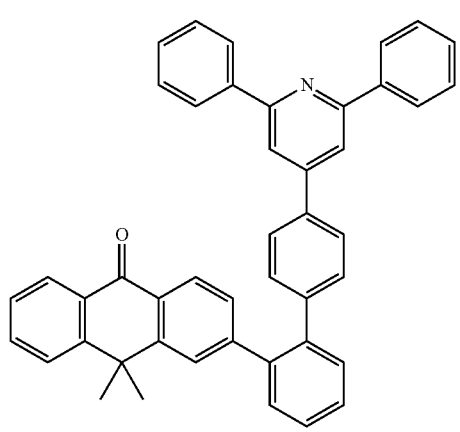

(116)
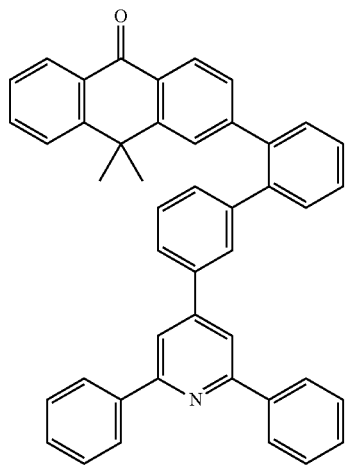
(117)
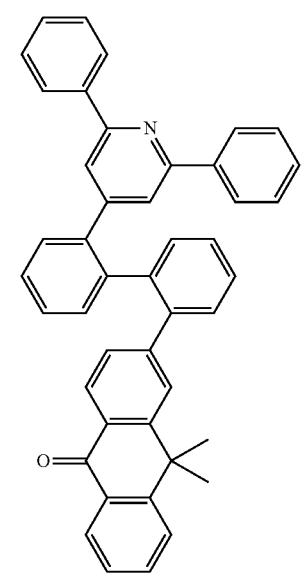
(118)
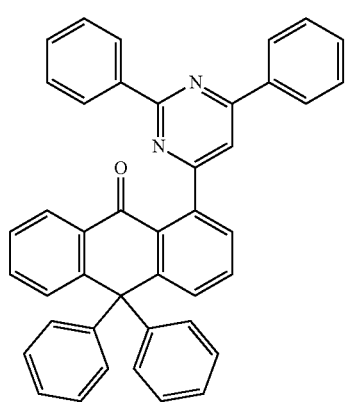
(119)
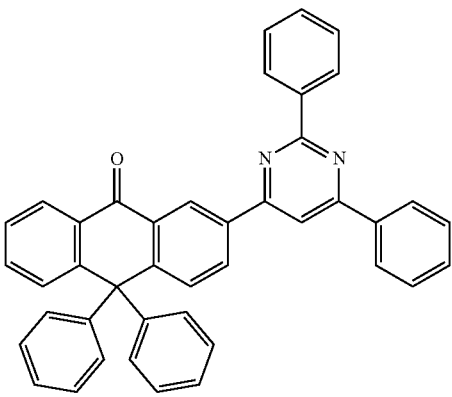
(120)
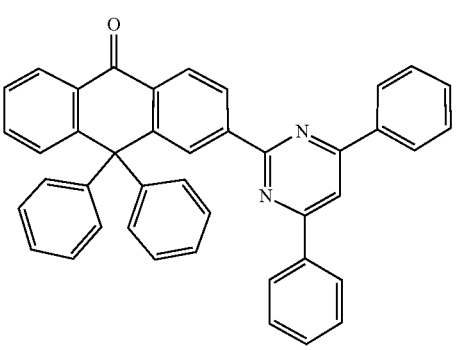
(121)
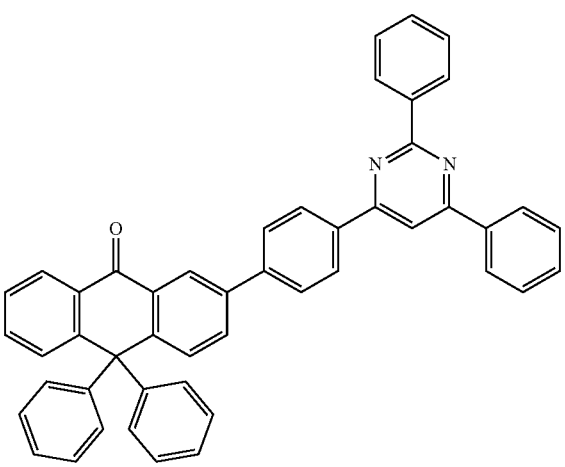

(122)
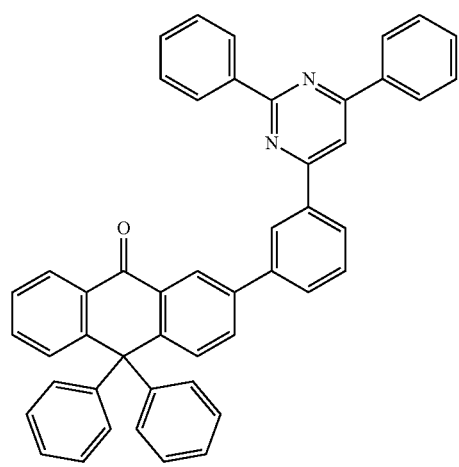
(123)
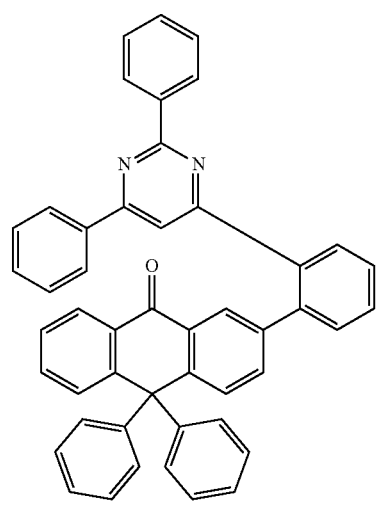
(124)
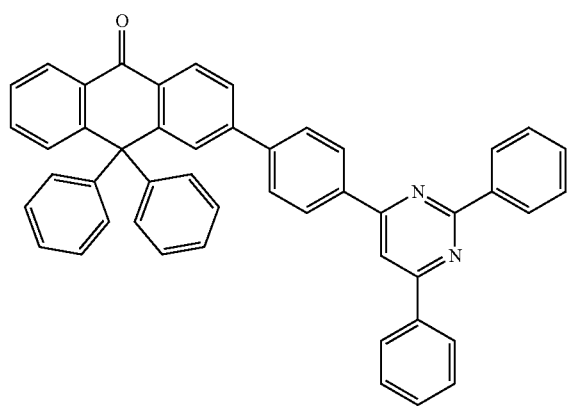
(125)
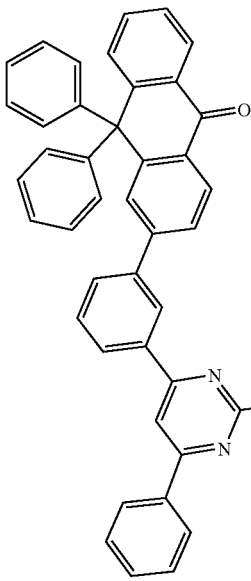
(126)
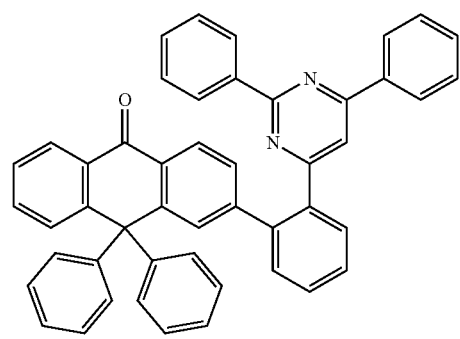
(127)
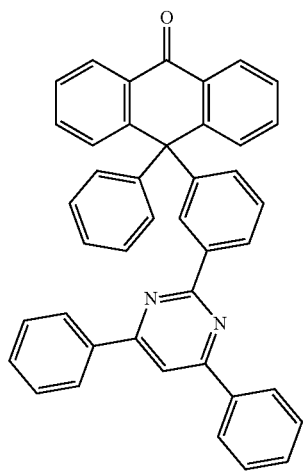

-continued
(128)
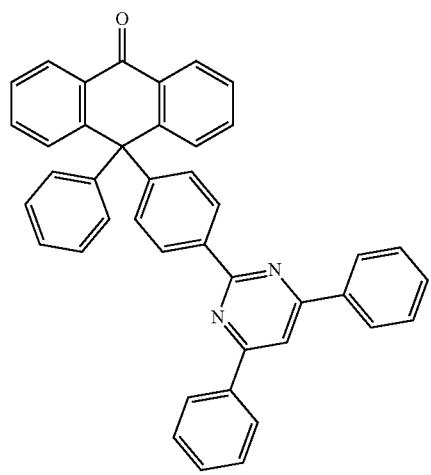
(129)
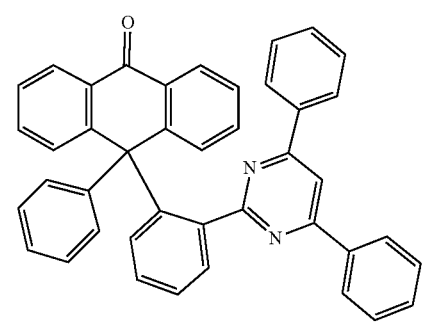
(130)
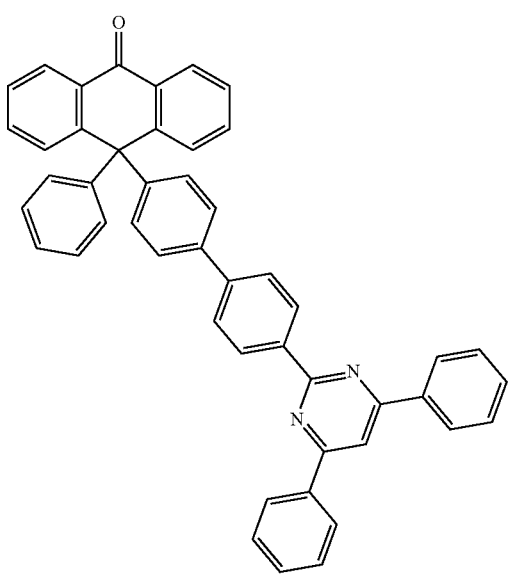
-continued
(131)
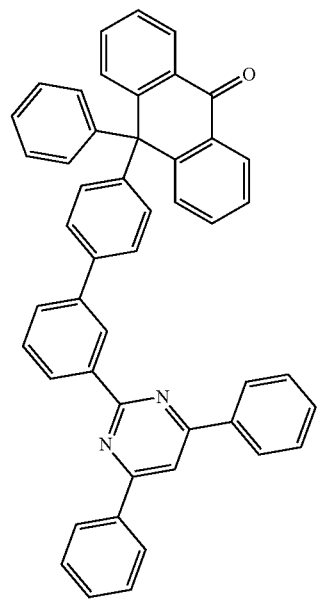
(132)
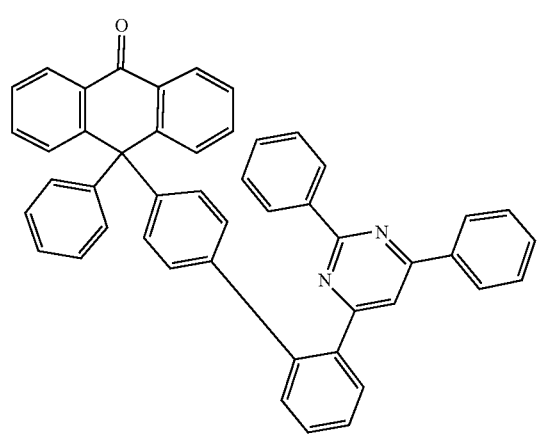
(133)
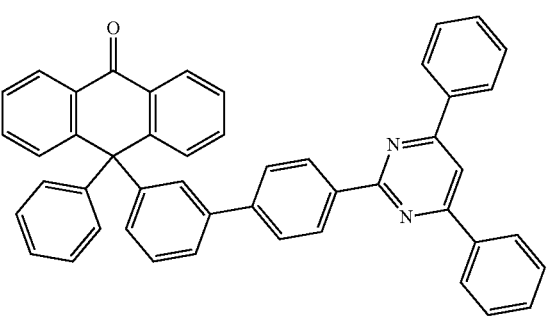

(134)
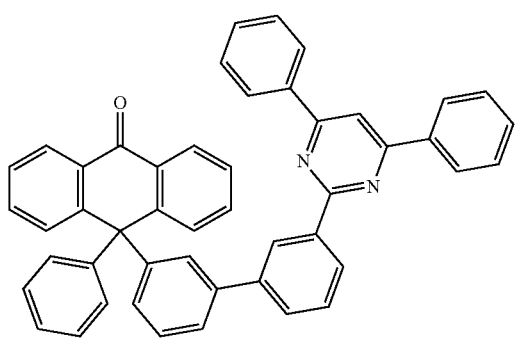
(137)
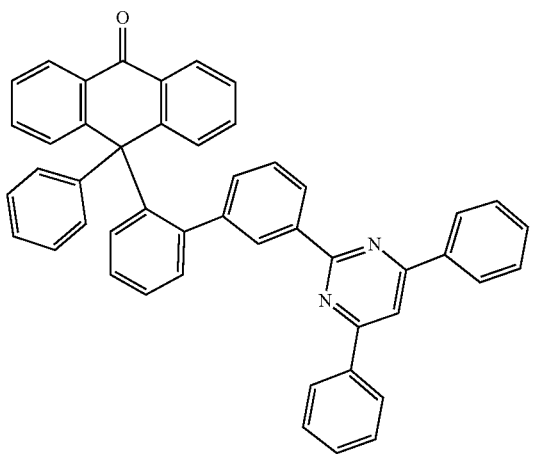
(135)
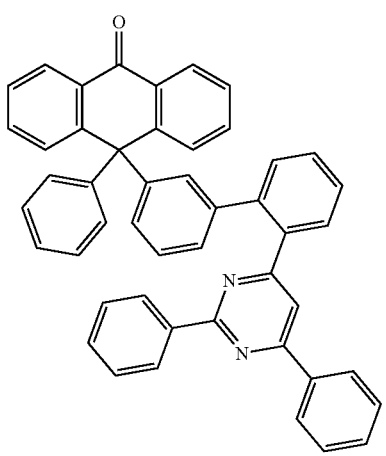
(138)
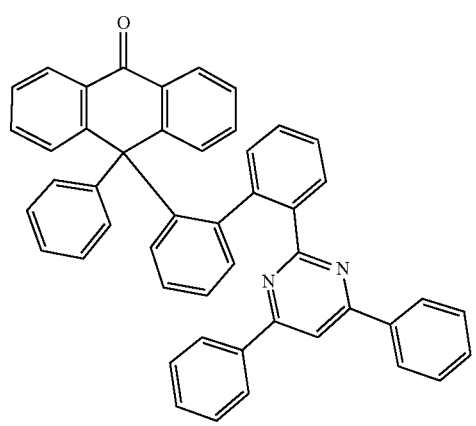
(139)
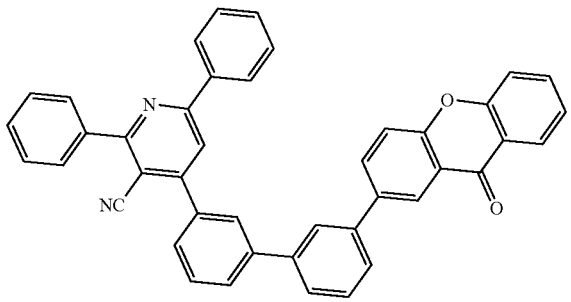
(136)
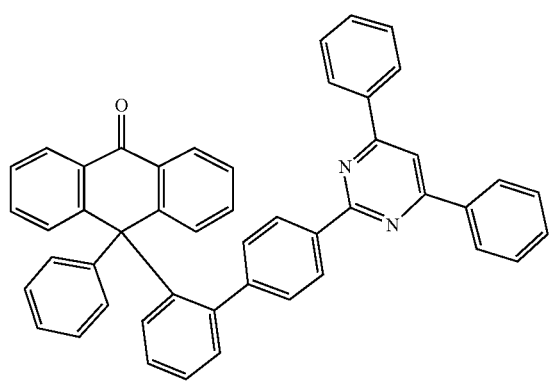
(140)
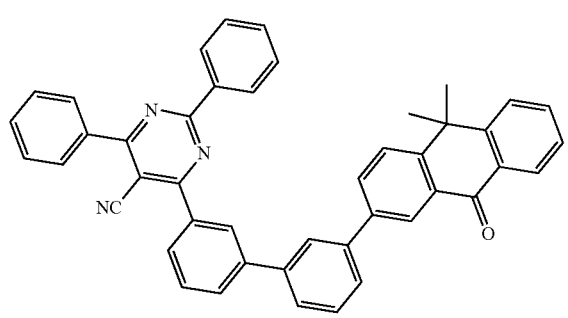

-continued
(141)
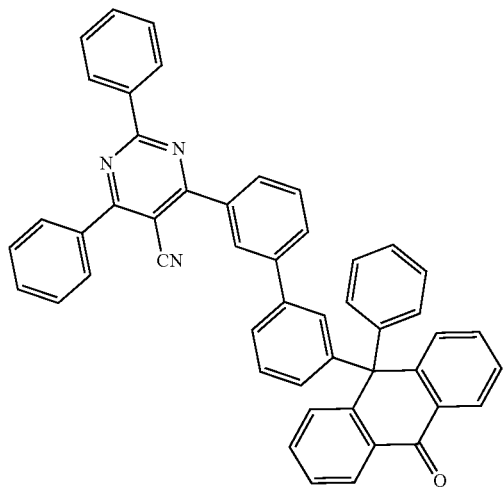
(142)
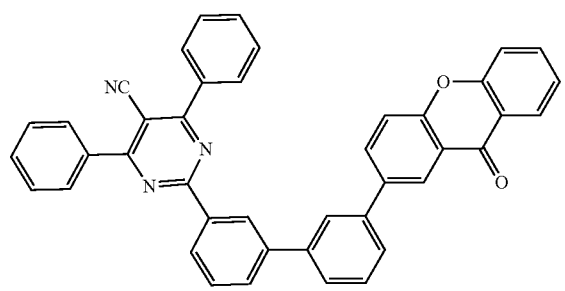
(143)
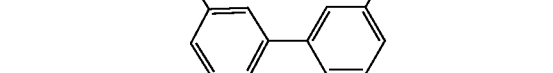
(144)
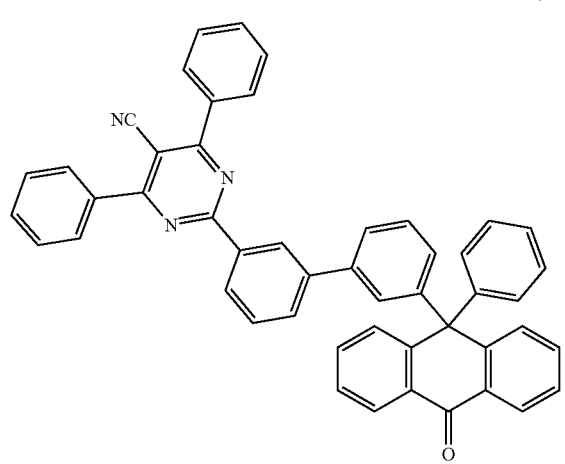
-continued
(145)
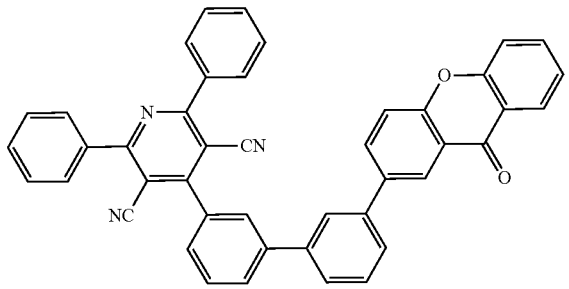
(146)
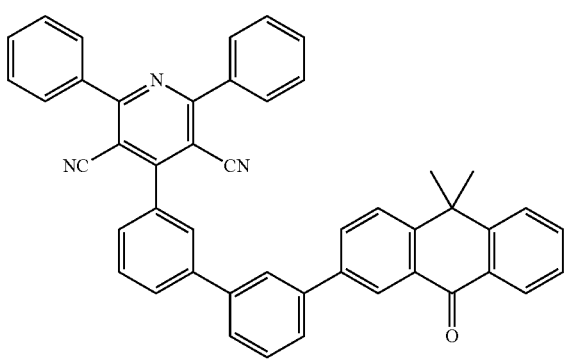
(147)
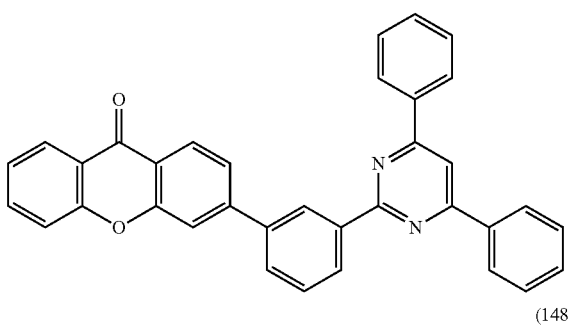
(148)
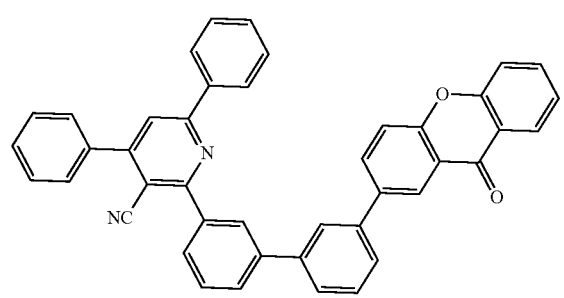
(149)
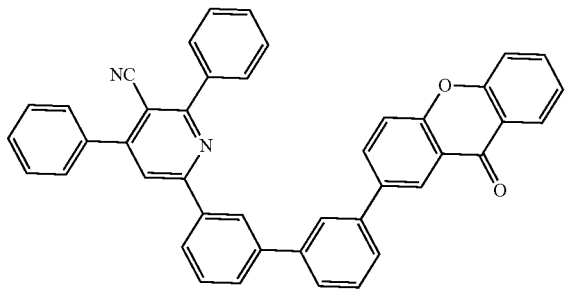

(150)
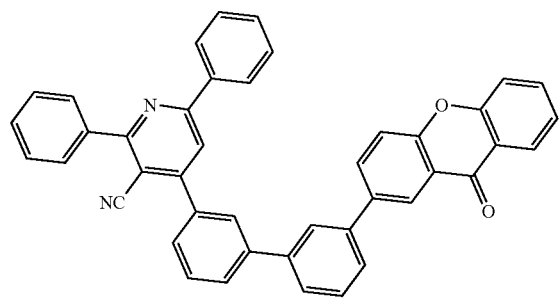
(151)
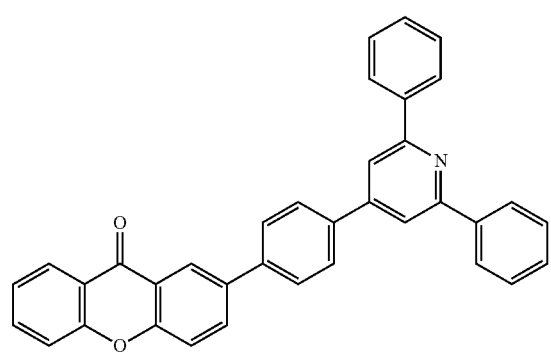
(152)
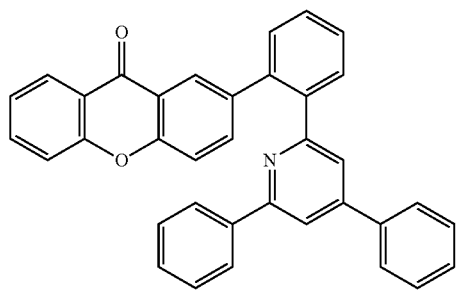
(153)
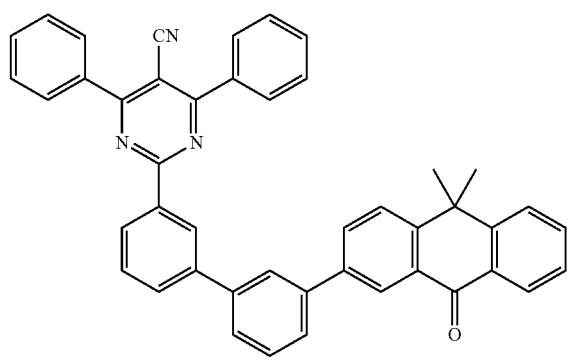
(154)
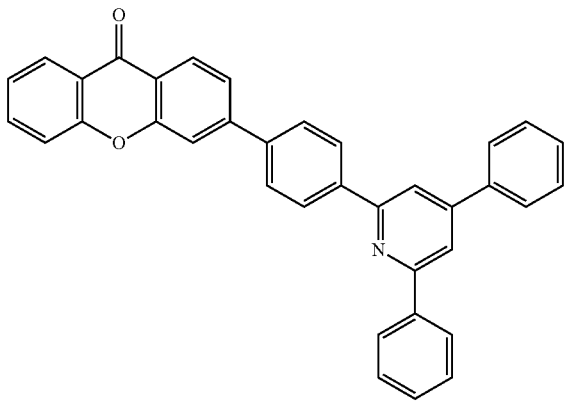
(155)
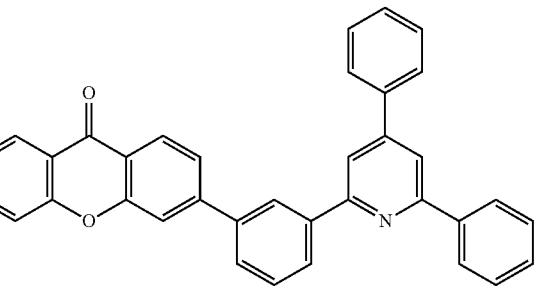
(156)
(157)
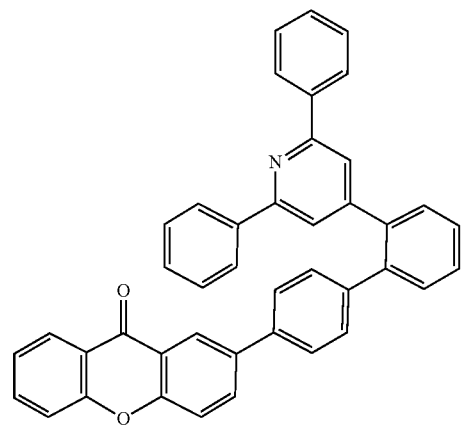

(158) 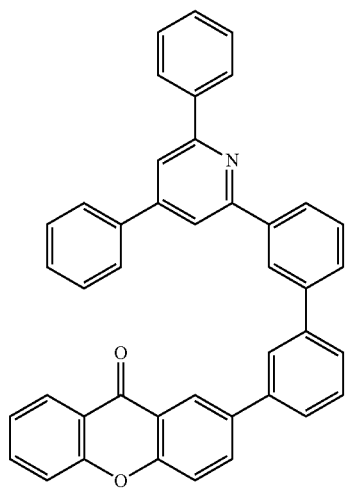
(159) 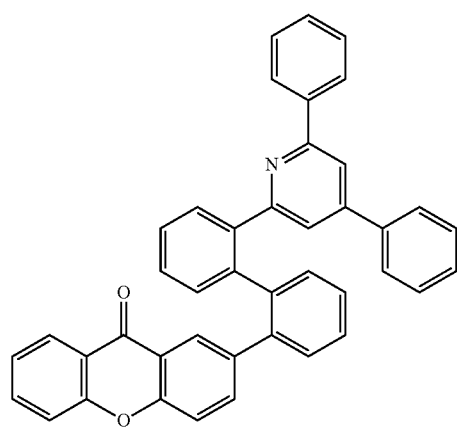
(160) 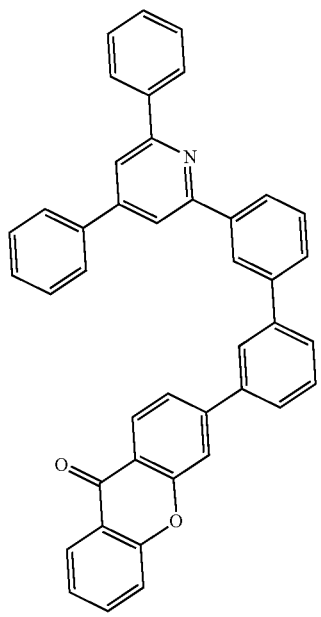
(161) 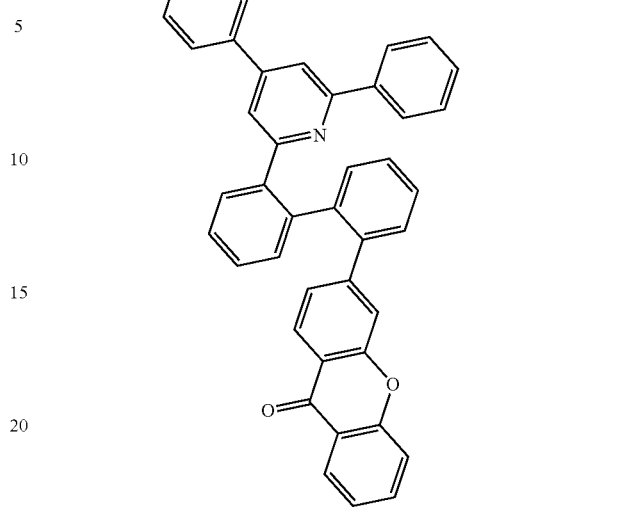
(162) 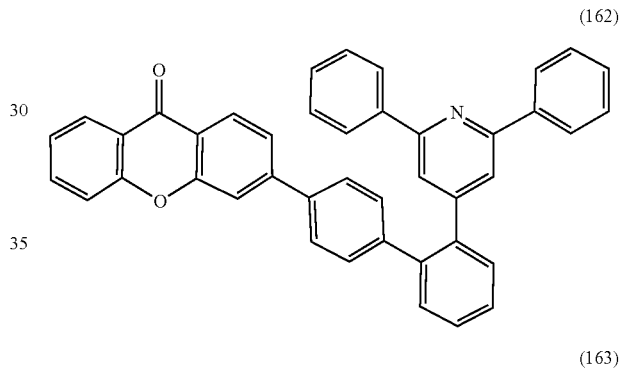
(163) 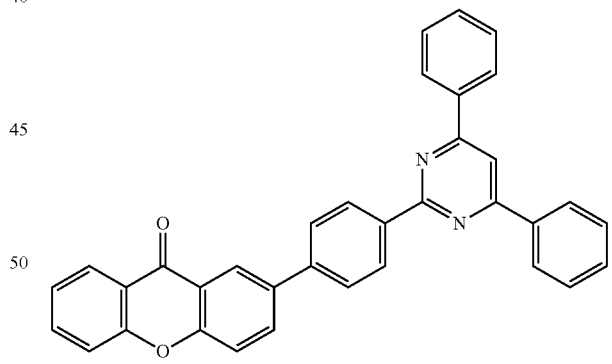
(164) 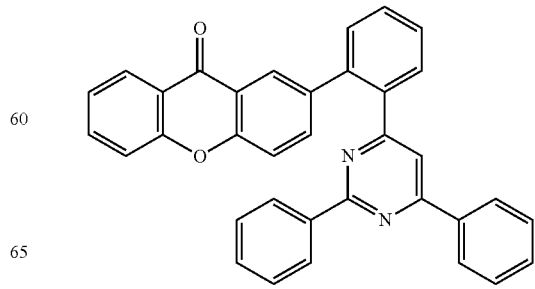

(165)
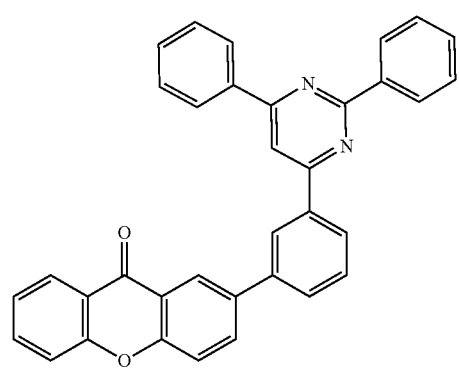
(166)
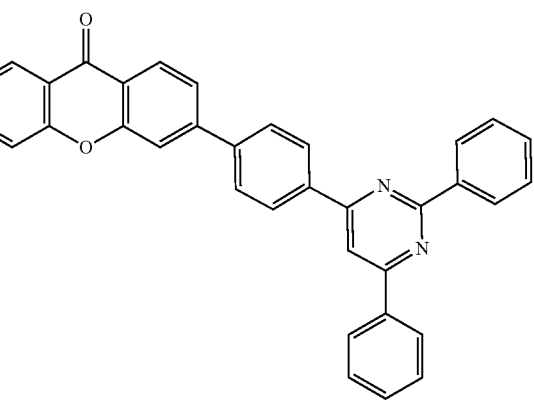
(167)
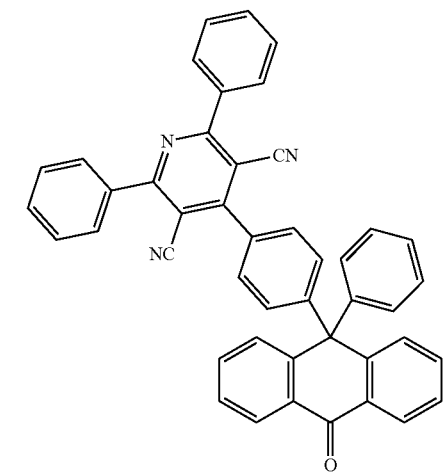
(168)
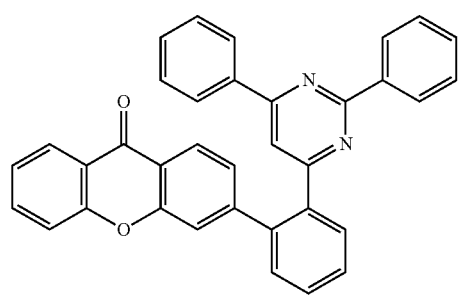
(169)
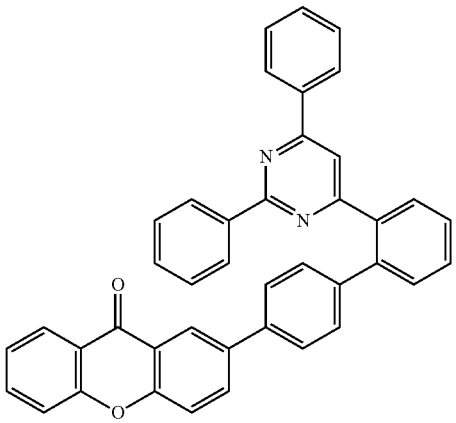
(170)
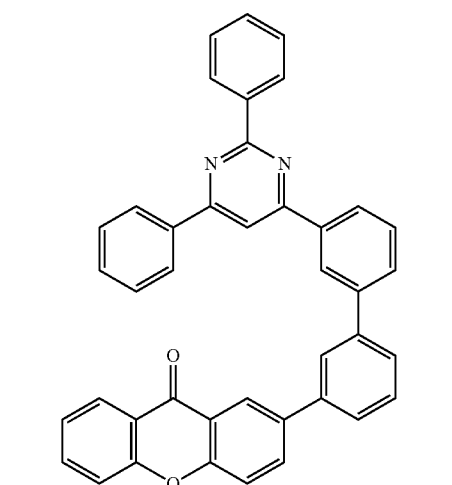
(171)
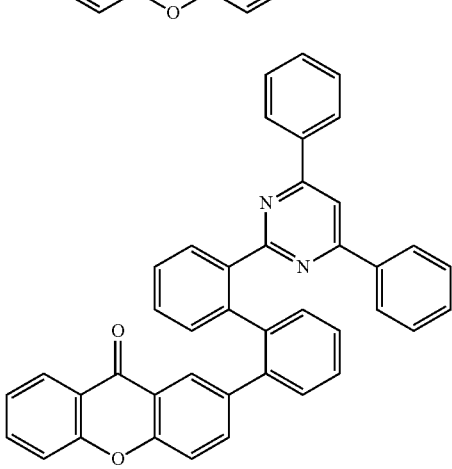
(172)
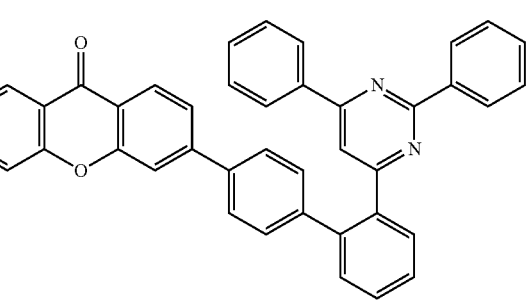

-continued (173)

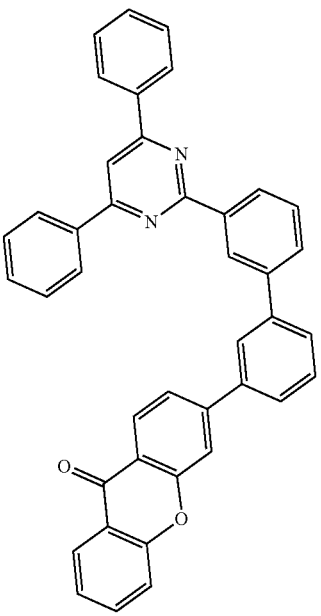

(174)

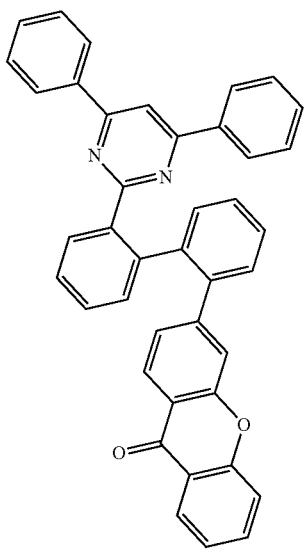
and (175)

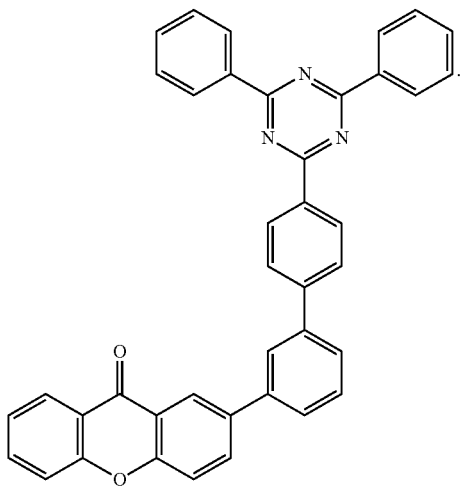

2. An organic electroluminescent device containing a compound represented by formula (1):

formula (1)

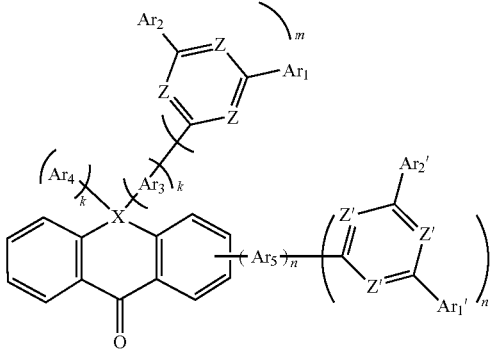

wherein

Z and Z' identically or differently represent CH, N or C—CN, wherein at least one Z group represents N or at least one Z' group represents N;

$Ar_1$, $Ar_2$, $Ar_1'$, $Ar_2'$, and $Ar_4$ each independently represent hydrogen atom, substituted or unsubstituted aryl with 6 to 30 carbon atoms, or substituted or unsubstituted heteroaryl with 5 to 30 carbon atoms; $Ar_4$ further represents linear or branched alkyl with 1 to 10 carbon atoms;

$Ar_3$ and $Ar_5$ each independently represent single-bond, substituted or unsubstituted arylene with 6 to 30 carbon atoms, or substituted or unsubstituted heteroarylene with 5 to 30 carbon atoms;

$Ar_3$ further represents linear or branched alkyl with 1 to 10 carbon atoms, substituted or unsubstituted aryl with 6 to 30 carbon atoms, or substituted or unsubstituted heteroaryl with 5 to 30 carbon atoms;

X represents carbon atom, oxygen atom or sulfur atom;

when X represents carbon atom, k=1, m and n each independently represent 0 or 1, and m and n are different;

when X represents oxygen atom or sulfur atom, k=0, m=0, n=1, wherein the organic electroluminescent device comprises at least one functional layer containing the compound, wherein the organic electroluminescent device comprises a hole block layer or an electron transport layer, wherein the hole block layer or the electron transport layer contains the compound.

3. The organic electroluminescent device according to claim 2, wherein the compound is represented by formula (2), formula (3), formula (4), formula (5), formula (6), formula (7) or formula (8):

formula (2)

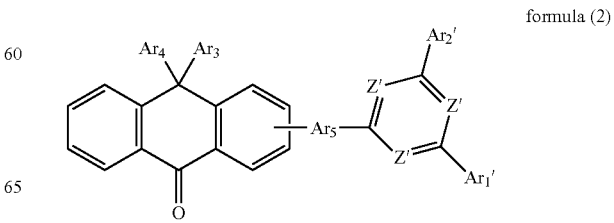

formula (3)

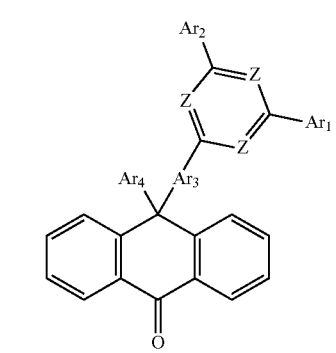

formula (4)

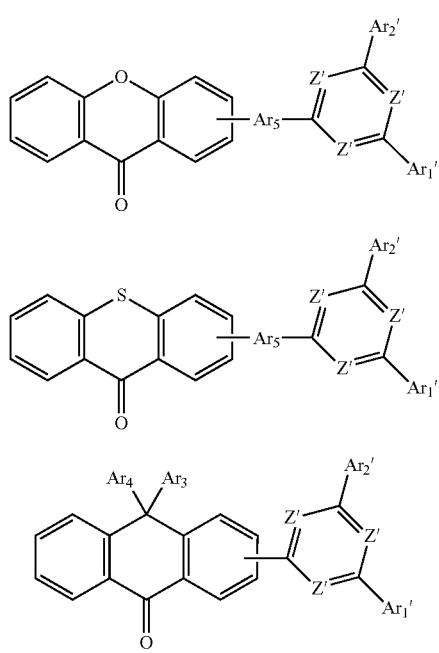

formula (5)

formula (6)

formula (7)

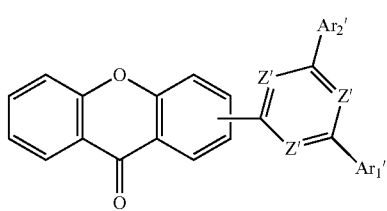

formula (8)

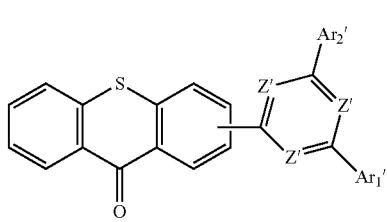

4. An organic electroluminescent device containing the compound according to claim 1, wherein the organic electroluminescent device comprises a light-emitting layer, wherein the light-emitting layer contains the compound.

5. An organic electroluminescent device containing the compound according to claim 1, wherein the organic electroluminescent device comprises at least one functional layer containing the compound.

6. The electroluminescent device according to claim 5, wherein the organic electroluminescent device comprises a hole block layer or an electron transport layer, wherein the hole block layer or the electron transport layer contains the compound.

* * * * *